United States Patent
Hwang et al.

(10) Patent No.: US 8,288,014 B2
(45) Date of Patent: Oct. 16, 2012

(54) FLUORENE-CONTAINING COMPOUND AND ORGANIC LIGHT EMITTING DEVICE EMPLOYING THE SAME

(75) Inventors: Seok-Hwan Hwang, Yongin (KR); Young-Kook Kim, Yongin (KR); Yoon-Hyun Kwak, Yongin (KR); Jeoung-In Yi, Yongin (KR); Chang-Ho Lee, Yongin (KR)

(73) Assignee: Samsung Mobile Display Co., Ltd., Nongseo-Dong, Giheung-Gu, Yongin, Gyunggi-Do (KR)

( * ) Notice: Subject to any disclaimer, the term of this patent is extended or adjusted under 35 U.S.C. 154(b) by 442 days.

(21) Appl. No.: 12/546,824

(22) Filed: Aug. 25, 2009

(65) Prior Publication Data

US 2010/0051924 A1    Mar. 4, 2010

(30) Foreign Application Priority Data

Sep. 3, 2008  (KR) .................. 10-2008-0086799

(51) Int. Cl.
*H01L 51/50*  (2006.01)
(52) U.S. Cl. ........ 428/690; 428/917; 313/504; 313/505; 313/506; 257/40; 257/E51.05; 257/E51.026; 257/E51.032; 564/26; 564/426; 564/434
(58) Field of Classification Search .................. 428/690, 428/917; 564/26, 426, 434; 313/504, 505, 313/506; 257/40, E51.05, E51.026, E51.032
See application file for complete search history.

(56) References Cited

U.S. PATENT DOCUMENTS

| | | | |
|---|---|---|---|
| 4,356,429 A | 10/1982 | Tang | |
| 6,465,115 B2 | 10/2002 | Shi et al. | |
| 6,485,847 B1 | 11/2002 | Uchida et al. | |
| 6,596,415 B2 | 7/2003 | Shi et al. | |
| 2003/0138662 A1* | 7/2003 | Li et al. ................. | 428/690 |
| 2003/0157364 A1* | 8/2003 | Senoo et al. ............ | 428/690 |
| 2004/0185299 A1 | 9/2004 | Ly | |
| 2005/0170209 A1 | 8/2005 | Lee et al. | |
| 2005/0221124 A1 | 10/2005 | Hwang et al. | |
| 2007/0029927 A1 | 2/2007 | Kawamura et al. | |
| 2008/0303417 A1 | 12/2008 | Yabunouchi et al. | |
| 2009/0091244 A1 | 4/2009 | Negishi et al. | |

(Continued)

FOREIGN PATENT DOCUMENTS

JP    62201451 A    9/1987

(Continued)

OTHER PUBLICATIONS

Korean Office Action dated Aug. 30, 2010, issued in corresponding Korean Patent Application No. 10-2008-0086799.

(Continued)

*Primary Examiner* — Jennifer Chriss
*Assistant Examiner* — Gregory Clark
(74) *Attorney, Agent, or Firm* — Robert E. Bushnell, Esq.

(57) ABSTRACT

A novel fluorene-containing compound and an organic electroluminescent device including an organic layer employing the same. The fluorene-containing compound has excellent electrical characteristics and an excellent charge transporting capability, and so can be used as a hole injecting material, hole transporting material, and/or emitting material that is suitable for all-color fluorescent and phosphorescent devices, such as red, green, blue, and white fluorescent and phosphorescent devices. Accordingly, an organic electroluminescent device employing the fluorene-containing compound has high efficiency, a low driving voltage, high brightness, and a long lifetime.

16 Claims, 1 Drawing Sheet

U.S. PATENT DOCUMENTS

2009/0200928 A1    8/2009    Hwang et al.

FOREIGN PATENT DOCUMENTS

| JP | 1135532 A | 2/1999 |
| JP | 11124358 A | 5/1999 |
| JP | 11-288783 | 10/1999 |
| JP | 11-329734 | 11/1999 |
| JP | 2004536134 A | 12/2004 |
| JP | 2005290000 A | 10/2005 |
| JP | 200745725 A | 2/2007 |
| JP | 2009185030 A | 8/2009 |
| KR | 10-0537621 | 12/2005 |
| KR | 1020080077023 A | 8/2008 |
| WO | 2006073054 | 7/2006 |

OTHER PUBLICATIONS

Registration Determination Certificate issued by Korean Intellectual Property Office on Jun. 21, 2011, corresponding to Korean Application No. 10-2008-0086799 and Request for Entry of the Accompanying Office Action attached herewith.

"Thermally Stable Multilayered Organic Electroluminescent Devices Using Novel Starburst Molecules, 4,4', 4"-Tri(N-carbazolyl)triphenylamine (TCTA) and 4,4',4"-Tris(3-methylphenylphenyl-amino)triphenylamine (m-MTDATA), as Hole-Transport Materials," Yoshiyuki Kuwabara et al., *Advanced Materials*, 6, (1994), No. 9 p. 677-679.

"Endothermic energy transfer: A mechanism for generating ver efficient high-energy phosphorescent emission in organic materials," Chihaya Adachi et al., *Applied Physics Letters*, vol. 79, No. 13, Sep. 24, 2001, pp. 2082-2084.

Japanese Office Action issued by JPO on May 8, 2012 in connection with Japanese Patent Application Serial No. 2009-204042, which also claims Korean Patent Application No. 10-2008-0086799 as its priority document and Request for Entry of the Accompanying Office Action attached herewith.

* cited by examiner

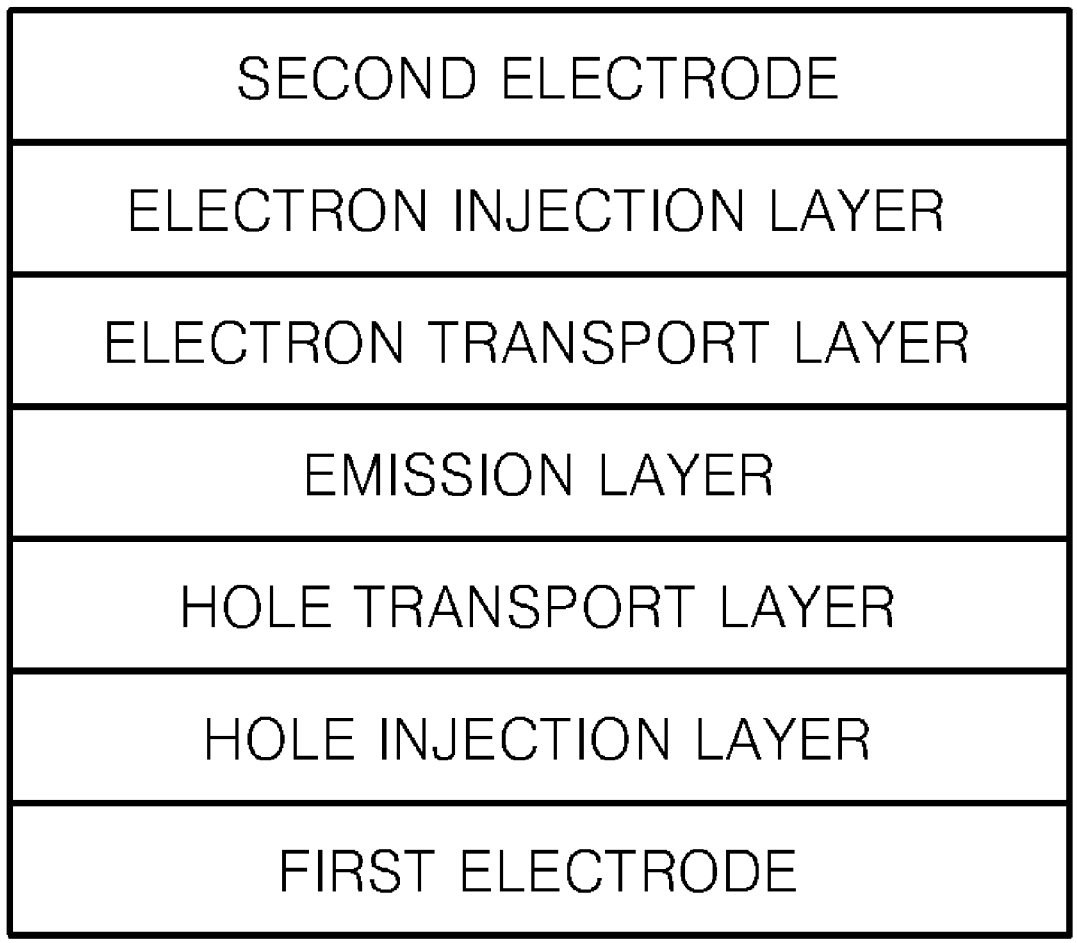

FLUORENE-CONTAINING COMPOUND AND ORGANIC LIGHT EMITTING DEVICE EMPLOYING THE SAME

CROSS-REFERENCE TO RELATED APPLICATION

This application claims the benefit of Korean Patent Application No. 2008-86799, filed Sep. 3, 2008 in the Korean Intellectual Property Office, the disclosure of which is incorporated herein by reference.

BACKGROUND OF THE INVENTION

1. Field of the Invention

Aspects of the present invention relate to a fluorene-containing compound and an organic electroluminescent device employing the same, and more particularly, to a fluorene-containing compound having excellent electrical characteristics and an excellent charge transporting capability as well as an organic electroluminescent device employing the same and a flat panel apparatus including the organic electroluminescent device.

2. Description of the Related Art

Electroluminescent devices are self-emission type display devices and have wide viewing angles, high contrast ratios and short response times. Due to such characteristics, electroluminescent devices are getting more attention.

Electroluminescent devices are generally classified into inorganic electroluminescent devices including an emission layer employing an inorganic compound and organic electroluminescent devices including an emission layer employing an organic compound. Specifically, organic electroluminescent devices have higher luminescent characteristics, lower driving voltages and shorter response speeds than inorganic electroluminescent devices. In addition, organic electroluminescent devices produce various colors. Due to those characteristics, much research into organic electroluminescent devices is being performed. In general, an organic electroluminescent device has a stack structure of anode/organic emission layer/cathode, or when a hole injection layer and/or a hole transport layer and/or an electron injection layer are further stacked between the anode and the emission layer or between the emission layer and the cathode, a stack structure of anode/hole transport layer/organic emission layer/cathode or a stack structure of anode/hole transport layer/organic emission layer/electron transport layer/cathode.

Meanwhile, polyphenyl compounds or anthracene derivatives are well known as hole transport layer forming materials (see U.S. Pat. Nos. 6,596,415 and 6,465,115). However, organic electroluminescent devices employing conventional hole injection layer and/or hole transport layer forming materials still needs to be improved in terms of lifetime, efficiency, and power consumption.

SUMMARY OF THE INVENTION

Aspects of the present invention provide a fluorene-containing compound having excellent electrical characteristics and an excellent charge transporting capability, which compound is used as an organic layer forming material that is appropriate for use in all-color fluorescent and phosphorescent organic light emitting devices such as red, green, blue, and white fluorescent and phosphorescent organic light emitting devices. Aspects of the present invention also provide an organic electroluminescent device having high efficiency, a low driving voltage, high luminosity, and a long lifetime where the device incorporates an organic layer employing the fluorene-containing compound, as well as a flat panel apparatus including the organic electroluminescent device.

An aspect of the present invention provides a fluorene-containing compound represented by Formula 1 or Formula 2:

<Formula 1>

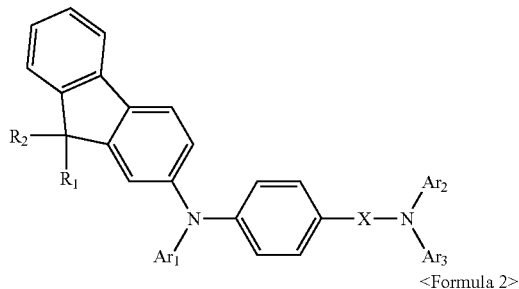

<Formula 2>

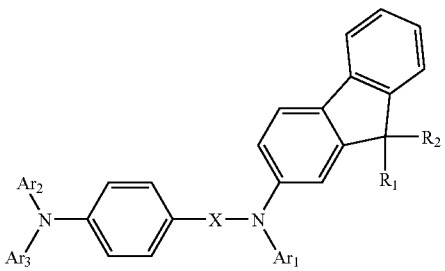

wherein $Ar_1$, $Ar_2$ and $Ar_3$ are each, independently, a C6-C20 substituted or unsubstituted aryl group, a C6-C20 substituted or unsubstituted aryloxy group, a C4-C20 substituted or unsubstituted heteroring, or a C4-C20 substituted or unsubstituted condensed polycyclic group; X is a C6-C20 substituted or unsubstituted aryl group, a C4-C15 substituted or unsubstituted hetero aryl group, or a C4-C20 substituted or unsubstituted condensed polycyclic group; and $R_1$ and $R_2$ are each, independently, a $C_1$-C10 substituted or unsubstituted alkyl group, a C6-C20 aryl group, a C1-C10 substituted or unsubstituted alkoxy group, a fluorine group, a cyano group, or an amine group.

Another aspect of the present invention provides an organic electroluminescent device including: a first electrode; a second electrode; and an organic layer interposed between the first electrode and the second electrode, wherein the organic layer comprises the fluorene compound described above. According to an embodiment of the present invention, the organic layer may be selected from a hole injection layer, a hole transport layer, or an emission layer.

Another aspect of the present invention provides a flat panel display device including the organic electroluminescent device described above, wherein the first electrode of the organic electroluminescent device is electrically connected to a source electrode or drain electrode of a thin film transistor.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawing of which:

FIG. 1 illustrates a schematic view of an organic electroluminescent device according to an embodiment of the present invention.

DETAILED DESCRIPTION OF THE EMBODIMENTS

Reference will now be made in detail to the present embodiments of the present invention, examples of which are illustrated in the accompanying drawings, wherein like reference numerals refer to the like elements throughout. The embodiments are described below in order to explain the present invention by referring to the figures.

An aspect of the present invention is directed to a compound represented by Formula 1 or Formula 2:

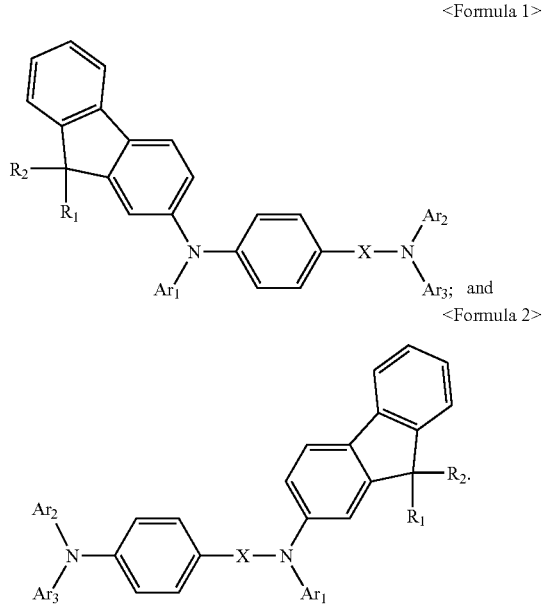

<Formula 1>

<Formula 2> wherein $Ar_1$, $Ar_2$ and $Ar_3$ are each, independently, a C6-C20 substituted or unsubstituted aryl group, a C6-C20 substituted or unsubstituted aryloxy group, a C4-C20 substituted or unsubstituted heteroring, or a C4-C20 substituted or unsubstituted condensed polycyclic group; X is a C6-C20 substituted or unsubstituted aryl group, a C4-C15 substituted or unsubstituted hetero aryl group, or a C4-C20 substituted or unsubstituted condensed polycyclic group; and $R_1$, and $R_2$ are each, independently, a C1-C10 substituted or unsubstituted alkyl group, a C6-C20 aryl group, a C1-C10 substituted or unsubstituted alkoxy group, a fluorine group, a cyano group, or an amine group.

The fluorene-containing compound represented by Formula 1 or 2 is an asymmetric amine compound that has an asymmetric core having a phenylene group and a fluorenyl group, wherein the fluorenyl group is bonded to either of two atoms in the asymmetric amine compound. The fluorene-containing compound represented by Formula 1 or 2 may have a high glass transition temperature (Tg) or a high melting point due to introduction of a naphthalene or an anthracene group. Accordingly, when electroluminescence occurs, the fluorene-containing compound has high heat resistance against Joule heat occurring in an organic layer, between organic layers, or between an organic layer and a metallic electrode as well as high durability in a high-temperature environment. As described above, an organic electroluminescent device manufactured using the fluorene-containing compound has high durability during preservation and operation.

In Formulae 1 and 2, $Ar_1$, $Ar_2$ and $Ar_3$ may each be, independently, a substituted or unsubstituted C6-C20 aryl group, a substituted or unsubstituted C4-C20 heteroaryl group or a C4-C20 substituted or unsubstituted condensed polycyclic group. The carbon number of those aromatic substituents may be 20 or less because when the molecular weight of the compound represented by Formula 1 or 2 is too high, deposition is difficult.

Specifically, each of $Ar_1$, $Ar_2$ and $Ar_3$ may be a phenyl group, a lower alkylphenyl group, a lower alkoxyphenyl group, a cyanophenyl group, a phenoxyphenyl group, a fluorophenyl group, a naphthyl group, a lower alkylnaphthyl group, a lower alkoxynaphthyl group, a cyanonaphthyl group, a halonaphthyl group, a fluorenyl group, a carbazolyl group, a lower alkylcarbazolyl group, a biphenyl group, a lower alkylbiphenyl group, a lower alkoxybiphenyl group, or a pyridyl group. The carbon number of those lower alkyl or alkoxy groups may be 1 to 5.

More specifically, each of $Ar_1$, $Ar_2$ and $Ar_3$ may be an aryl group selected from a phenyl group, a naphthyl group, and a biphenyl group, each of which may be unsubstituted or substituted with one, two or three substituents, specifically one of a substituent selected from a C1-C4 alkyl group, a C1-C5 alkoxy group, a cyano group, an amine, a phenoxy group, a phenyl group and a halogen.

Examples of $Ar_1$, $Ar_2$ and $Ar_3$ include a phenyl group, a methylphenyl group, an ethylphenyl group, a methylbiphenyl group, an ethylbiphenyl group, o-, m- and p-fluorophenyl groups, a dichlorophenyl group, a dicyano phenyl group, a trifluorophenyl group, a methoxyphenyl group, o-, m-, and p-tolyl groups, a mesityl group, a phenoxyphenyl group, an (α,α-dimethylbenzene)phenyl group, an (N,N'-dimethyl) aminophenyl group, an (N,N'-diphenyl)aminophenyl group, a pentalenyl group, a naphthyl group, a methylnaphthyl group, an anthracenyl group, an azrenyl group, a heptarenyl group, an acenaphthylenyl group, a fluorenyl group, an anthraquinolyl group, a phenanthryl group, a triphenylene group, a pentaphenyl group, a hexaphenyl group, and a carbazolyl group. However, $Ar_1$, $Ar_2$ and $Ar_3$ are not limited to those materials. For example, each of $Ar_1$, $Ar_2$ and $Ar_3$ may be selected from the phenyl group, the methylphenyl group, the naphthyl group, and the biphenyl group.

In Formula 1 or 2, X may be a C6-C20 substituted or unsubstituted aryl group, a C4-C15 substituted or unsubstituted hetero aryl group, or a C4-C20 substituted or unsubstituted condensed polycyclic group. For example, X may have a structure selected from the structures illustrated in Formula 3, but is not limited thereto:

[Formula 3]

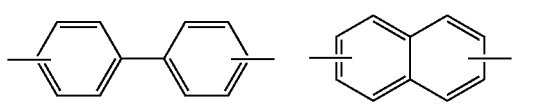

-continued

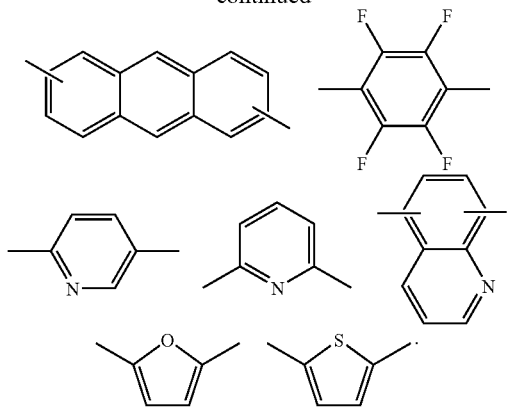

Specifically, X may have a structure selected from the structures illustrated in Formula 4:

[Formula 4]

In Formulae 1 and 2, $R_1$ and $R_2$ may each be, independently, a C1-C10 substituted or unsubstituted alkyl group, a C6-C20 aryl group, a C1-C10 substituted or unsubstituted alkoxy group, a halogen, a cyano group, or an amine group. For example, each of $R_1$ and $R_2$ is a C1-C10 alkyl group or a C6-C20 aryl group, specifically a methyl group or a phenyl group.

With regard to Formulae 1 and 2, the unsubstituted alkyl group may be methyl, ethyl, propyl, isobutyl, sec-butyl, pentyl, iso-amyl, hexyl, or the like. In those alkyl groups, at least one hydrogen atom may be substituted with a halogen atom, a hydroxyl group, a nitro group, a cyano group, an amino group, an amidino group, hydrazine, hydrazone, a carboxyl group or salt thereof, a sulfuric acid or salt thereof, a phosphoric acid or salt thereof, a C1-C10 alkyl group, a C1-C10 alkenyl group, a C1-C10 alkynyl group, a C6-C10 aryl group, a C7-C10 arylalkyl group, a C4-C10 heteroaryl group, or a C5-C10 heteroarylalkyl group.

With regard to Formulae 1 and 2, examples of the unsubstituted alkoxy group include methoxy, ethoxy, phenyloxy, cyclohexyloxy, naphthyloxy, isopropyloxy, and diphenyloxy. In those alkoxy groups, at least one hydrogen atom may be substituted with the substituents which have been described with the alkyl groups described above.

With regard to Formulae 1 and 2, the unsubstituted aryl group is used alone or in combination, and is an aromatic carbon ring having at least one ring, wherein when the number of aromatic rings is two or more, the aromatic rings may be pendent with respect to each other or condensed. In the unsubstituted aryl group, at least one hydrogen atom may be substituted with the substituents that have been described with the alkyl groups described above.

With regard to Formulae 1 and 2, examples of the unsubstituted aryloxy group include phenyloxy, naphthyleneoxy, and diphenyloxy. In the unsubstituted aryloxy group, at least one hydrogen atom may be substituted with the substituents that have been described with the alkyl groups described above.

With regard to Formulae 1 and 2, the unsubstituted heteroaryl group is a mono-valent monocyclic or bicyclic aromatic divalent organic compound that has 6-30 ring atoms which consist of one, two, or three hetero atoms selected from N, O, P and S as well as carbons. In the heteroaryl group, at least one hydrogen atom may be substituted with the substituents that have been described with the alkyl groups described above. Examples of the heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl, a pyrimidinyl group, a triazinyl group, a carbazolyl group, and an indolyl group.

With regard to Formulae 1 and 2, examples of the unsubstituted condensed polycyclic group include a pentalenyl group, a naphthyl group, an azrenyl group, a heptarenyl group, an acenaphthyl group, an anthryl group, a phenanthryl group, a quinolyl group, an anthraquinolyl group, a fluorenyl group, and a carbazolyl group. In the condensed polycyclic groups, at least one hydrogen atom may be substituted with the substituents that have been described with the alkyl groups described above.

Examples of the fluorene-containing compound represented by Formula 1 or 2 according to aspects of the present invention include Compounds 1 through 198. However, the fluorene-containing compound represented by Formula 1 or 2 according to aspects of the present invention may not be limited to those compounds.

1

2
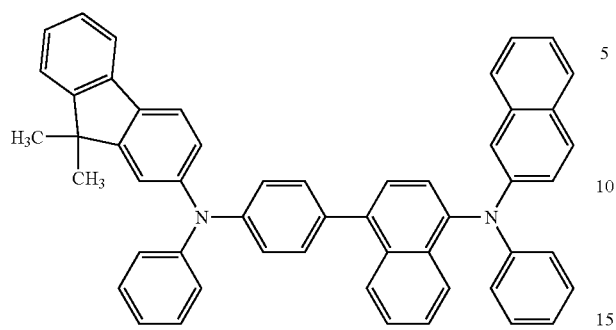
3
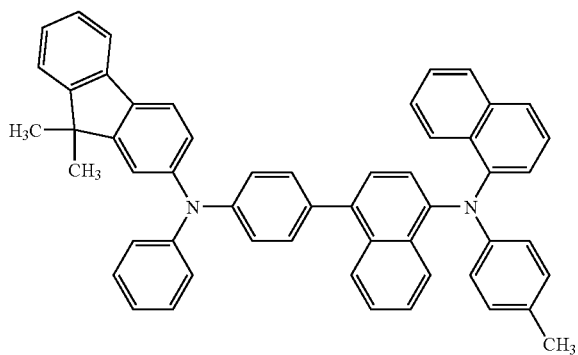
4
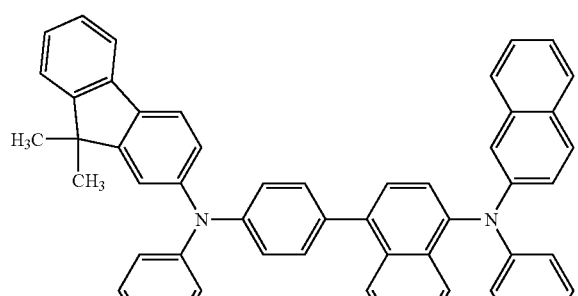
5
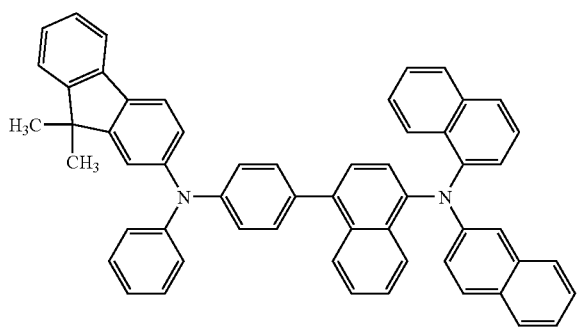
6
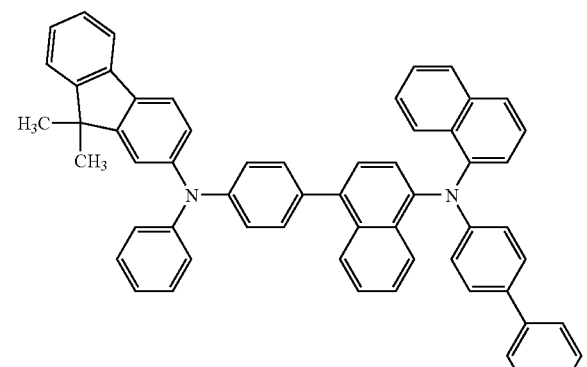
7
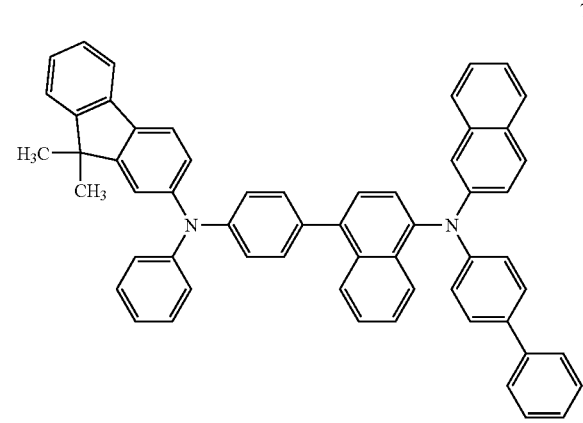
8
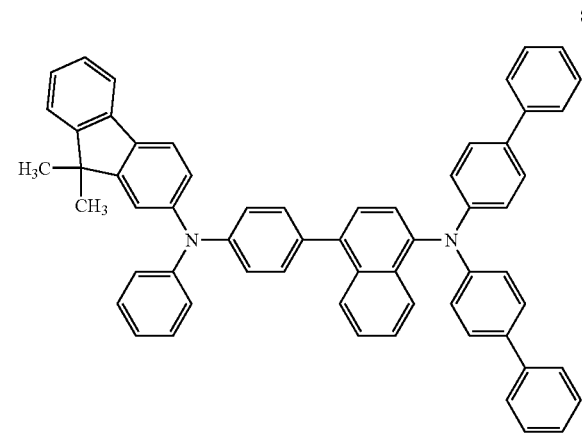
9
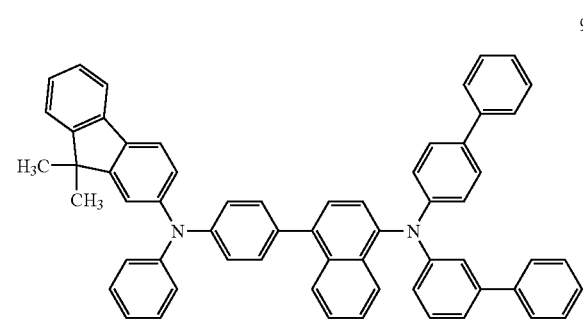

10
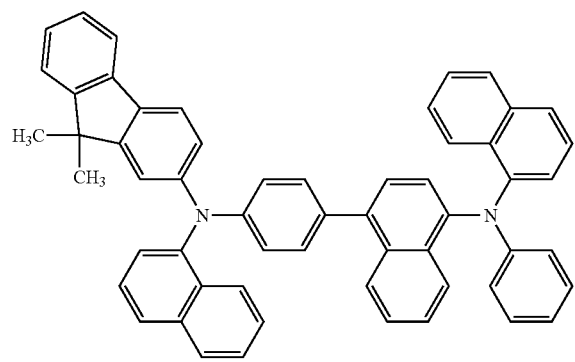
11
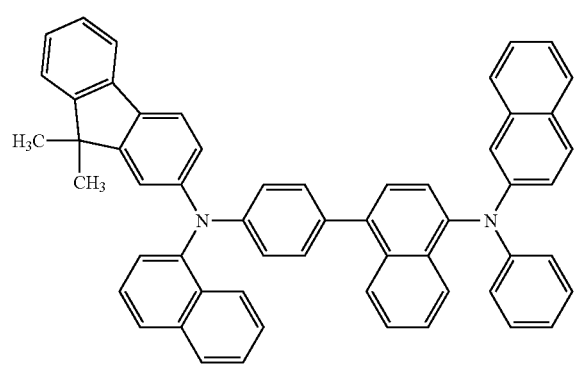
12
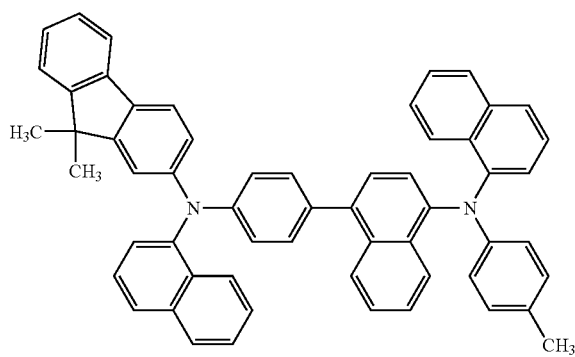
13
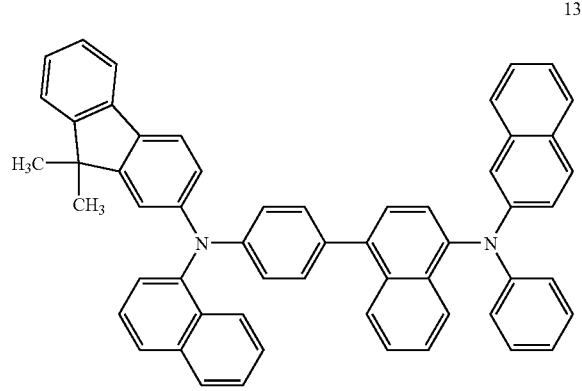
14
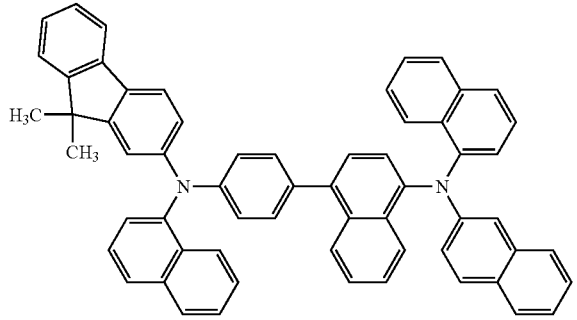
15
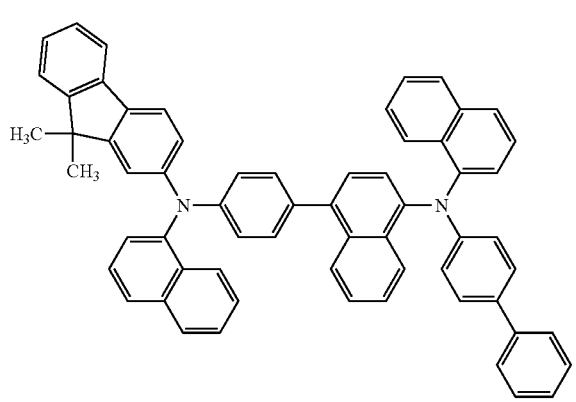
16
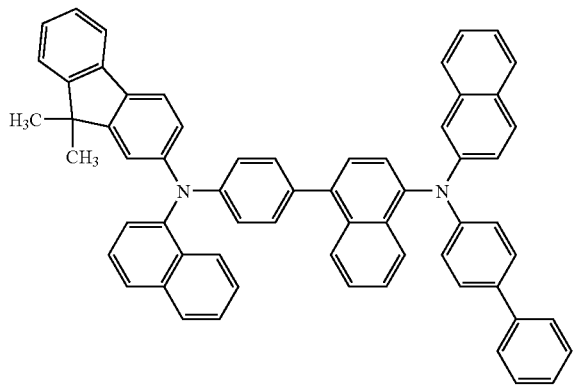
17
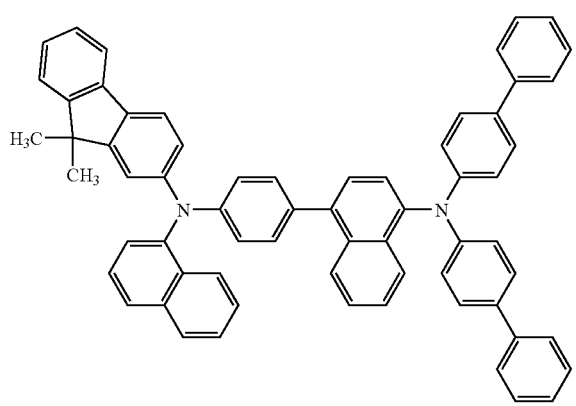

18
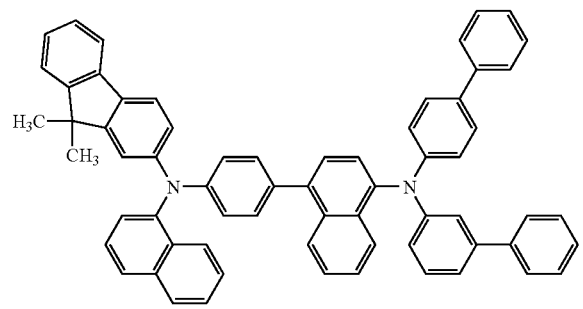
19
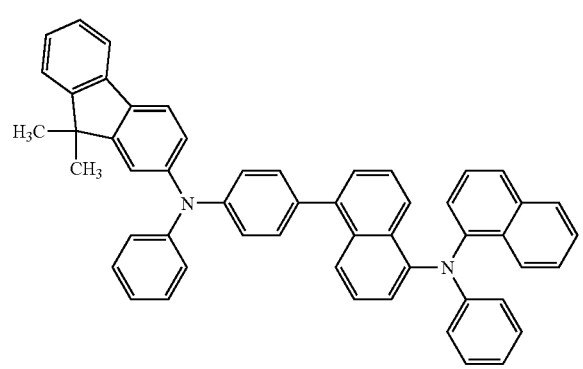
20
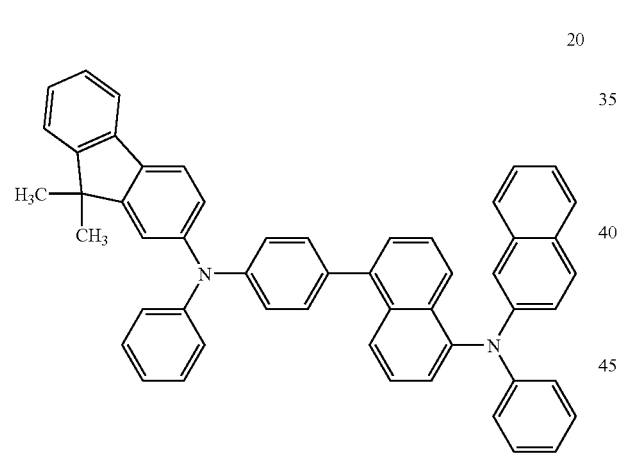
21
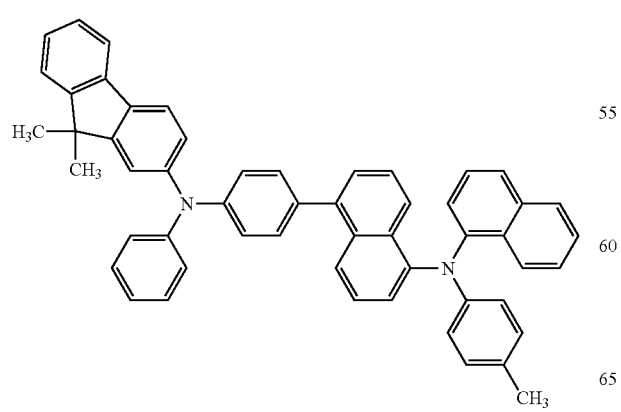
22
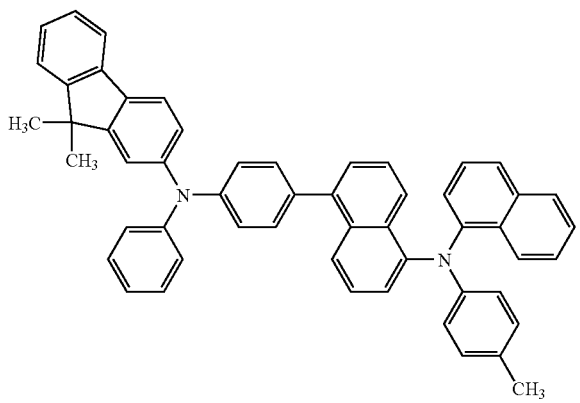
23
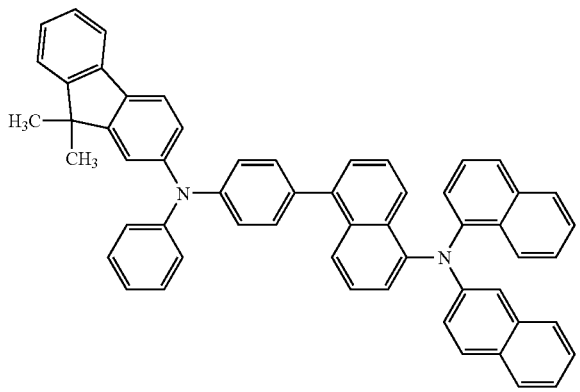
24
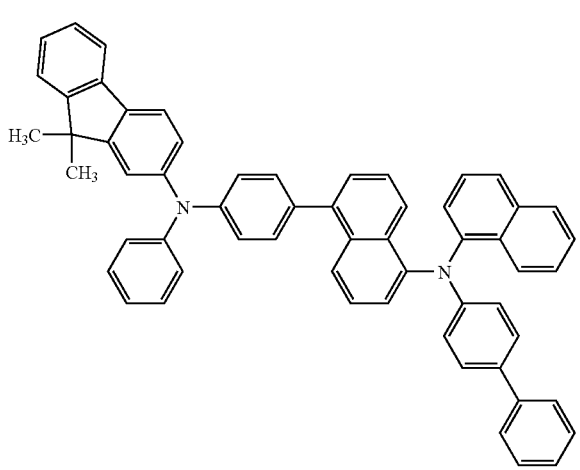

25
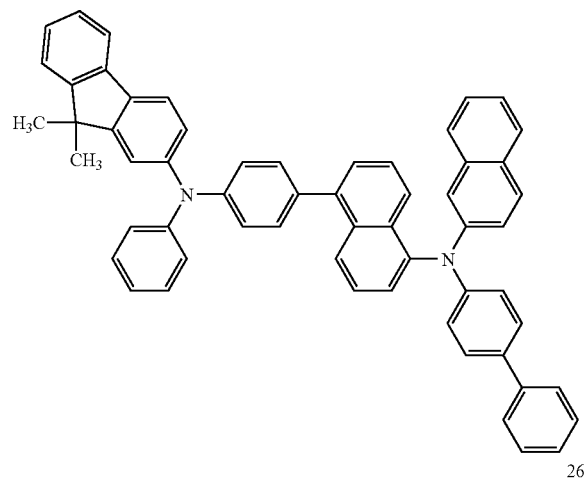
26
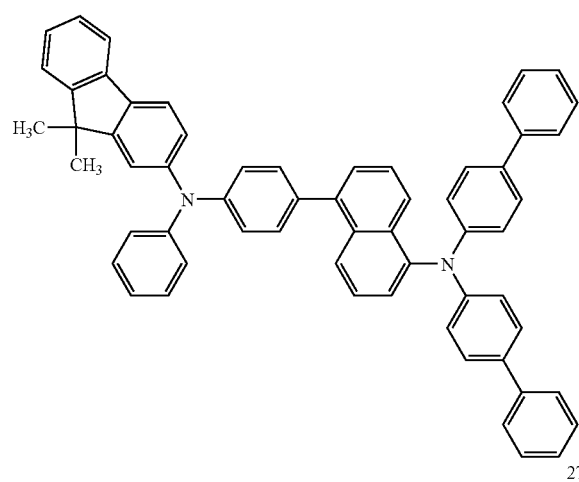
27
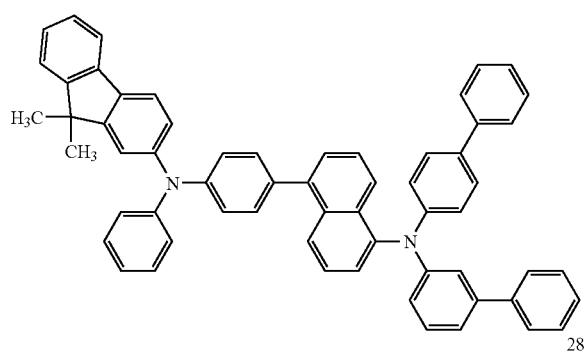
28
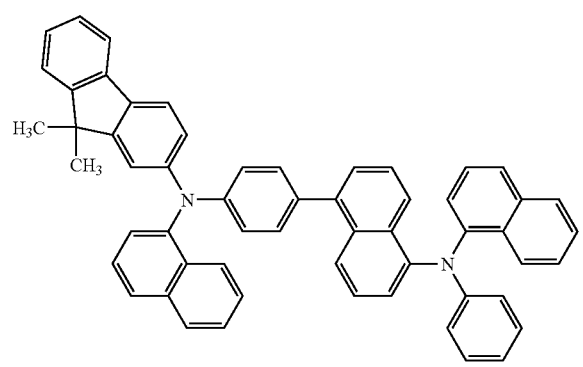
29
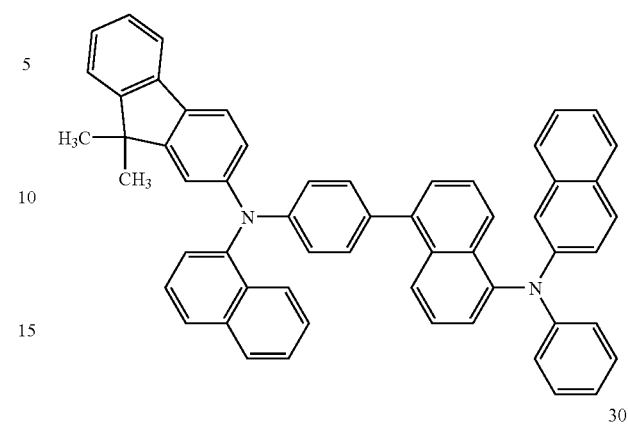
30
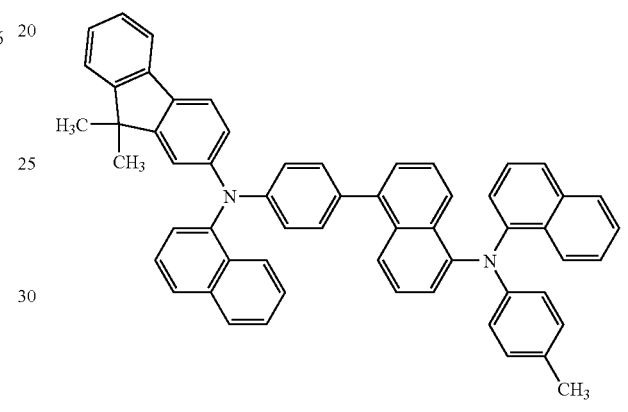
31
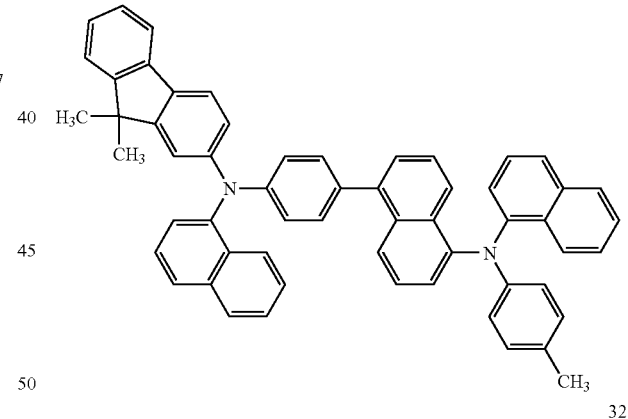
32
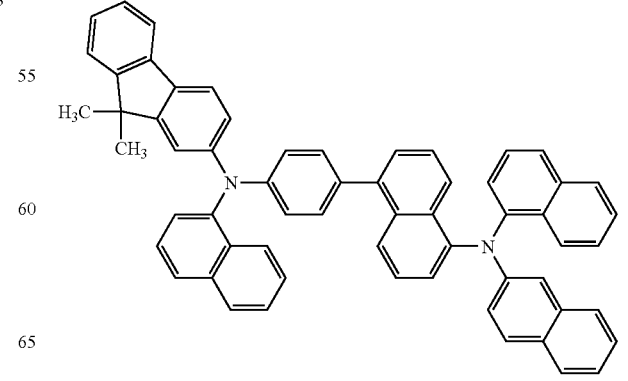

33
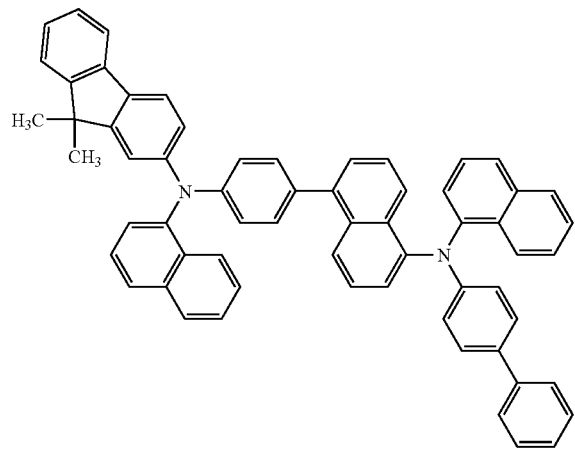
34
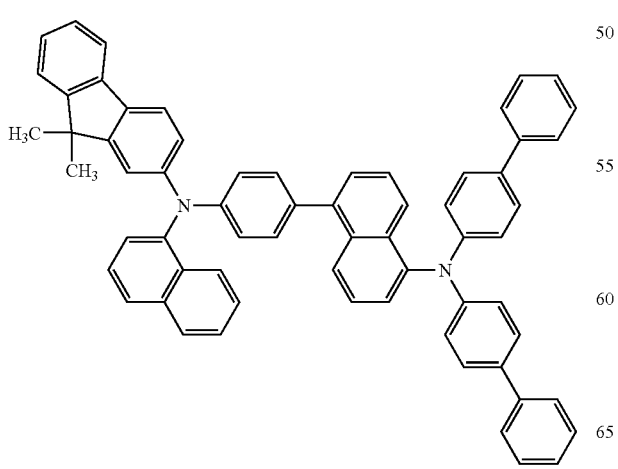
35
36
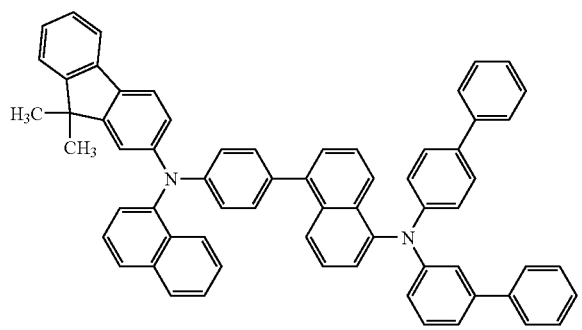
37
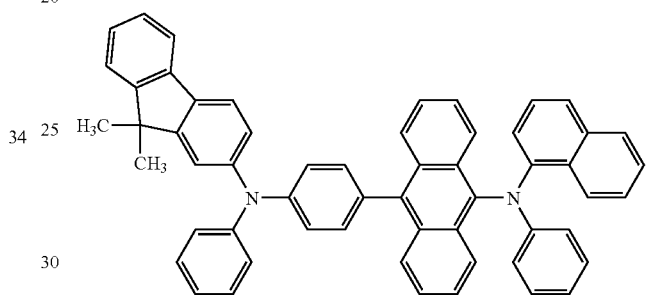
38
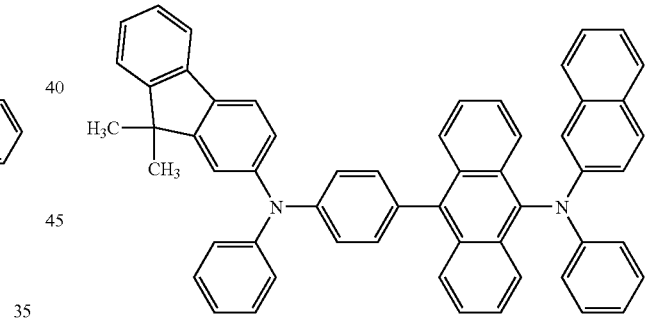
39

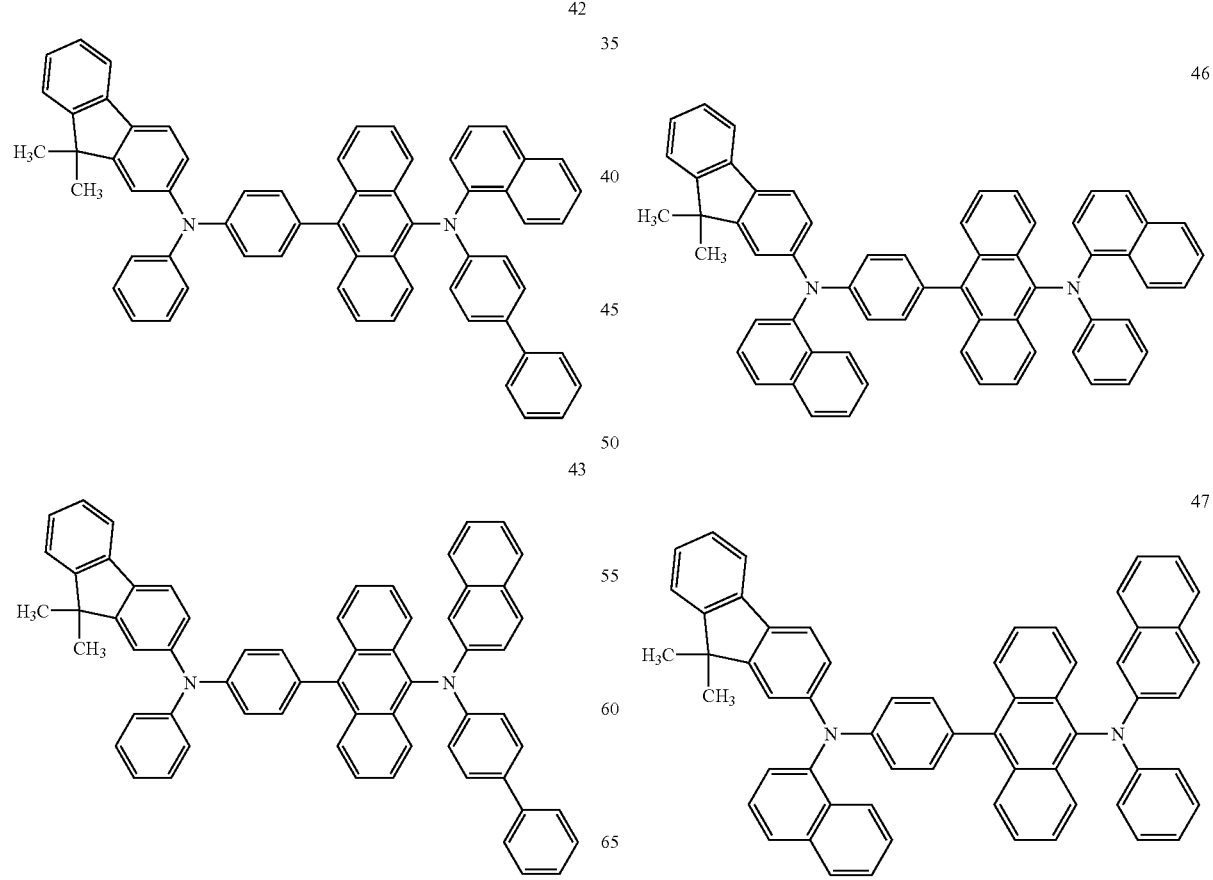

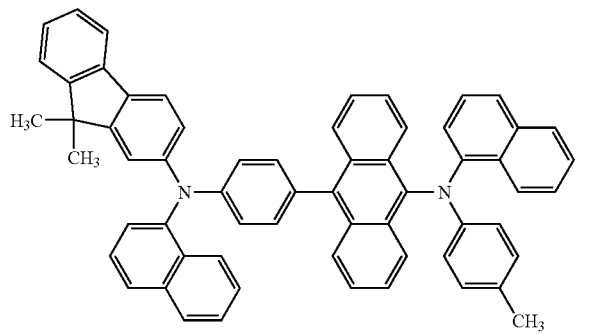
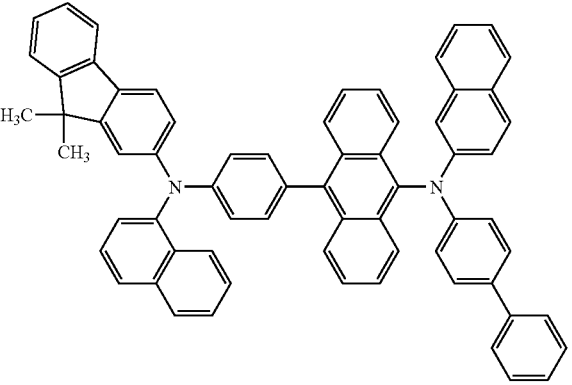
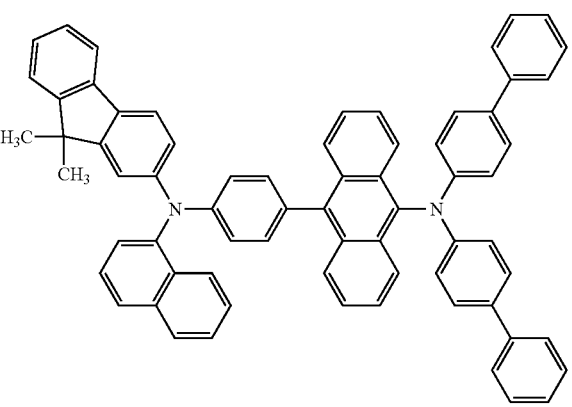
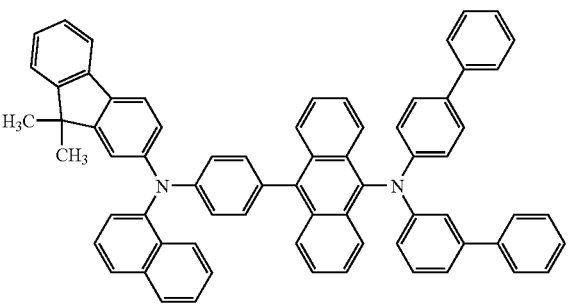
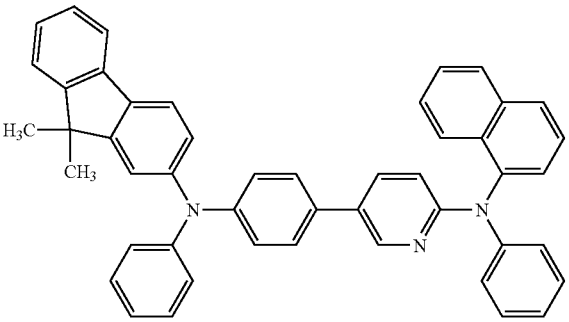

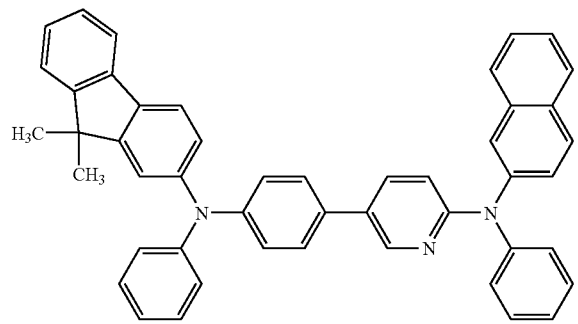
56
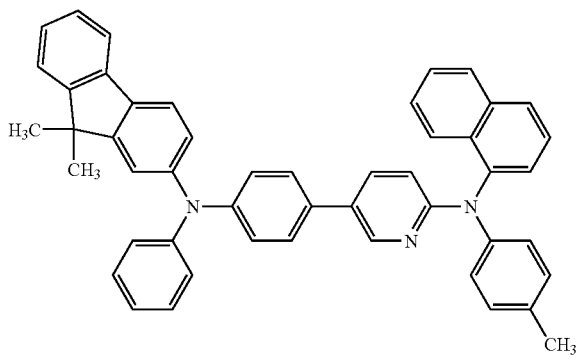
57
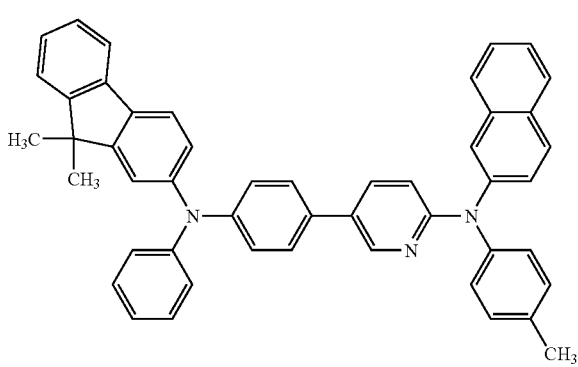
58
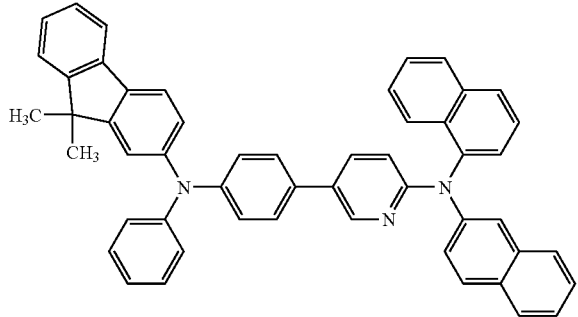
59
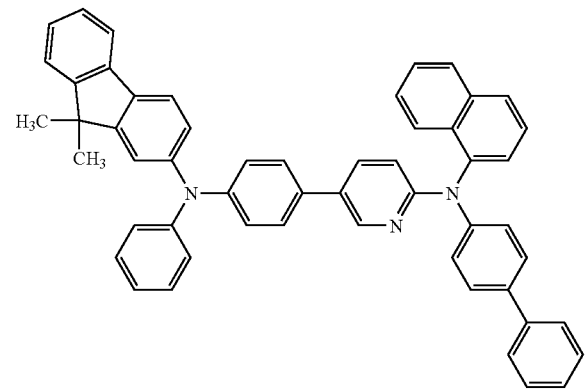
60
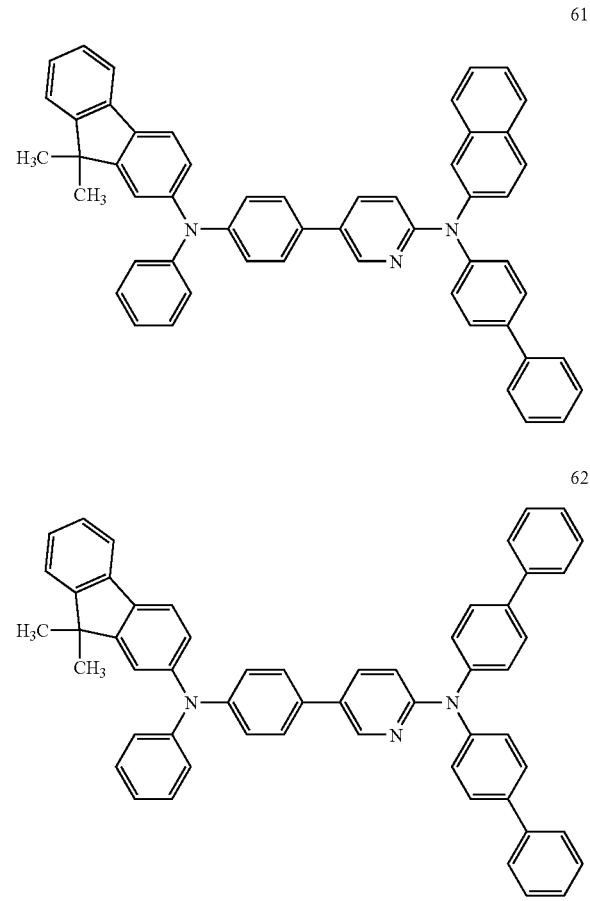
61
62
63

64
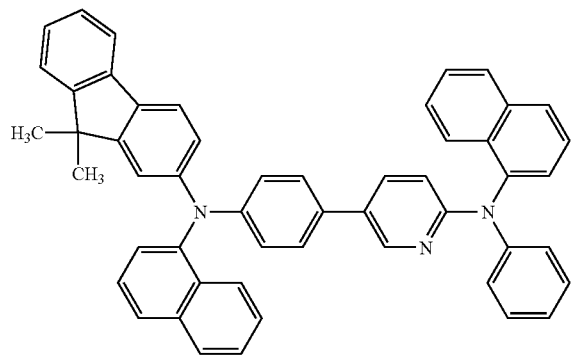
65
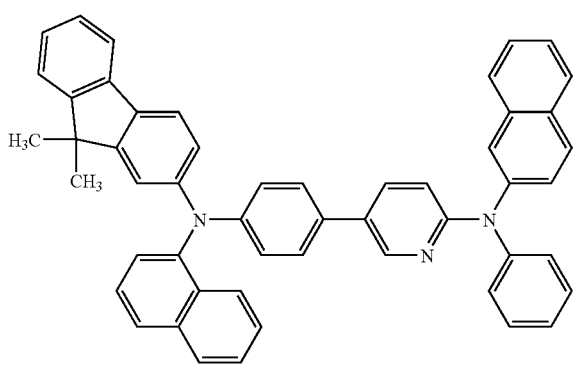
66
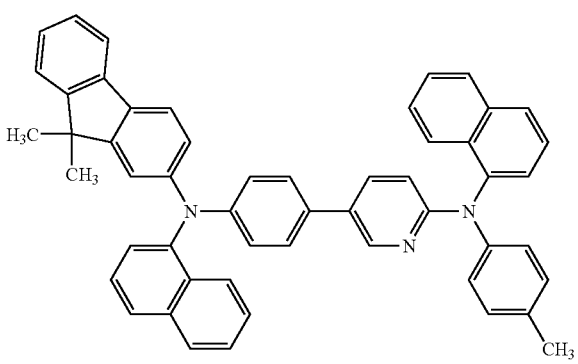
67
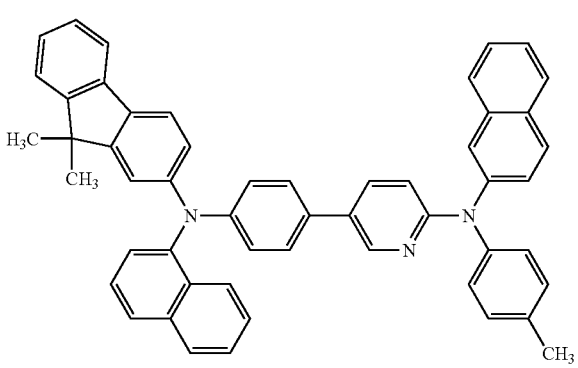
68
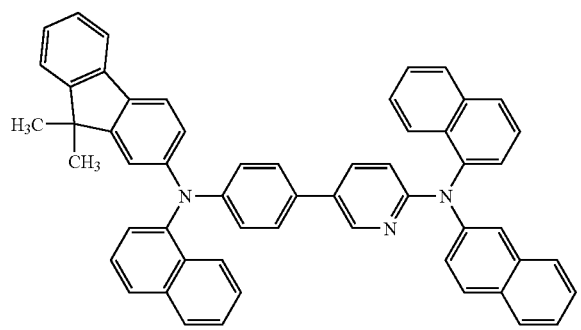
69
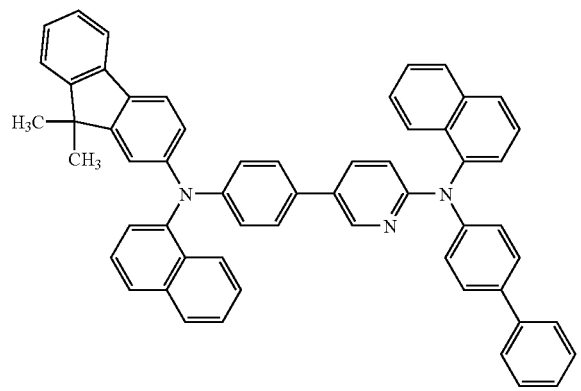
70
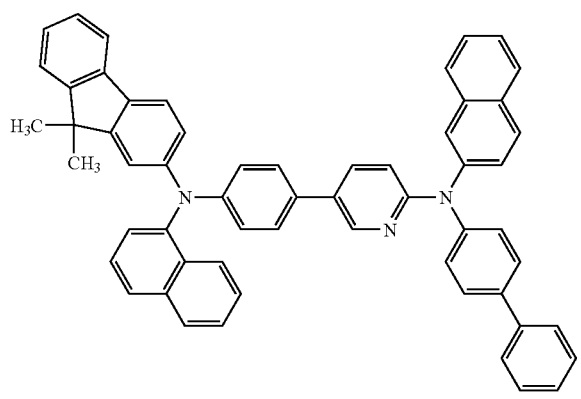
71
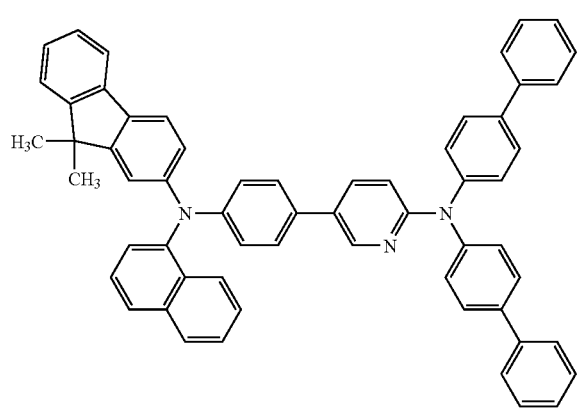

72
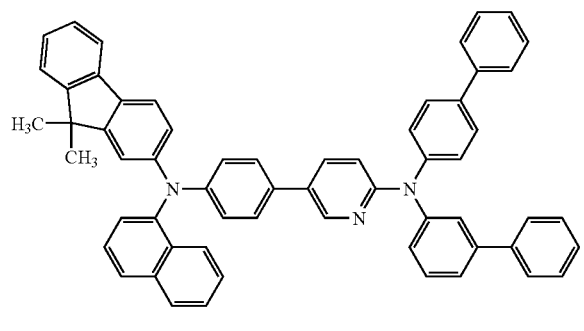
73
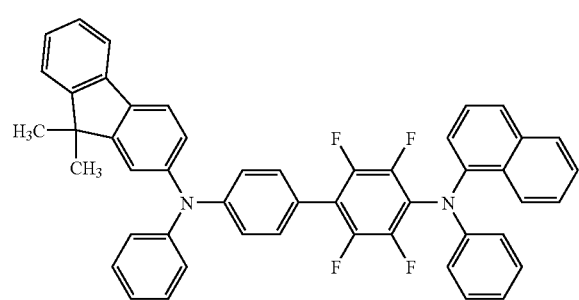
74
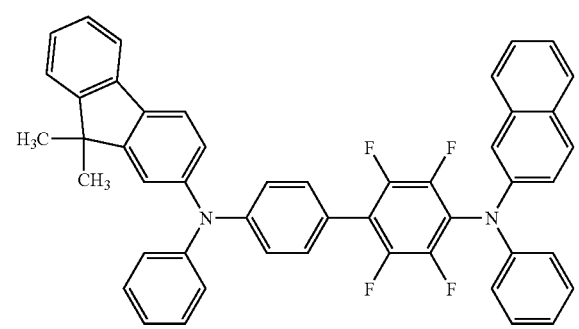
75
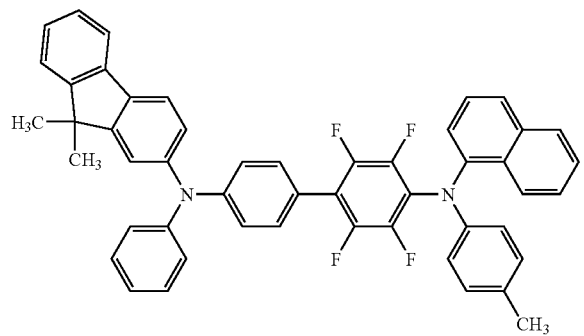
76
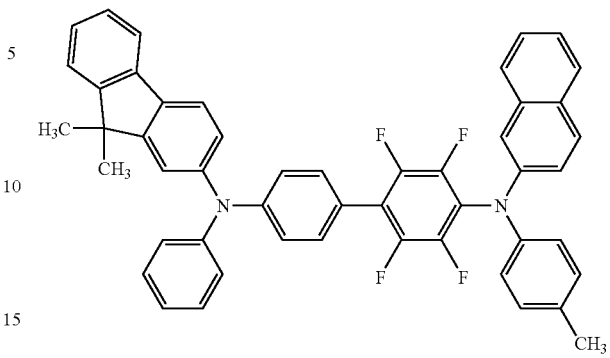
77
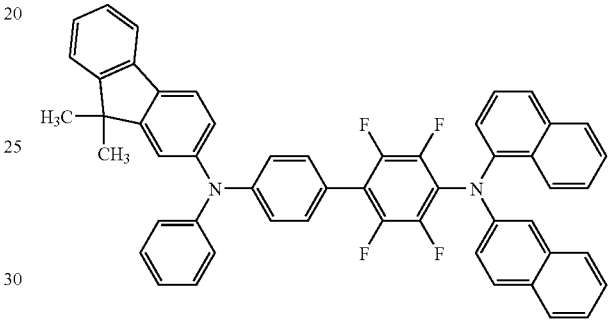
78
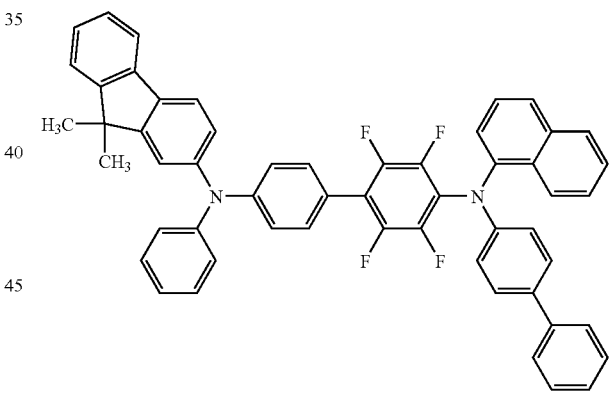
79
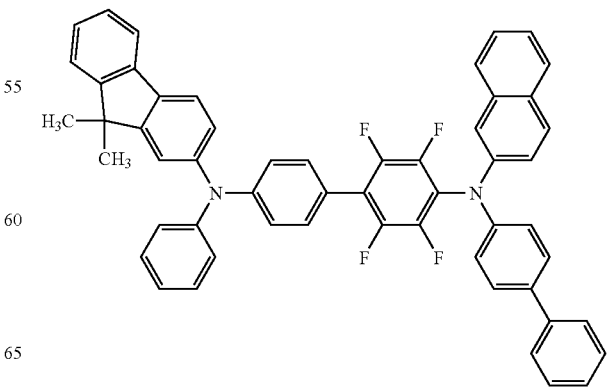

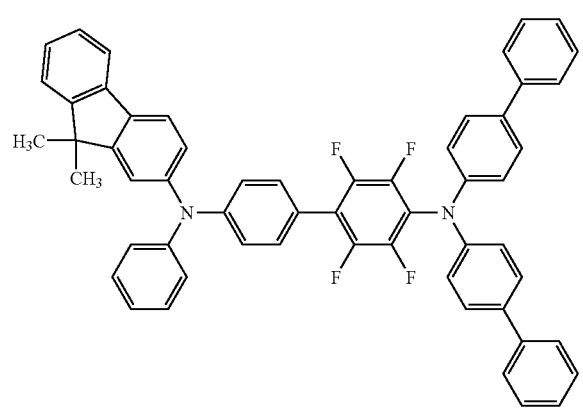
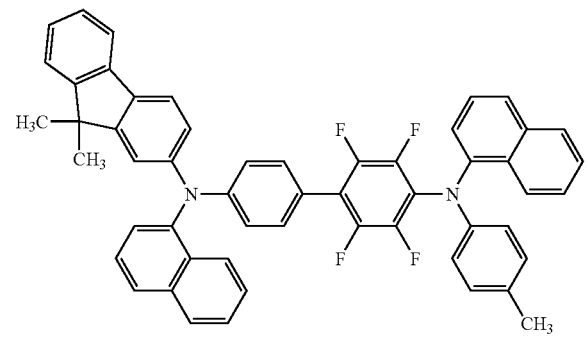
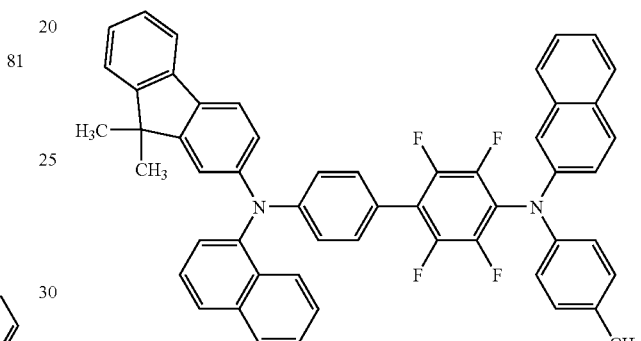
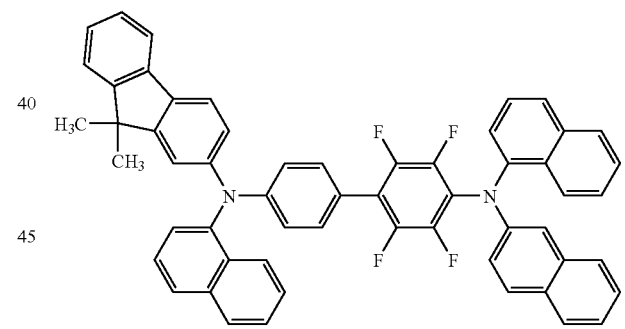
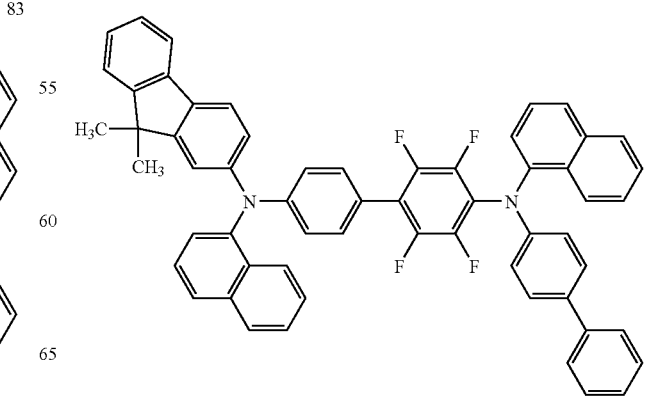

-continued
88
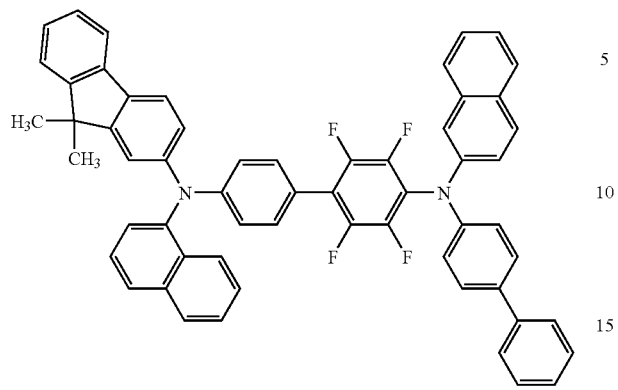
89
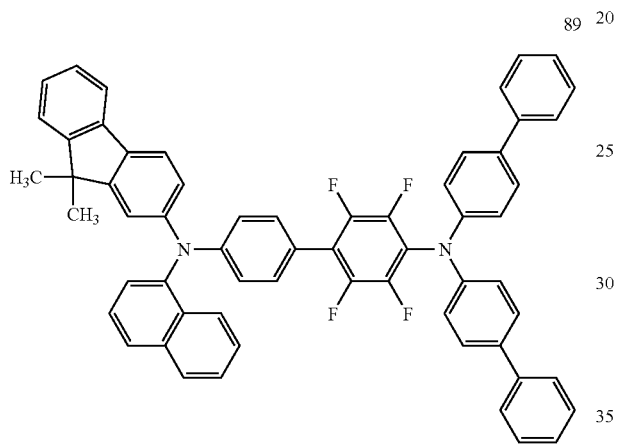
90
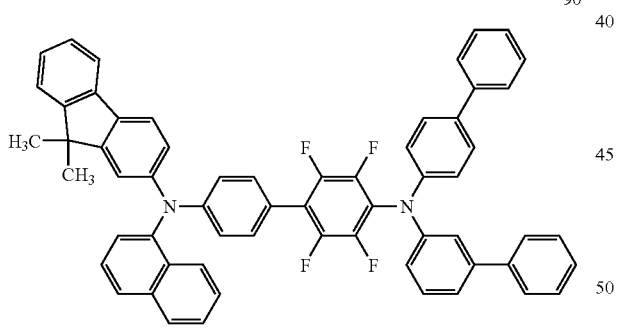
91
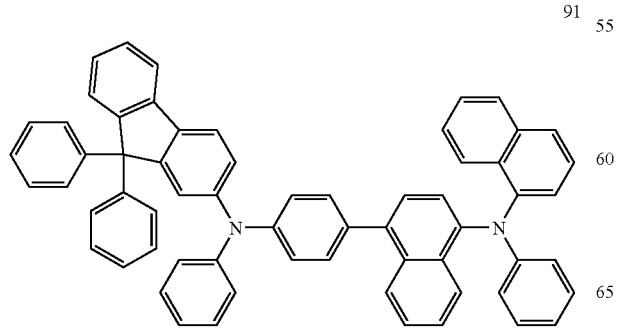
-continued
92
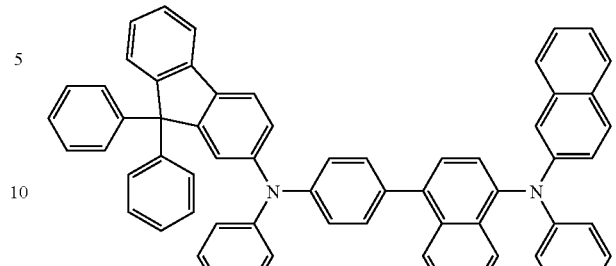
93
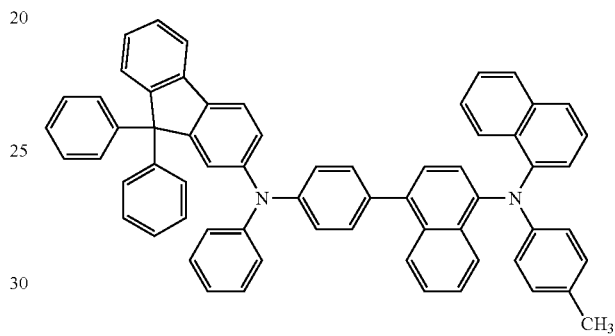
94
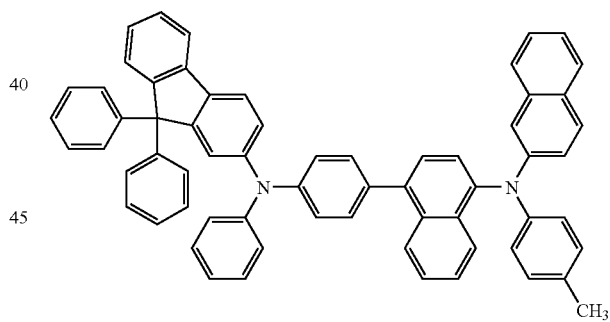
95
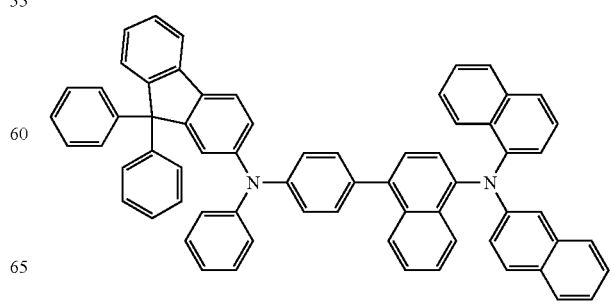

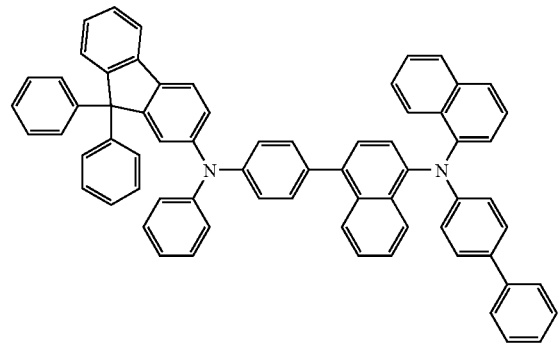
96
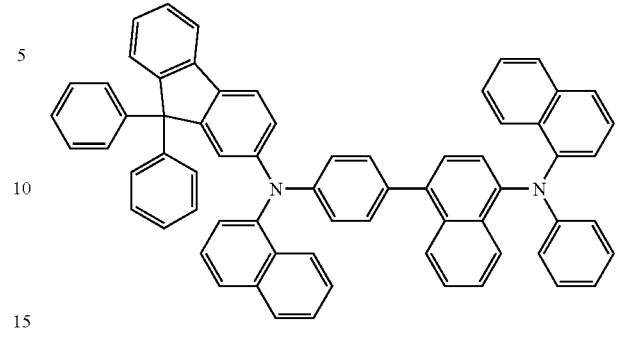
100
97
101
98
102
99
103

-continued
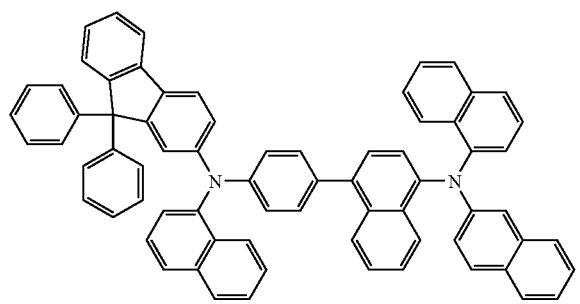
104
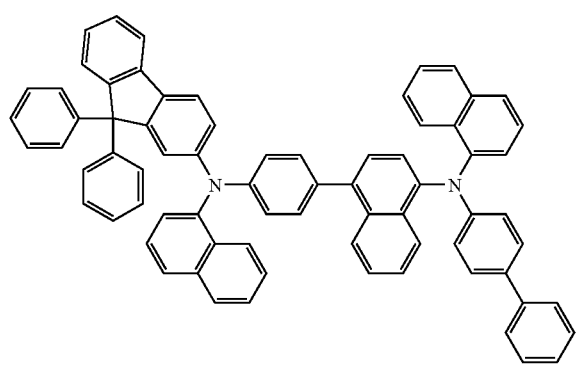
105
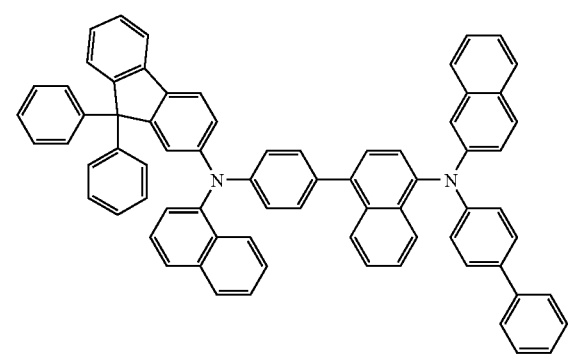
106
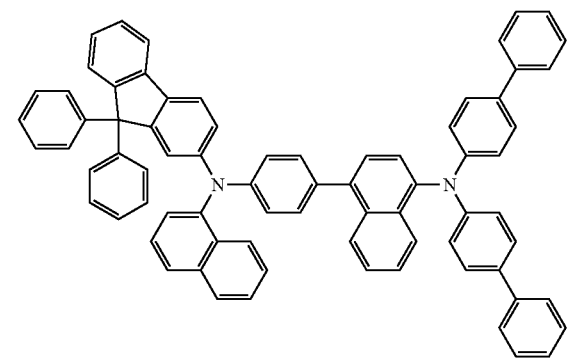
107
-continued
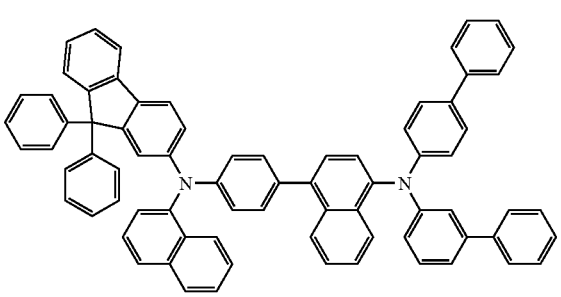
108
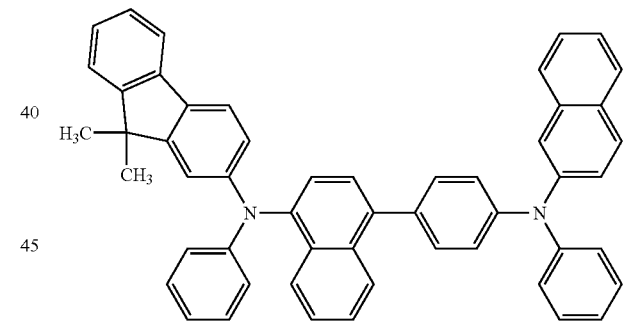
109
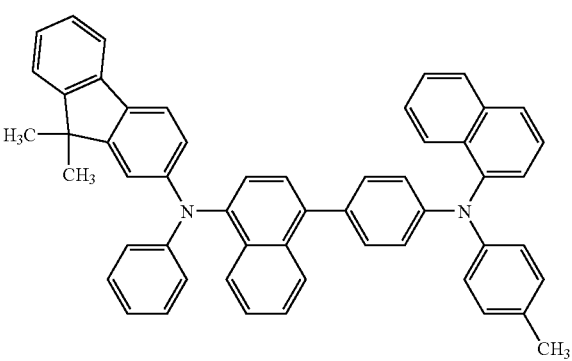
110
111

-continued
112
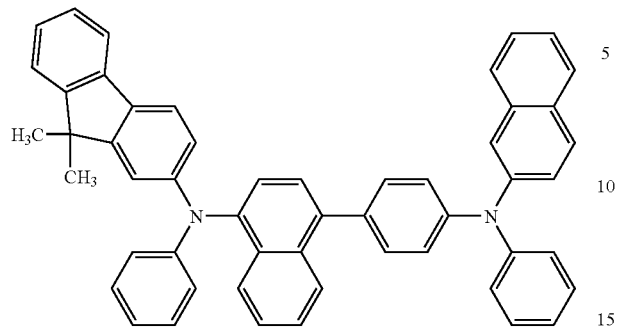
113
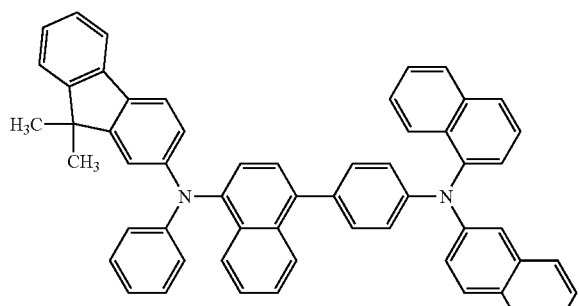
114
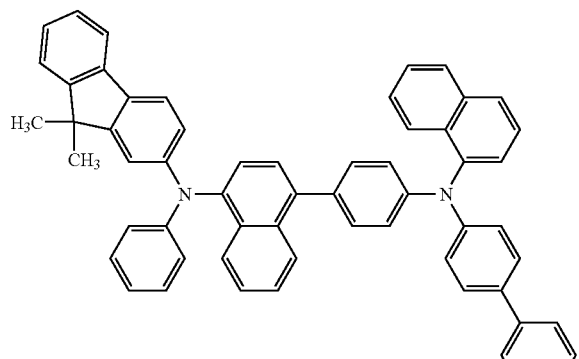
115
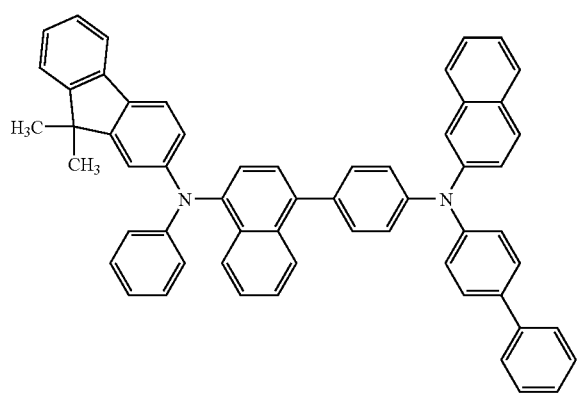
116
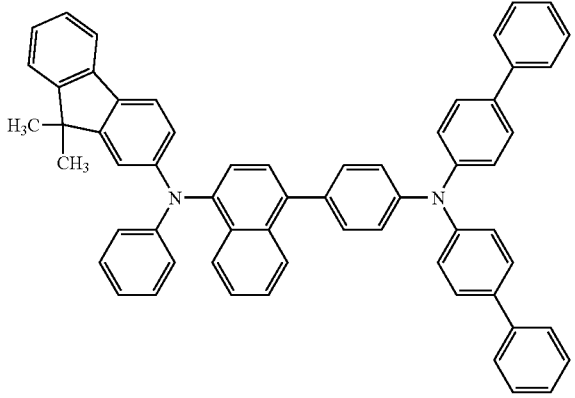
117
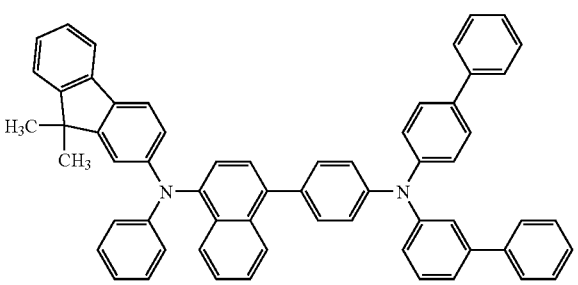
118
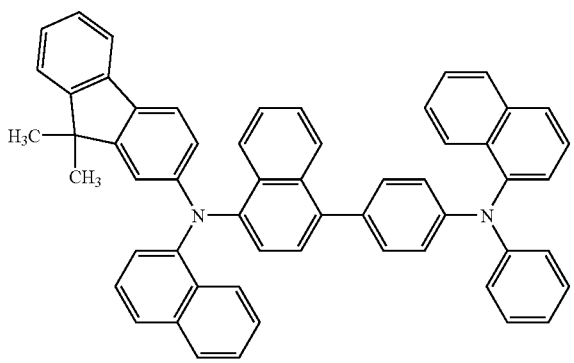
119
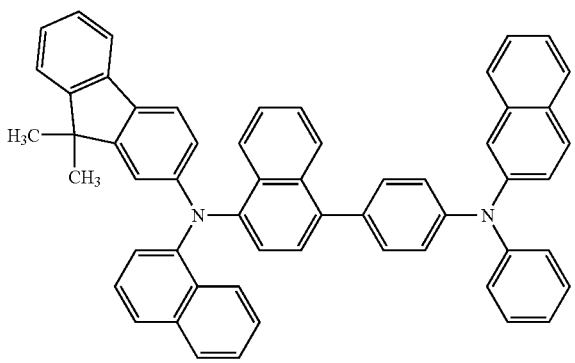

-continued
120
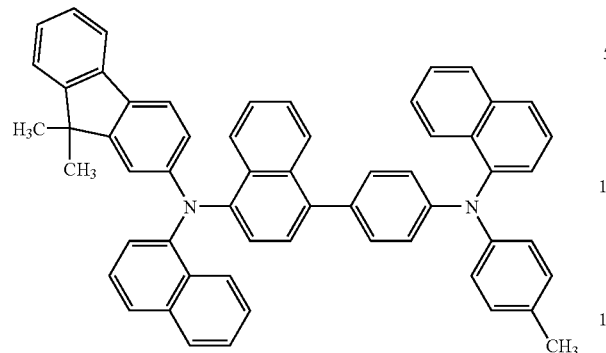
121
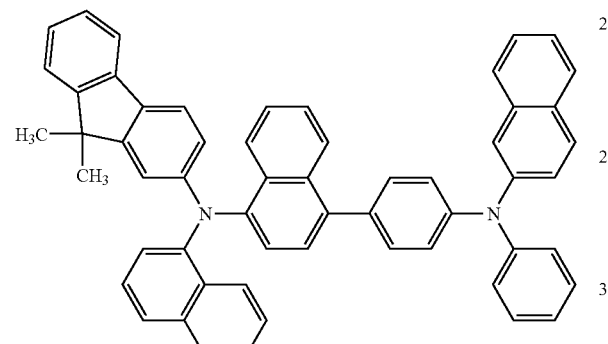
122
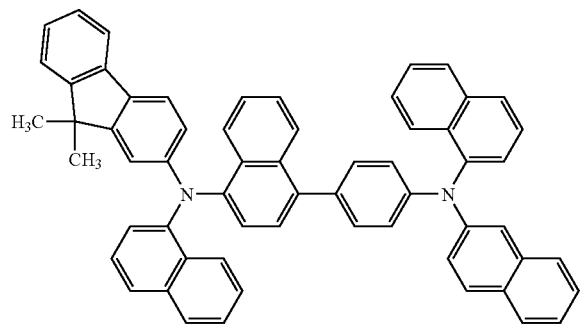
123
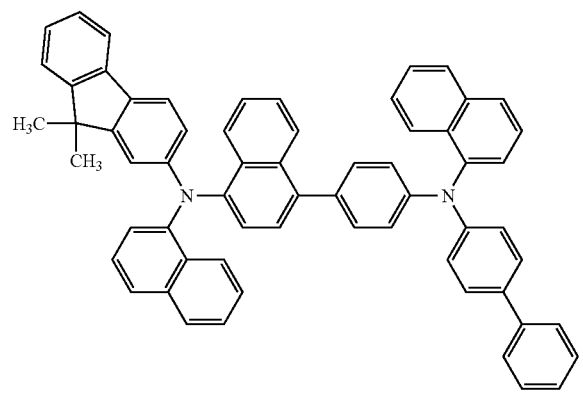
-continued
124
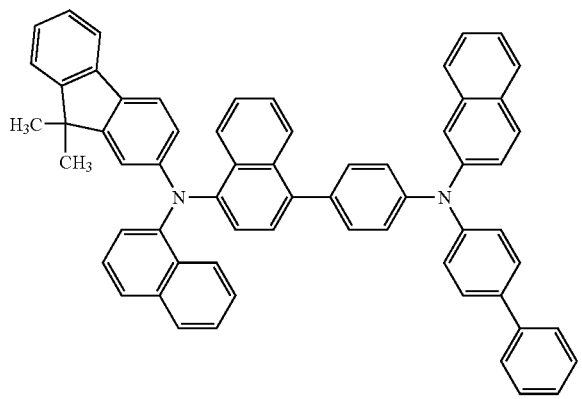
125
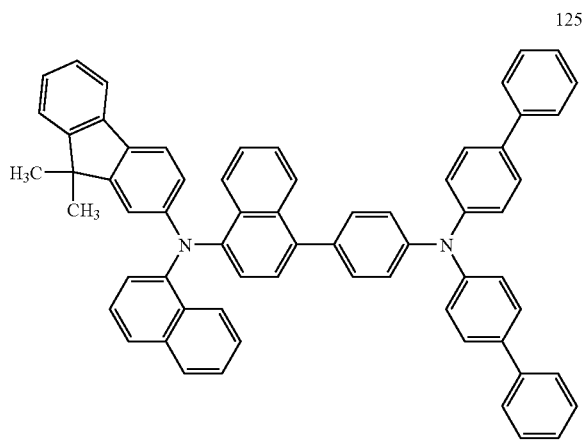
126
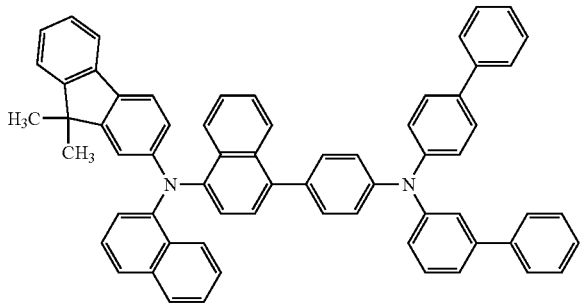
127
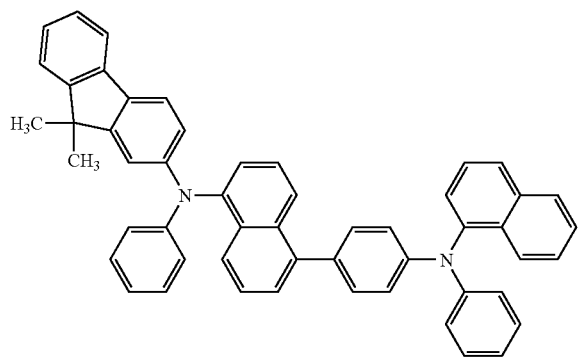

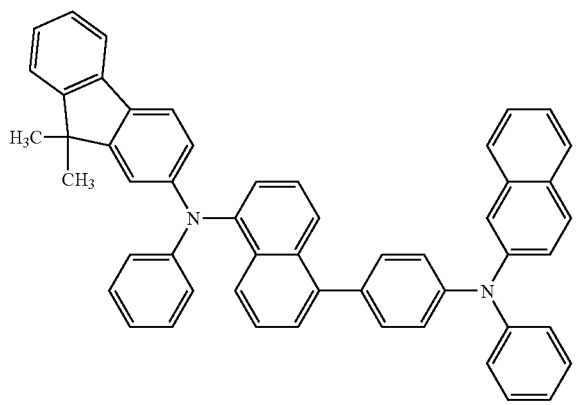
128
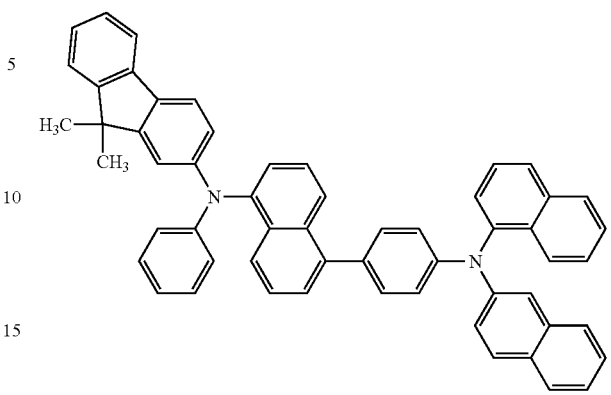
131
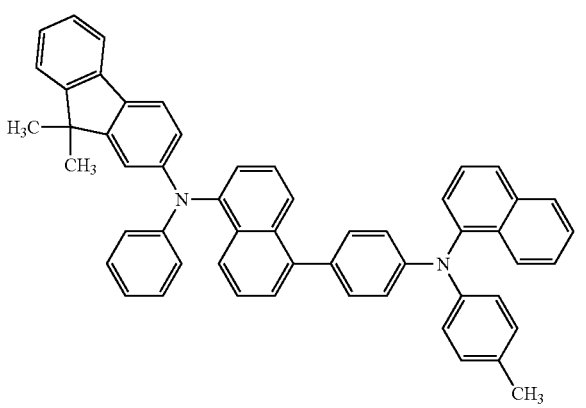
129
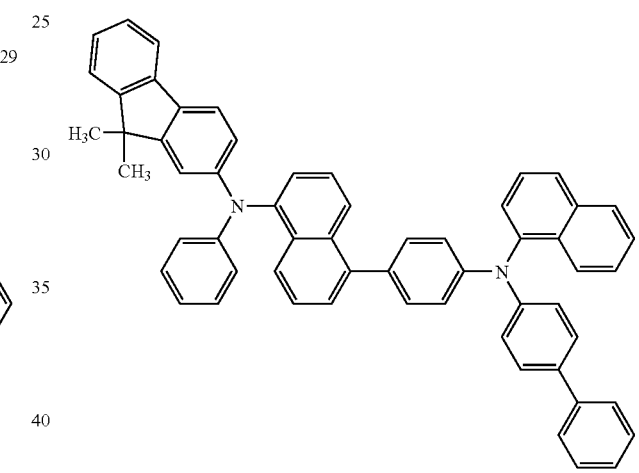
132
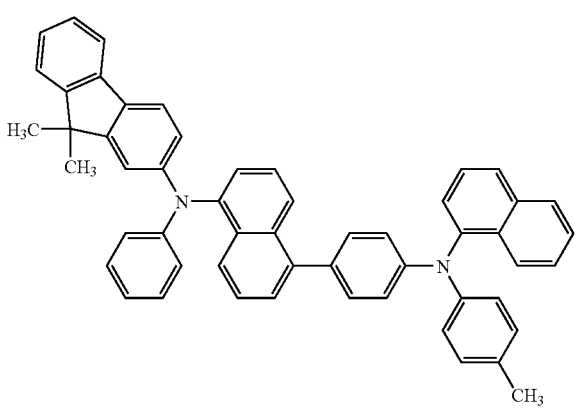
130
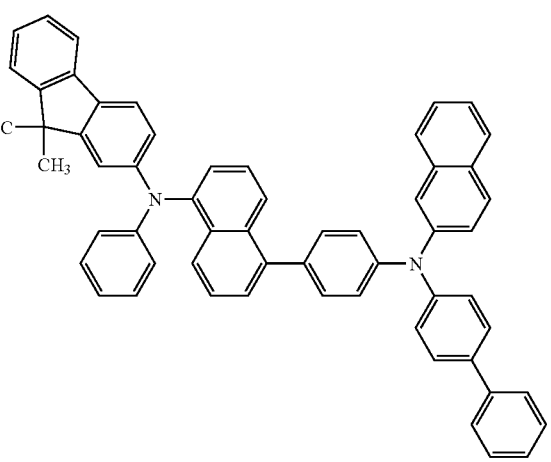
133

134
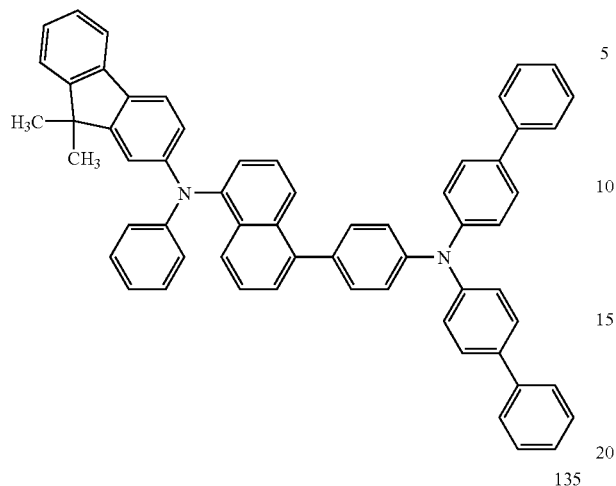
135
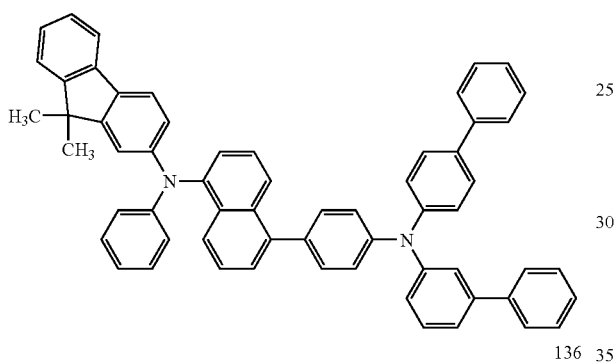
136
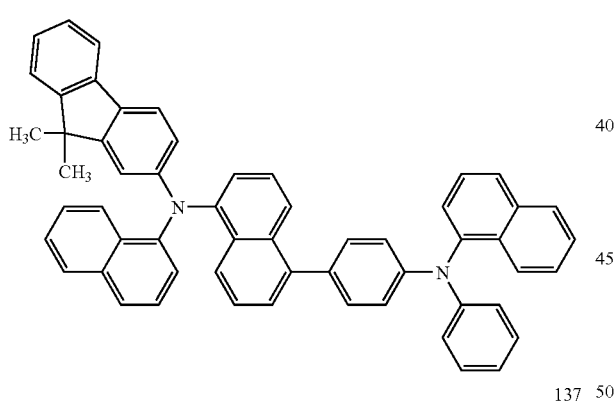
137
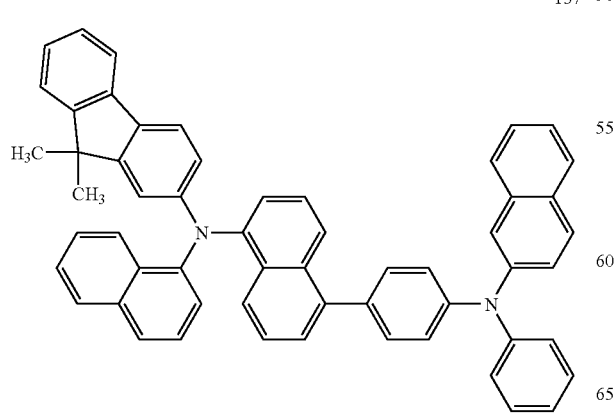
138
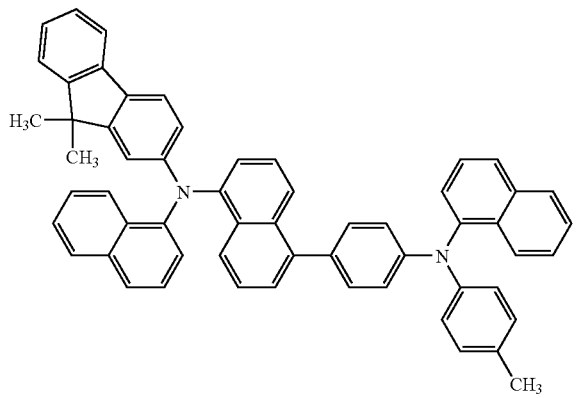
139
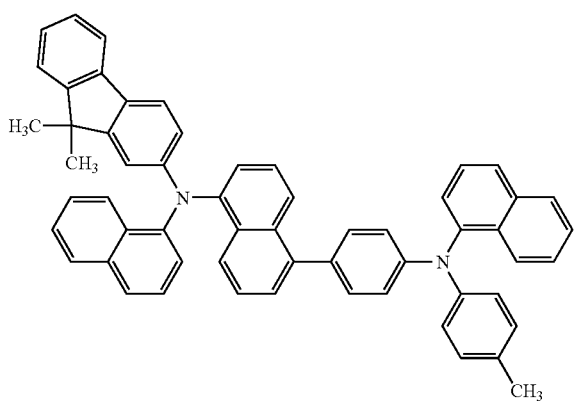
140
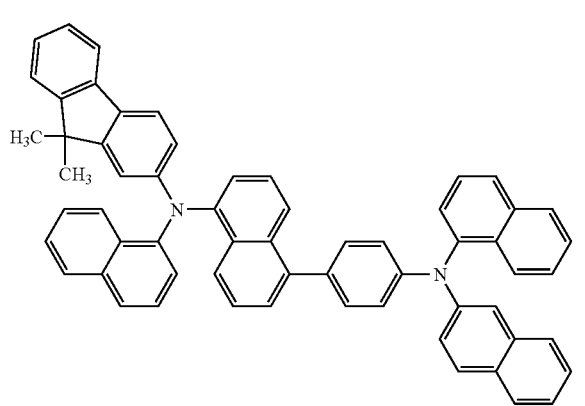

141
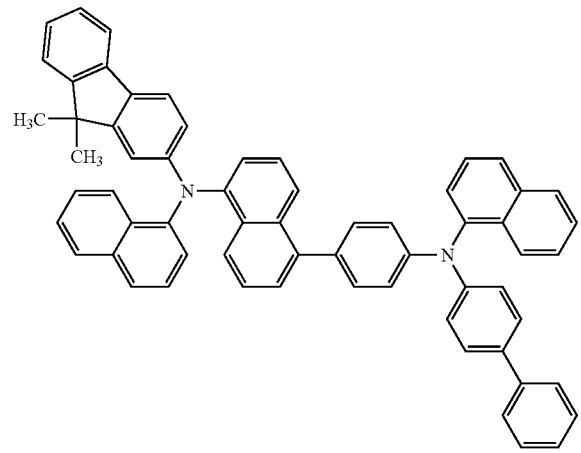
142
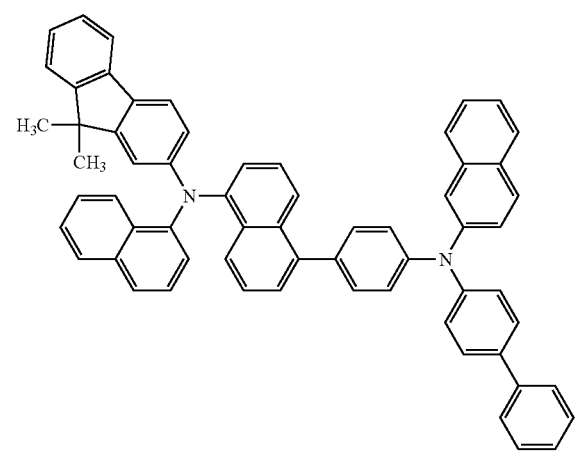
143
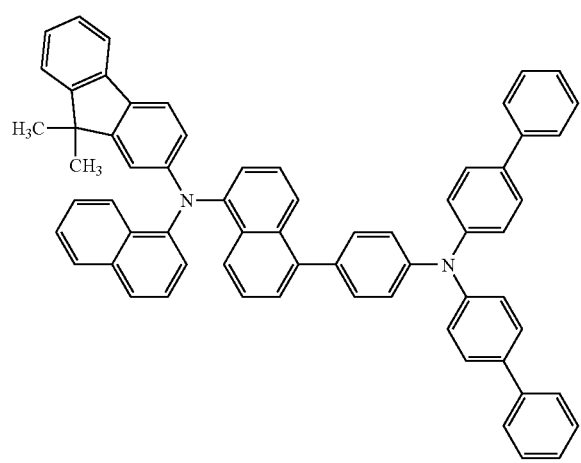
144
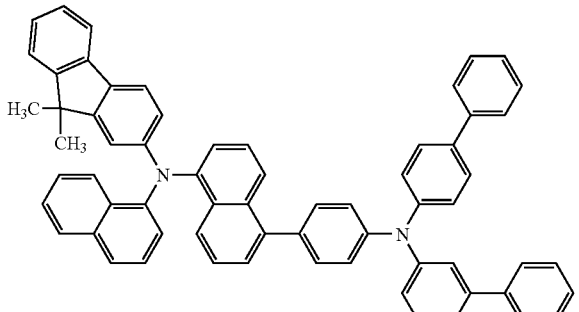
145
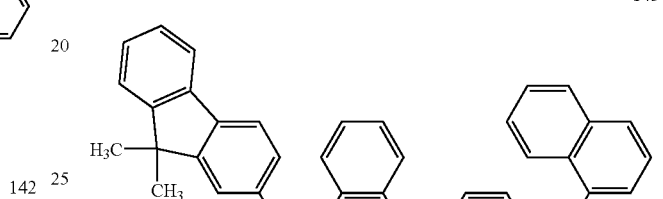
146
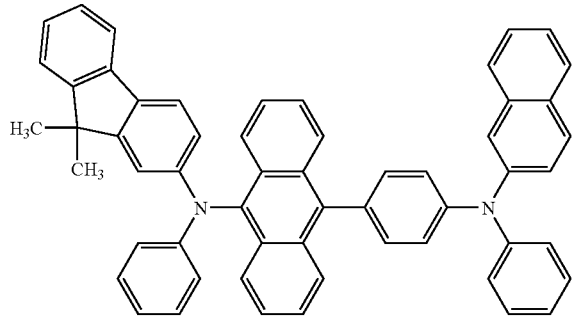
147
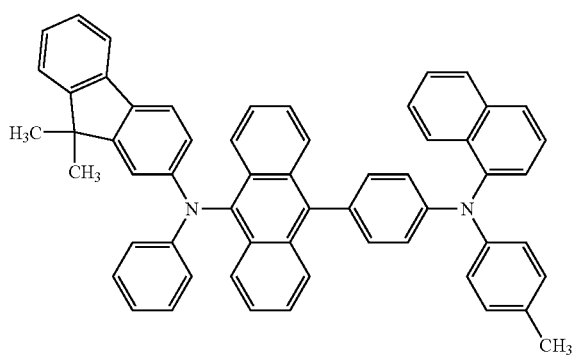

148
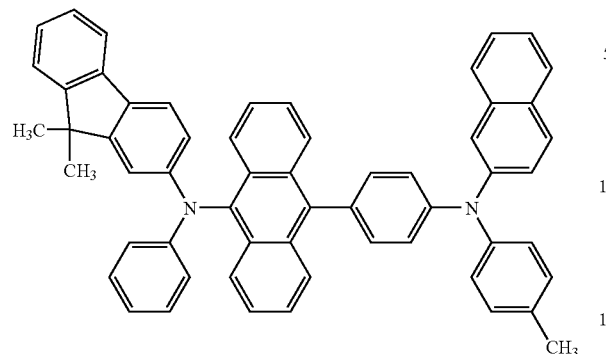
149
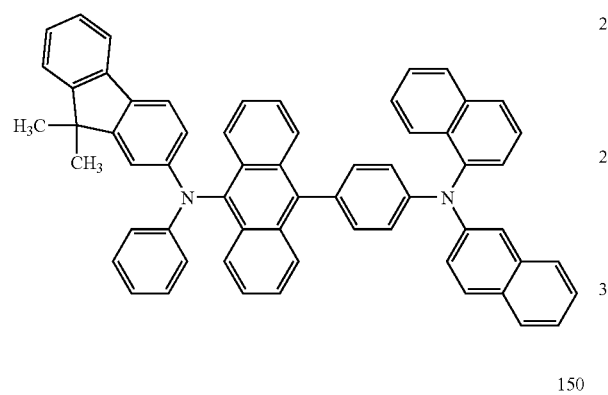
150
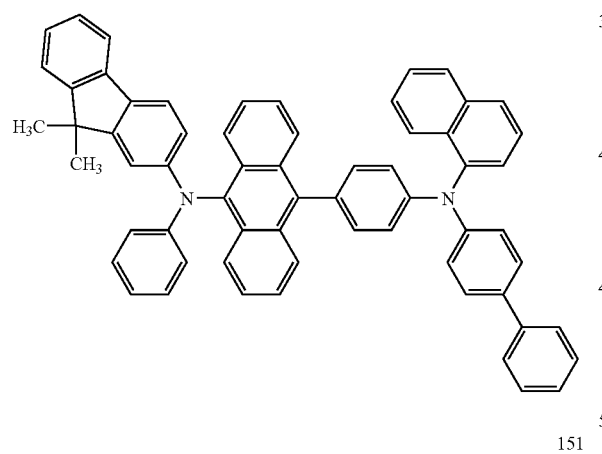
151
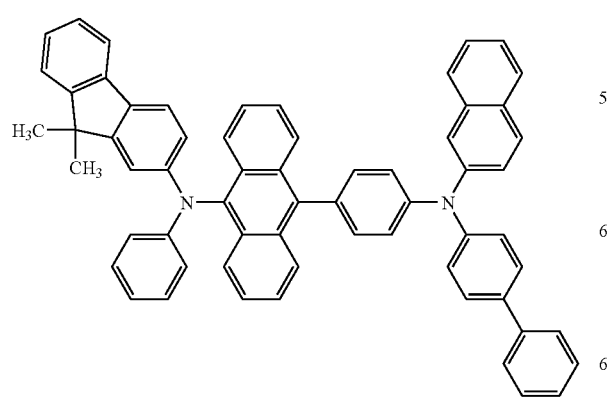
152
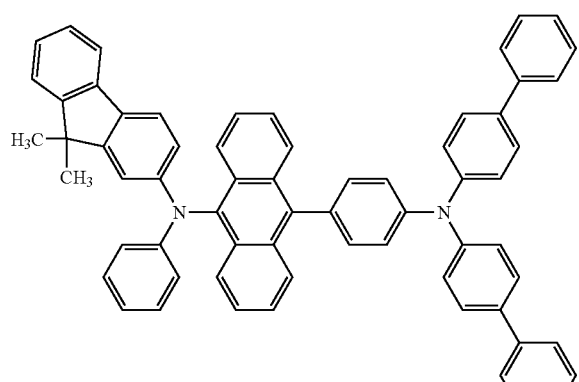
153
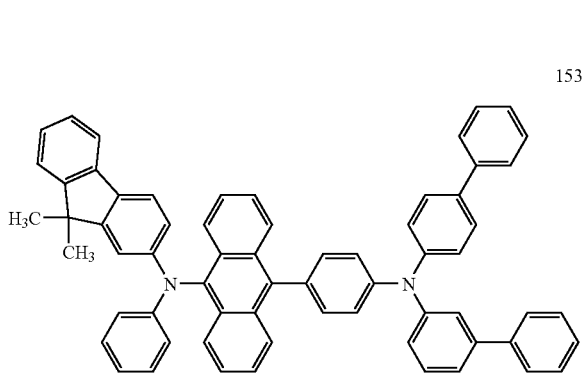
154
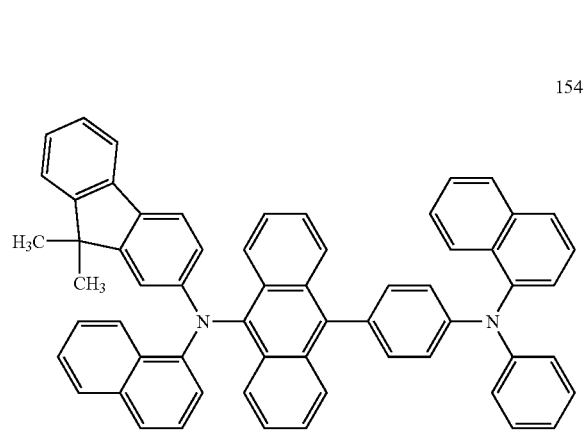
155
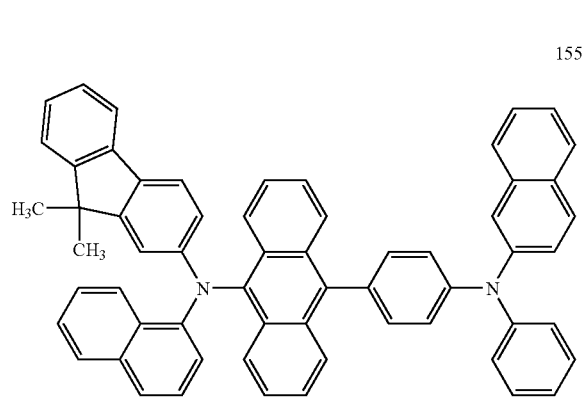

156
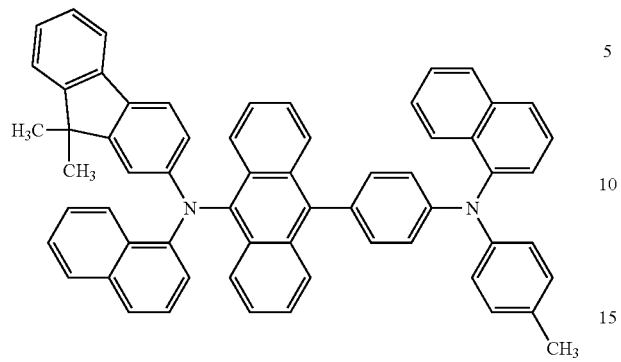
157
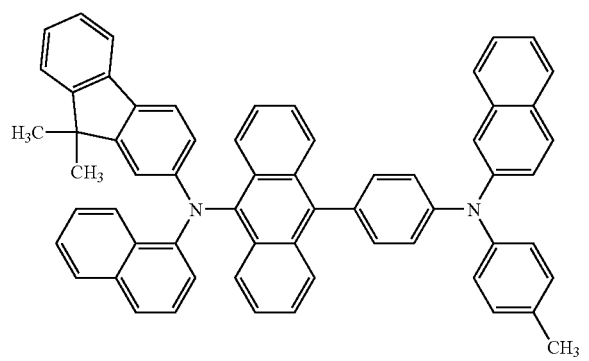
158
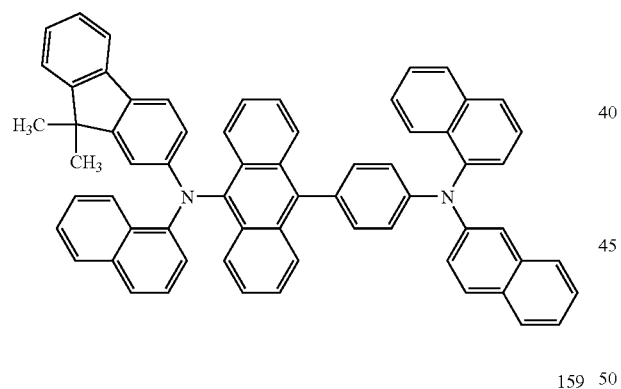
159
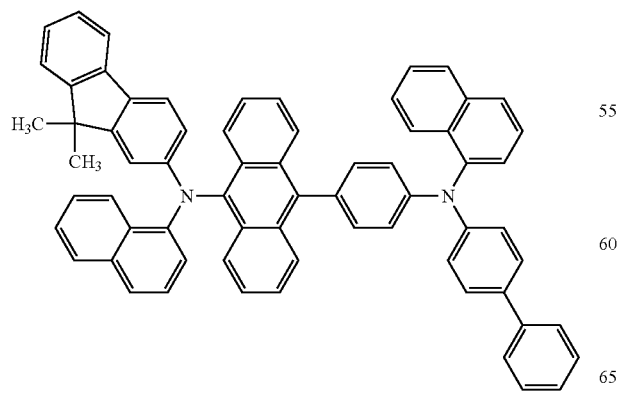
160
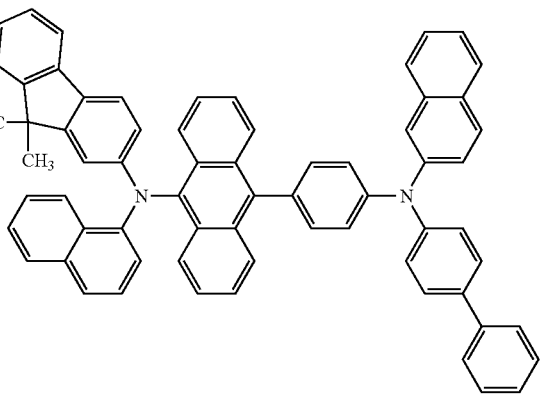
161
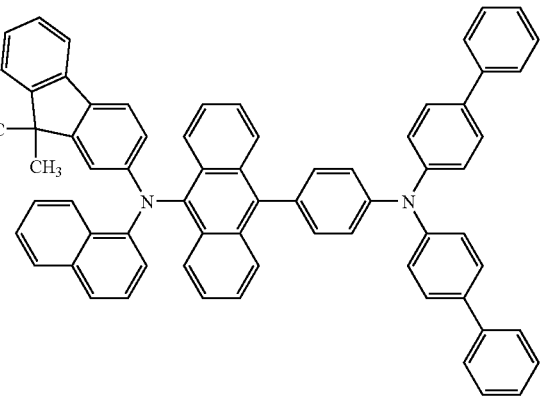
162
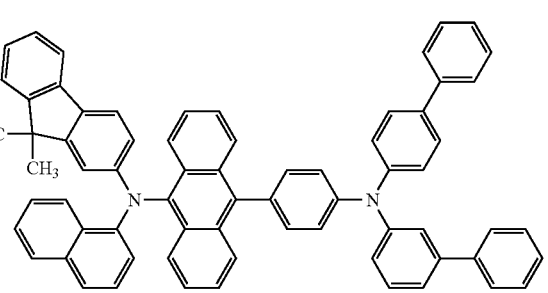
163
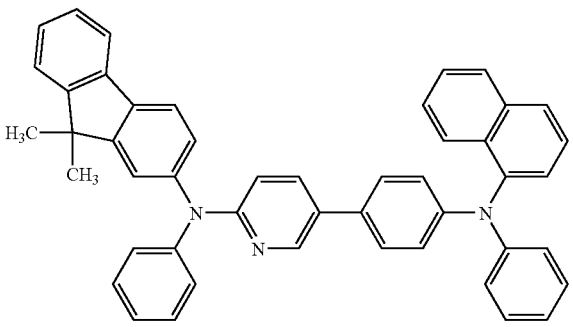

164
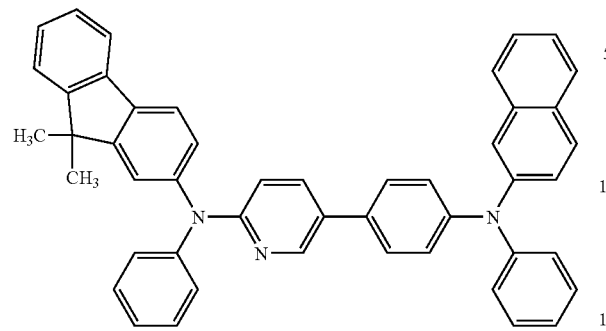
165
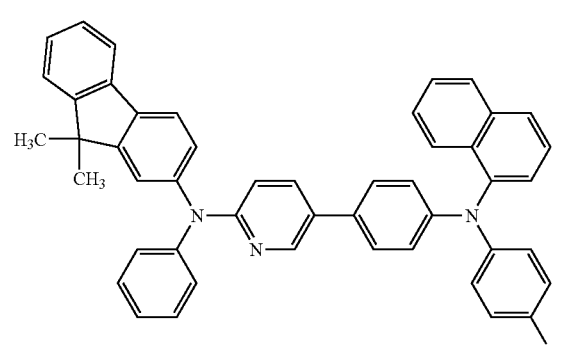
166
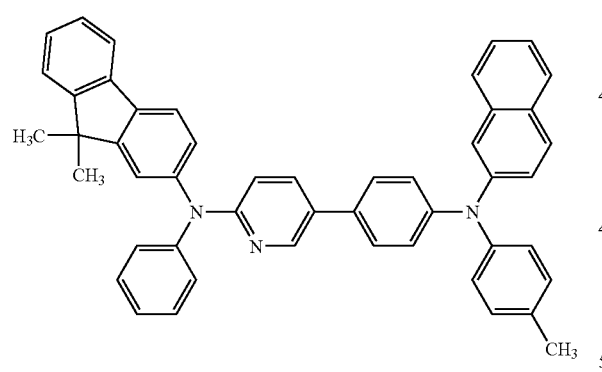
167
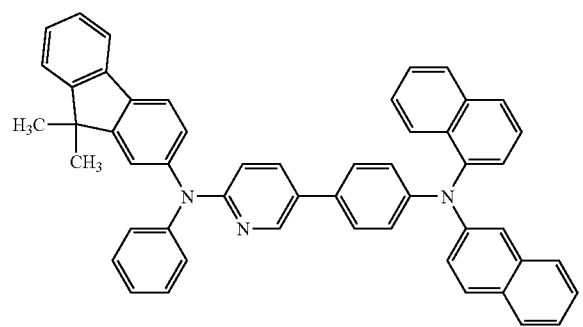
168
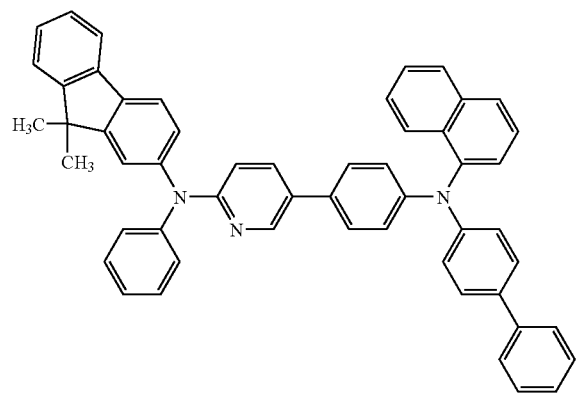
169
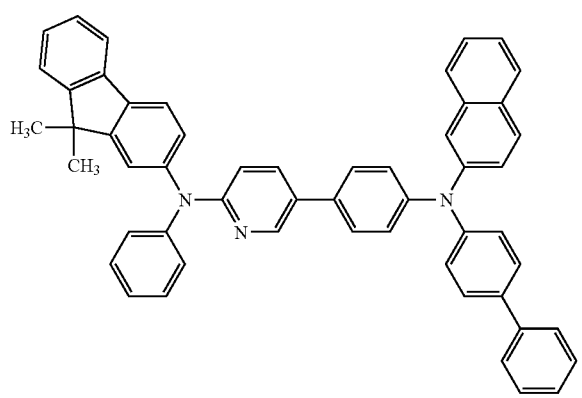
170
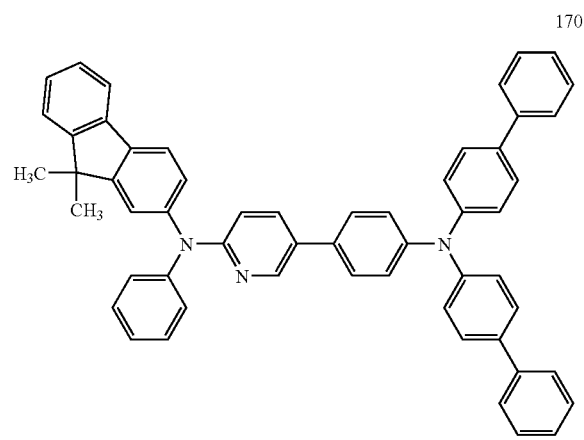
171
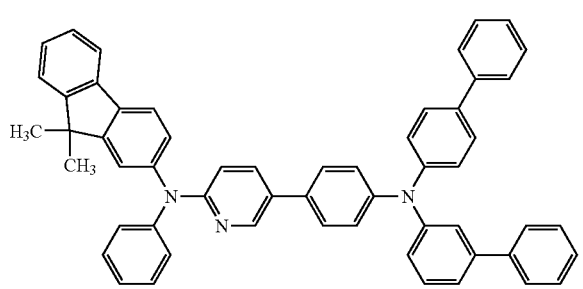

172
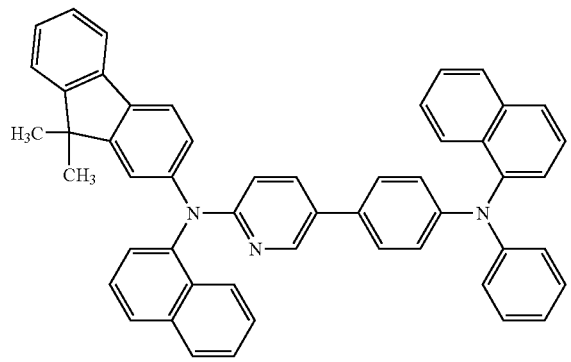
173
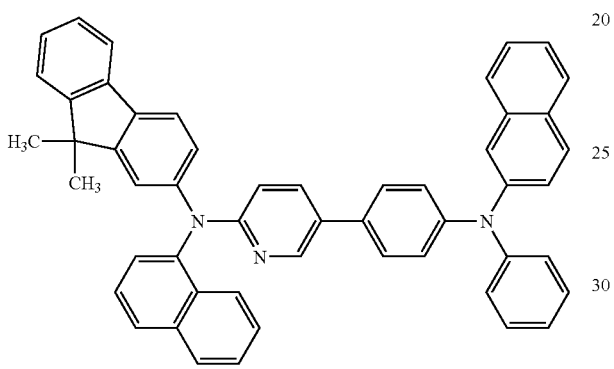
174
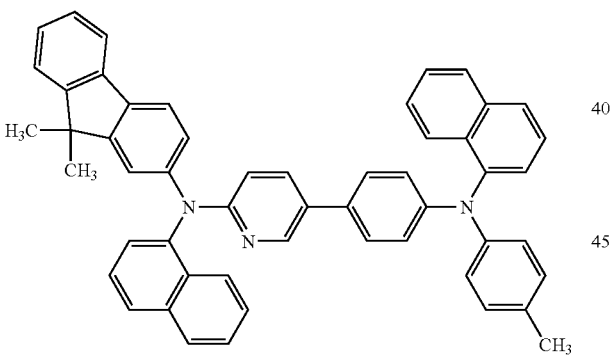
175
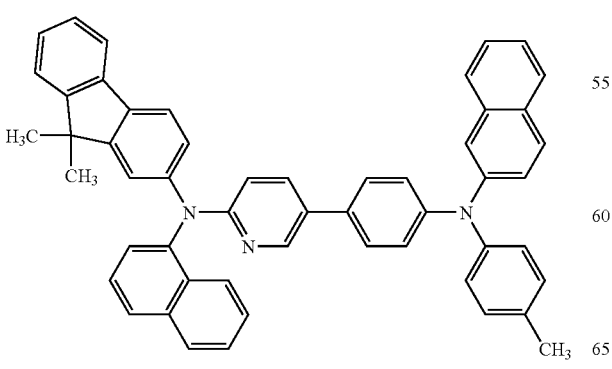
176
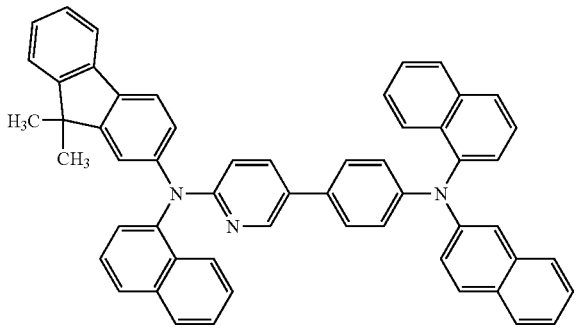
177
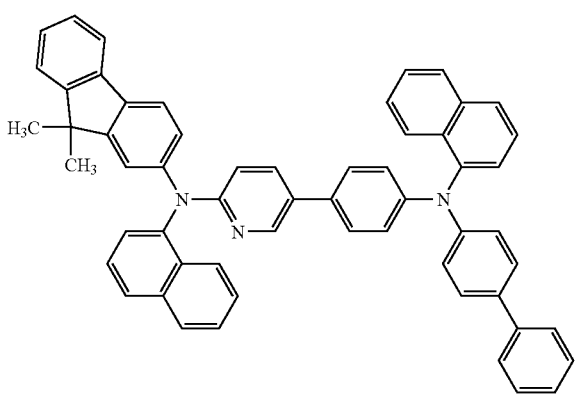
178
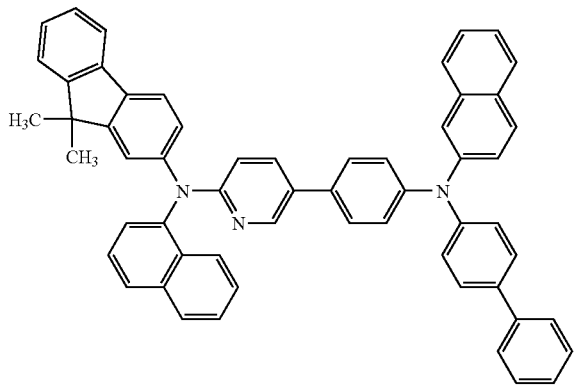
179
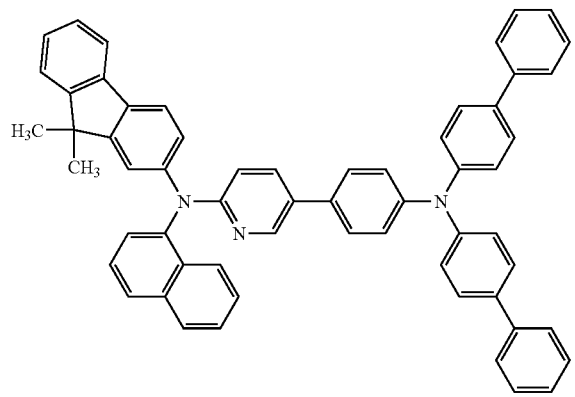

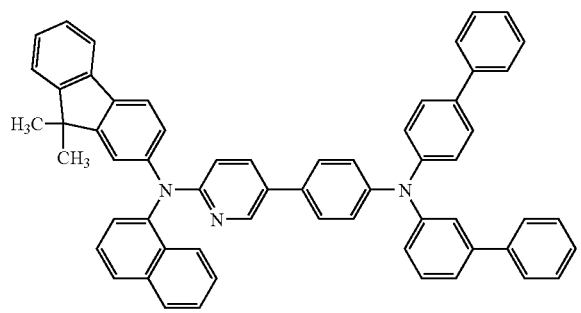
180
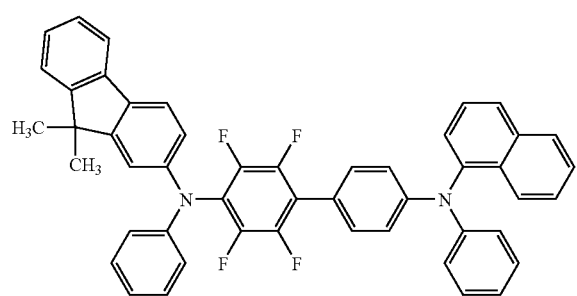
181
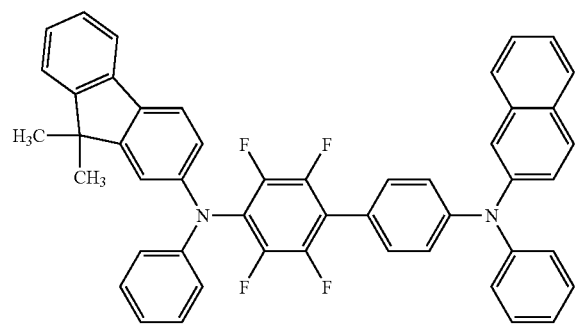
182
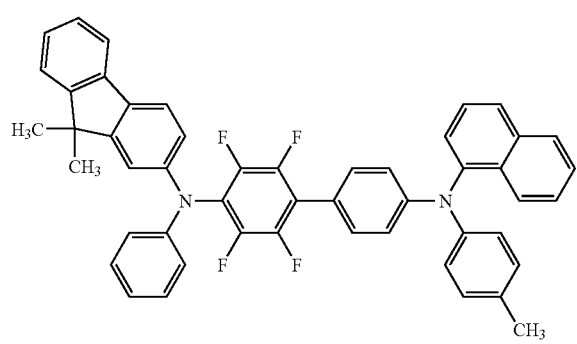
183
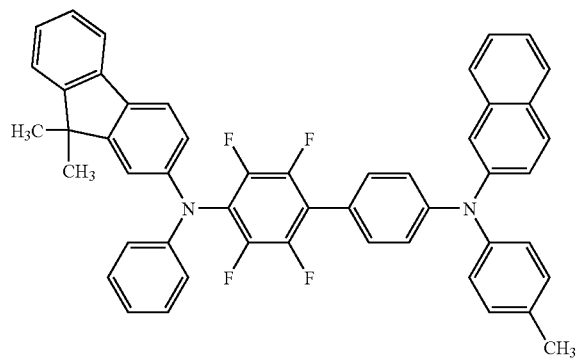
184
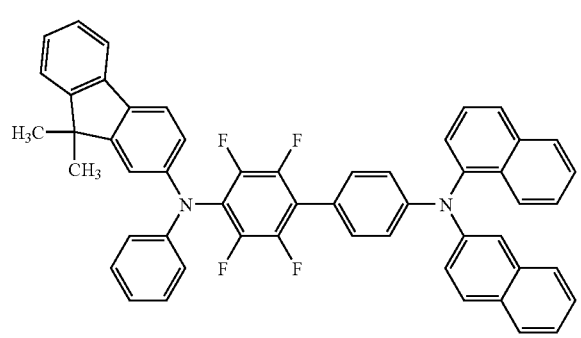
185
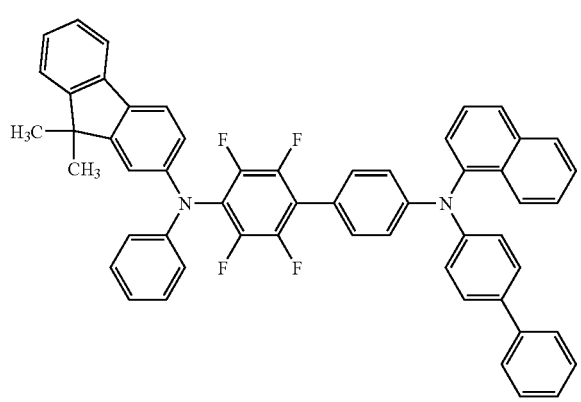
186
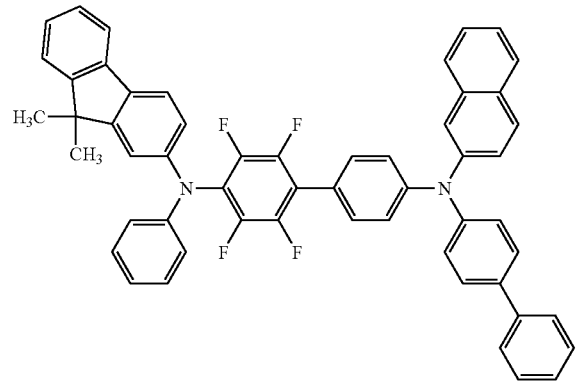
187

188
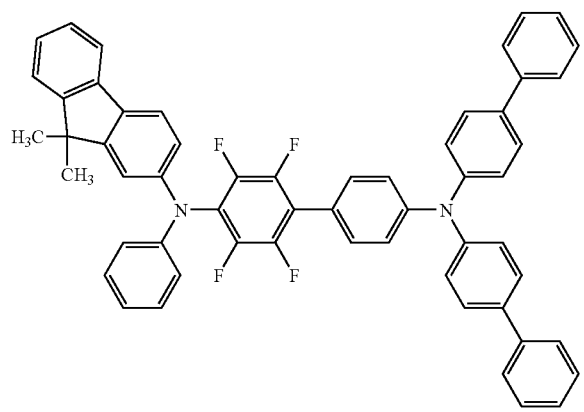
189
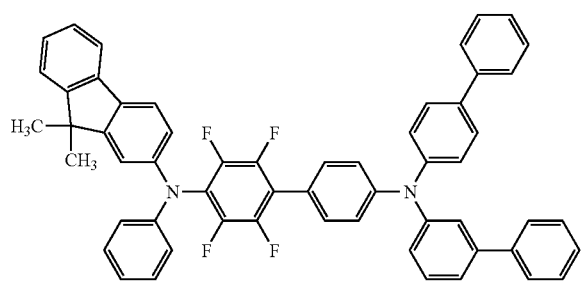
190
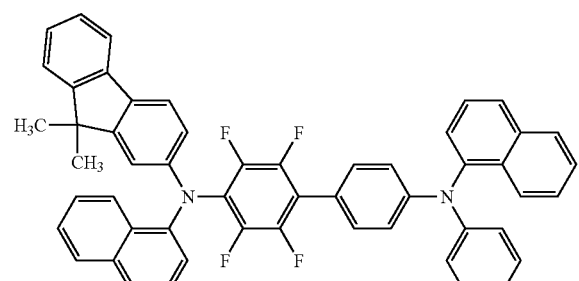
191
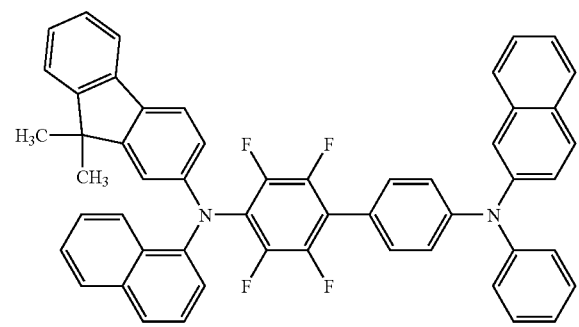
192
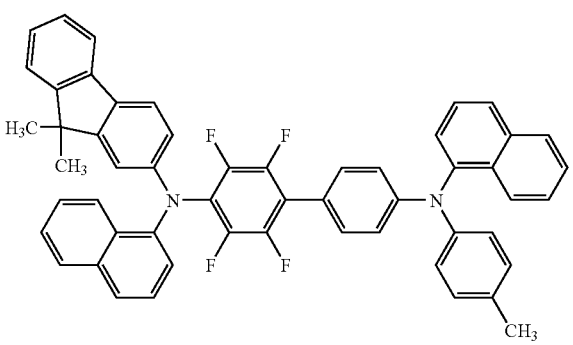
193
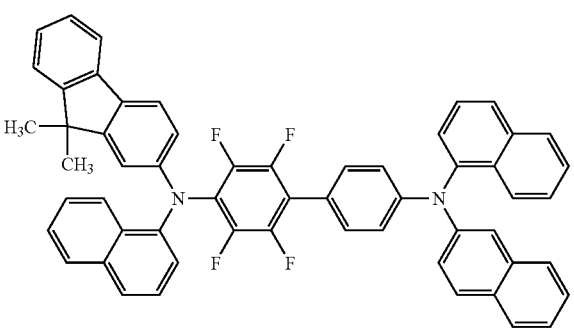
194
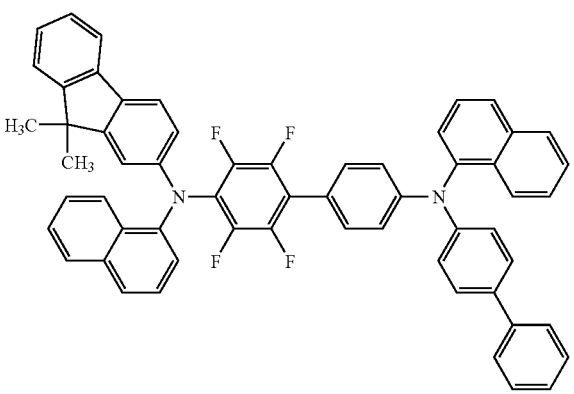
195

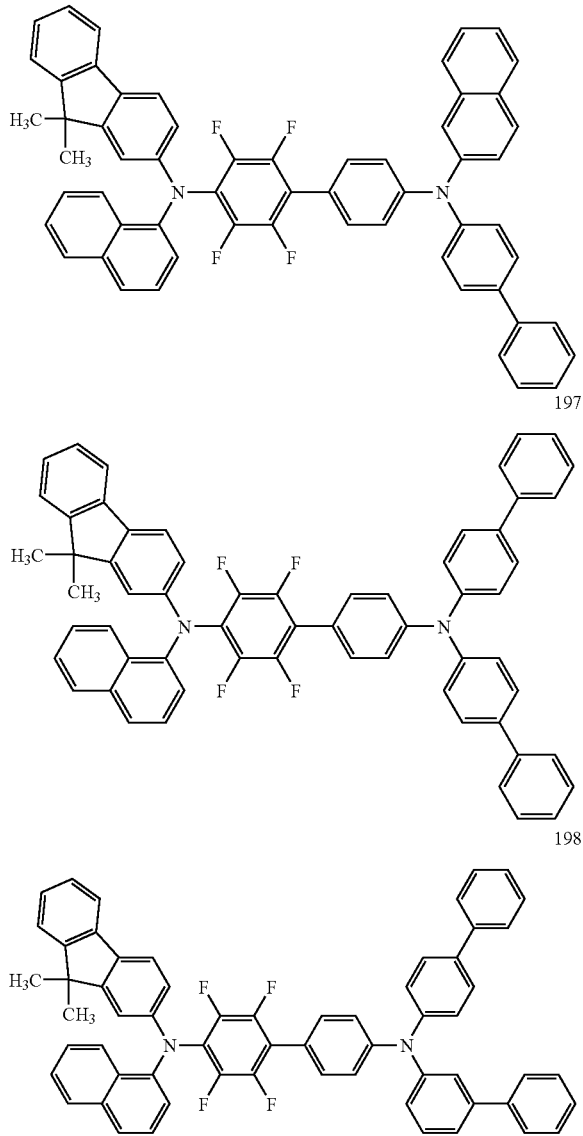

Another aspect of the present invention is directed to an organic electroluminescent device including a first electrode, a second electrode, and an organic layer interposed between the first electrode and the second electrode, wherein the organic layer includes the fluorene-containing compound represented by Formula 1 or 2. The organic layer including the fluorene-containing compound represented by Formula 1 or 2 may be a hole injection layer, a hole transport layer, or a single layer having a hole injecting capability and a hole transporting capability. The fluorene-containing compound represented by Formula 1 or 2 may also be an emission layer. In this case, the fluorene-containing compound represented by Formula 1 or 2 may be used as a blue, green, or red fluorescent or phosphorescent host material.

For example, the organic layer including the fluorene-containing compound represented by Formula 1 or 2 may be a hole transport layer. Meanwhile, the first electrode may be an anode and the second electrode may be a cathode, and otherwise, the first electrode may be a cathode and the second electrode may be an anode.

For the organic electroluminescent device, the organic layer may further include at least one layer selected from the group consisting of a hole injection layer, a hole transport layer, an electron blocking layer, an emission layer, a hole blocking layer, an electron transport layer and an electron injection layer, and if necessary, each of the layers may be a double layer. For example, an organic electroluminescent device according to an embodiment of the present invention includes a structure of first electrode/hole injection layer/emission layer/second electrode, a structure of first electrode/hole injection layer/hole transport layer/emission layer/electron transport layer/second electrode, or a structure of first electrode/hole injection layer/hole transport layer/emission layer/electron transport layer/electron injection layer/second electrode. The organic electroluminescent device may also have a structure of first electrode/a single layer having a hole injecting capability and a hole transporting capability/emission layer/electron transport layer/second electrode or first electrode/a single layer having a hole injecting capability and a hole transporting capability/emission layer/electron transport layer/electron injection layer/second electrode. An organic electroluminescent device according to aspects of the present invention may be applied in various display devices, such as a top emission type display device or a bottom emission type display device.

Hereinafter, a method of manufacturing an organic electroluminescent device according to an embodiment of the present invention will now be described in detail with reference to an example of an organic electroluminescent device as illustrated in FIG. 1. The organic electroluminescent device illustrated in FIG. 1 includes a substrate, a first electrode (anode), a hole injection layer, a hole transport layer, an emission layer, an electron transport layer, an electron injection layer and a second electrode (cathode).

First, the first electrode may be formed by depositing or sputtering a first electrode forming material having a high work function on the substrate. The first electrode may be an anode. Herein, the substrate may be any substrate that is used in a conventional organic electroluminescent device. For example, the substrate may be a glass or transparent plastic substrate that has mechanical strength, thermal stability, a flat surface, and convenience for handling, and is transparent and waterproof. The first electrode forming material may be a transparent, conductive material, such as indium tin oxide (ITO), indium zinc oxide (IZO), tin (IV) oxide ($SnO_2$), or zinc oxide (ZnO).

Then, the hole injection layer (HIL) may be formed on the first electrode using a vacuum-deposition method, a spin-coating method, a casting method, or a Langmuir-Blodgett (LB) deposition method. If the HIL is formed using the vacuum-deposition method, deposition conditions may differ according to the HIL forming material, the target layer structure, and the thermal characteristics. In this regard, in general, the deposition temperature may be 100 to 500° C., the degree of vacuum may be $10^{-8}$ to $10^{-3}$ torr, the deposition rate may be 0.01 to 100 Å/sec, and the thickness of the HIL may be 10 Å to 5 μm.

If the HIL is formed using the spin-coating method, coating conditions may differ according to the HIL forming material, the target layer structure, and the thermal characteristics. In this regard, in general, the coating rate may be about 2000 rpm to 5000 rpm, and the heat treatment temperature at which a solvent that has been used is removed after the coating may be about 80° C. to 200° C.

The HIL forming material may be the fluorene-containing compound represented by Formula 1 or 2 described above. The HIL forming material may also be any known hole injecting material. Examples of a known HIL forming material include phthalocyanine compounds such as copper phthalocyanine disclosed in U.S. Pat. No. 4,356,429, starburst type amine derivatives such as TCTA, m-MTDATA, or m-MTDAPB disclosed in Advanced Material, 6, p. 677(1994), and soluble conductive polymers such as polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA) or (polyaniline)/poly(4-styrenesulfonate) (PANI/PSS):

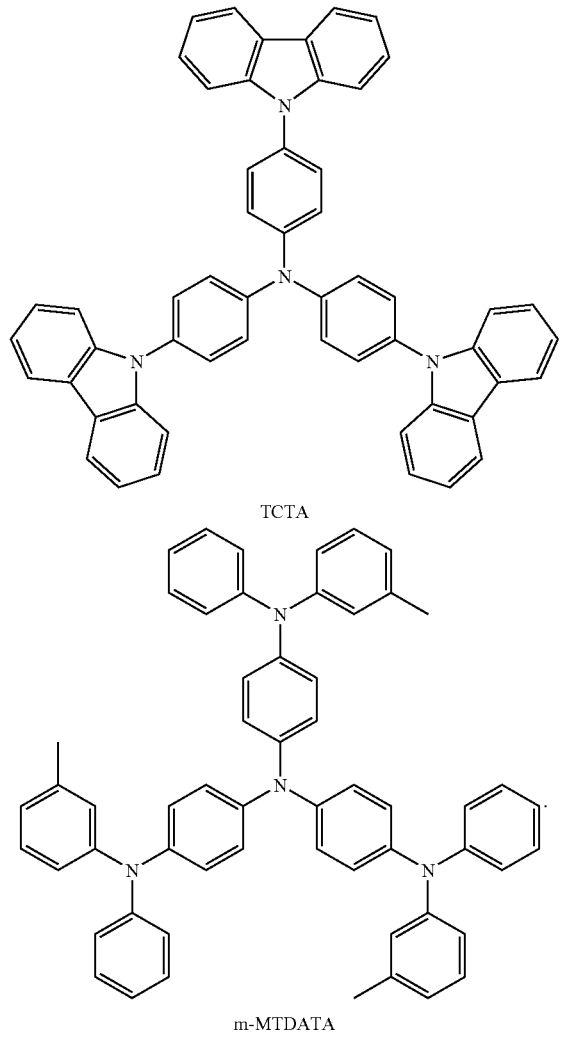

TCTA m-MTDATA

The thickness of the HIL may be about 100 Å to 10000 Å, specifically 100 Å to 1000 Å. If the thickness of the HIL is less than 100 Å, hole injecting characteristics may be degraded. On the other hand, if the thickness of the HIL is greater than 10000 Å, the driving voltage may be increased.

The hole transport layer (HTL) may be formed on the HIL using any known method, such as a vacuum-deposition method, a spin-coating method, a casting method, or an LB deposition method. When the HTL is formed using the vacuum-deposition method or the spin-coating method, deposition conditions and coating conditions may differ according to the HTL forming material. In this regard, deposition conditions and coating conditions may be the same or similar to those described with reference to the HIL.

The HTL forming material may be the fluorene-containing compound represented by Formula 1 or 2 described above. The HTL forming material may also be any known HTL forming material. Examples of the known HTL forming material include carbazole derivatives such as N-phenylcarbazole or polyvinylcarbazole, and amine derivatives having an aromatic condensation ring, such as N,N'-bis-(1-naphthalenyl)-N,N'-bis-(1,1'-biphenyl)4,4'diamine (NPB), N,N'-bis (3-methylphenyl)-N,N'-diphenyl-[1,1-biphenyl]-4,4'-diamine(TPD), or N,N'-di(naphthalene-1-yl)-N,N'-diphenyl benzidine(α-NPD):

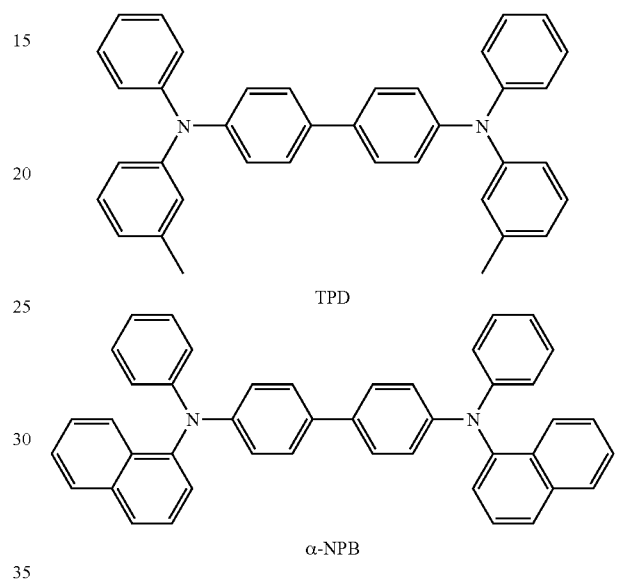

TPD

α-NPB

The thickness of the HTL may be about 50 Å to 1000 Å, specifically 100 Å to 600 Å. If the thickness of the HTL is less than 50 Å, hole transporting characteristics may be degraded. On the other hand, if the thickness of the HTL is greater than 1000 Å, the driving voltage may be increased.

Then, the emission layer (EML) may be formed on the HTL using any known method, such as a vacuum-deposition method, a spin-coating method, a casting method, or an LB deposition method. When the EML is formed using the vacuum-deposition method or the spin-coating method, deposition conditions and coating conditions may differ according to the EML forming material. In this regard, deposition conditions and coating conditions may be the same or similar to those described with reference to the HIL.

The EML may include the fluorene-containing compound represented by Formula 1 or 2 described above. For example, the fluorene-containing compound represented by Formula 1 or 2 described above may be used as a host of the EML. The EML may be formed using various known luminescent materials, such as known hosts and dopants. For the dopants, known fluorescent dopants and known phosphorescent dopants all can be used to form the EML. Examples of the host include $Alq_3$, 4,4'-N,N'-dicarbazole-biphenyl (CBP), poly(n-vinylcarbazole) (PVK), and distyrylarylene (DSA). However, the host is not limited to those materials.

With respect to dopants, examples of fluorescent dopants include DPVBi, C-545T, and DCJTB, and examples of phosphorescent dopants include $Ir(ppy)_3$ where ppy is an abbreviation of phenylpyridine (green), $(4,6-F2ppy)_2Irpic$ (see Chihaya Adachi etc. *Appl. Phys. Lett.*, 79, 2082-2084, 2001), TEB002 (available in the U.S. from EMD Chemicals, Inc., affiliated with Merck KGaA), platinum(II) octaethylporphyrin (PtOEP), a compound represented by Formula 5 (see KR Patent Publication No. 2005-0078472), Firpic, and RD 61 that is a red phosphorescent dopant produced by UDC Co. However, dopants are not limited to those materials.

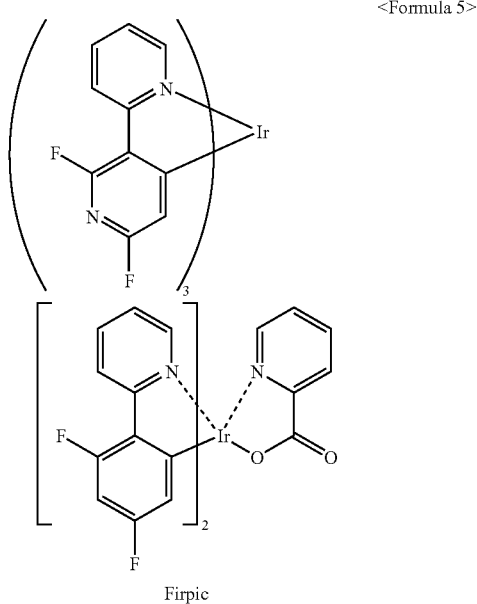

<Formula 5>

Firpic

The amount of the dopant may be 0.1 to 20 parts by weight, specifically 0.5 to 12 parts by weight based on 100 parts by weight of the EML forming material (that is, the total weight of the host and dopant is set at 100 parts by weight). If the amount of the dopant is less than 0.1 parts by weight, the dopant-addition-effect is negligible. On the other hand, if the amount of the dopant is greater than 20 parts by weight, in both phosphorescent and fluorescent cases, concentration quenching may occur.

The thickness of the EML may be about 100 Å to 1000 Å, specifically 200 Å to 600 Å. If the thickness of the emission layer is less than 100 Å, luminescent characteristics may be degraded. On the other hand, if the thickness of the emission layer is greater than 1000 Å, the driving voltage may be increased.

When the EML is formed using a phosphorescent dopant, diffusion of triplet exitons or holes into the electron transport layer (ETL) can be prevented by forming a hole blocking layer (HBL) (not shown) between the HTL and the EML. In this case, an available HBL forming material is not limited and may be selected from known HBL forming materials hole blocking layer. Examples of the HBL forming material include an oxadiazole derivative, a triazole derivative, a phenanthroline derivative, a hole blocking mateiral disclosed in JP 11-329734(A1), Balq, and BCP.

The thickness of the HBL may be about 50 Å to 1000 Å, specifically 100 Å to 300 Å. If the thickness of the hole blocking layer is less than 50 Å, hole blocking characteristics may be degraded. On the other hand, if the thickness of the hole blocking layer is greater than 1000 Å, the driving voltage may be increased.

Then the electron transport layer (ETL) may be formed using any known method, such as a vacuum-deposition method, a spin-coating method, or a casting method. When the ETL is formed using the vacuum-deposition method or the spin-coating method, deposition conditions and coating conditions may differ according to the ETL forming material. In this regard, deposition conditions and coating conditions may be the same or similar to those described with reference to the HIL. The ETL forming material is not limited and may be selected from known ETL forming materials. Examples of the ETL forming material include quinoline derivatives, such as tris(8-quinolinolate)aluminum ($Alq_3$) or TAZ.

The thickness of the ETL may be about 100 Å to 1000 Å, specifically 100 Å to 500 Å. If the thickness of the ETL is less than 100 Å, electron transporting characteristics may be degraded. On the other hand, if the thickness of the ETL is greater than 1000 Å, the driving voltage may be increased.

In addition, an electron injection layer (EIL) that allows electrons to be easily injected from an anode may be formed on the ETL. The EIL may be formed using any known EIL forming material, such as LiF, NaCl, a CsF, $Li_2O$, or BaO. The deposition conditions and coating conditions of the EIL may differ according to the EIL forming material. In general, however, the deposition conditions and coating conditions may be the same or similar to those described with reference to the HIL.

The thickness of the EIL may be about 1 Å to 100 Å, specifically 5 Å to 90 Å. If the thickness of the EIL is less than 1 Å, electron injecting characteristics may be degraded. On the other hand, if the thickness of the EIL is greater than 100 Å, the driving voltage may be increased.

Then the second electrode is formed on the EIL using a vacuum-deposition method or a sputtering method. The second electrode may function as a cathode or an anode. The second electrode may be formed using metal, alloy, an electro-conductive compound, or any mixture thereof, each of which has a low work function. Examples of such materials include lithium (Li), magnesium (Mg), aluminum (Al), aluminum-lithium (Al—Li), calcium (Ca), magnesium-indium (Mg—In), and magnesium-silver (Mg—Ag). In addition, to produce a top emission type display device, the second electrode may be formed using a transparent material such as ITO or IZO.

The organic electroluminescent device according to the present invention may be included in various types of flat panel devices, such as passive matrix organic light emitting display devices or active matrix organic light emitting display devices. Specifically, when the organic electroluminescent device according to aspects of the present invention is used in active matrix organic light emitting display devices, the first electrode disposed on a substrate side may function as a pixel electrode and may be electrically connected to a source electrode or drain electrode of a thin film transistor. In addition, the organic electroluminescent device according to aspects of the present invention may also be used in a flat panel apparatus that includes screens on opposite sides.

Hereinafter, synthesis examples and examples of the fluorene-containing compound represented by Formula 1 or 2 according to the present invention will be described in detail. However, the present invention will not be limited to those examples.

EXAMPLES

Synthesis Example 1

Production of Compound 1

Compound 1 was synthesized through the reaction pathway illustrated in Reaction

<Reaction Scheme 1>
Scheme 1.
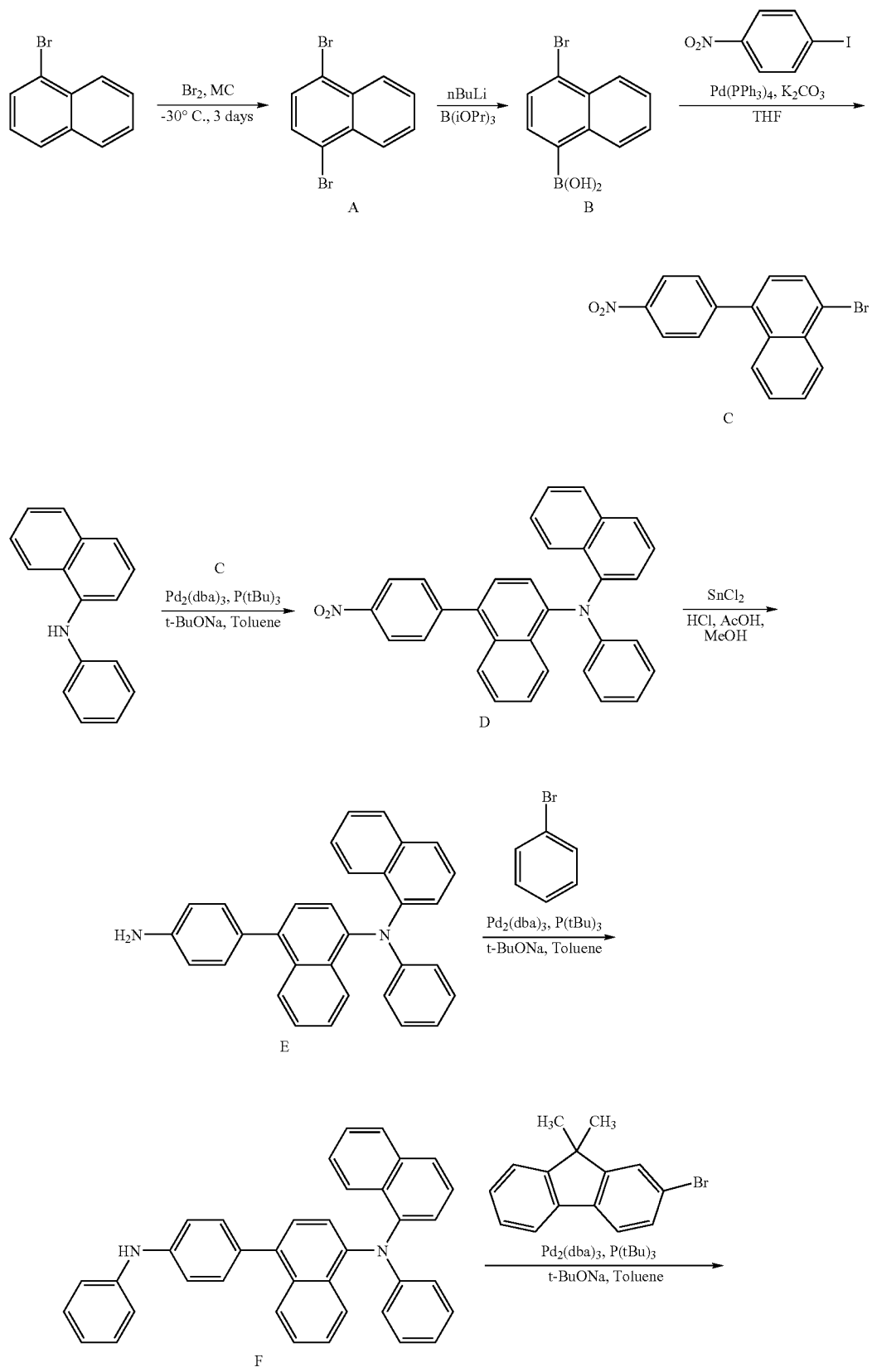

-continued

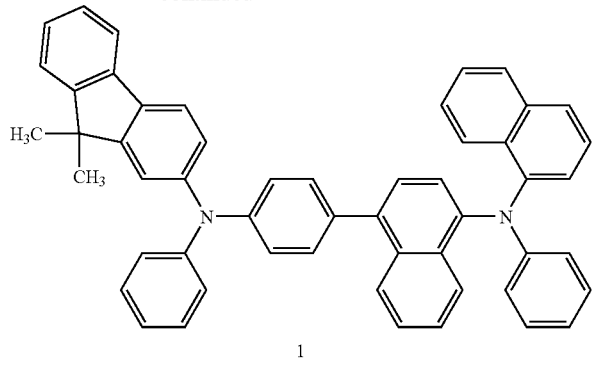

1

(1) Synthesis of Intermediate A 20.7 g (100 mmol) of 1-bromonaphthalene were dissolved in 300 Ml of dichloromethane and cooled to a temperature of −30° C. A solution prepared by dissolving 2.56 g (50 mmol) of bromine in 30 Ml of dichloromethane was cooled to a temperature of −30° C., and then slowly added to the reaction solution. After the addition was completed, the resultant solution was placed in a freezer at −30° C. for 72 hours without exposure to light. Then, a 10% sodium thiosulfate aqueous solution was added to the resultant reaction solution and then the organic layer was collected. The collected organic layer was dried over magnesium sulfate and any solvent included therein was evaporated. The residue was re-crystallized with diethylether and normal hexane to produce 24.3 g (yield 85%) of Intermediate A. Intermediate A was a white solid. $^1$H NMR (CDCl$_3$, 400 MHz) δ (ppm) −8.26-8.24 (m, 2H), 7.66-7.63 (m, 4H).

(2) Synthesis of Intermediate B 14.3 g (50 mmol) of Intermediate A were dissolved in 150 Ml of diethylether and then normal butyl lithium (20 Ml, 2.5M in Hexane) was added thereto at a temperature of −78° C. The mixture was stirred at that temperature for 30 minutes. Then, the temperature was slowly increased to room temperature. The resultant mixture solution was left to sit for 30 minutes. Then, a solution prepared by dissolving 23 Ml (100 mmol) of triisopropylborate in 50 Ml of diethylether was maintained at a temperature of −78° C. and then the resultant solution was slowly added thereto. The reaction solution was stirred at room temperature for 5 hours and then 1N HCl solution was added thereto. Then, the resultant solution was extracted three times with diethylether (200 Ml). The obtained diethylether layers were dried over MgSO$_4$, and then dried under reduced pressure to produce a pre-product. The pre-product was re-crystallized using normal hexane to produce 9.6 g (yield 77%) of Intermediate B. Intermediate B was a white solid. $^1$H NMR (CDCl$_3$, 400 MHz) δ (ppm) −8.05 (d, 1H), 7.85 (d, 1H), 7.73 (m, 4H), 7.35 (s, 2H).

(3) Synthesis of Intermediate C 7.53 g (30 mmol) of Intermediate B, 15 g (60 mmol) of 4-iodonitrobenzene, 1.7 g (1.5 mmol) of Pd(PPh$_3$)$_4$ and 20 g (150 mmol) of K$_2$CO$_3$ were dissolved in 100 ME of THF/H$_2$O(2:1) mixed solvent and then stirred at 80° C. for 5 hours. The reaction solution was extracted three times with 200 Ml of diethylether, and then the collected organic layers were dried over magnesium sulfate and any solvent contained therein was evaporated. The residue was re-crystallized with dichloromethane and normal hexane to produce 7.68 g (yield 78%) of Intermediate C. $^1$H NMR (CDCl$_3$, 400 MHz) δ (ppm) −8.14 (d, 1H), 8.10-8.06 (m, 2H), 7.86 (d, 1H), 7.81-7.71 (m, 2H), 7.66 (d, 1H), 7.58-7.53 (m, 3H).

(4) Synthesis of Intermediate D 5 g (15.2 mmol) of Intermediate C, 4 g (18.2 mmol) of 1-naphthylphenylamine, 2.2 g (23 mmol) of t-BuONa, 0.28 g (0.3 mmol) of Pd$_2$(dba)$_3$ and 0.061 g (0.3 mmol) of P(t-Bu)$_3$ were dissolved in 500 Ml of toluene, and then the mixture was stirred at 90° C. for 3 hours. After the reaction was completed, the reaction solution was cooled to room temperature and then extracted three times with distilled water and 50 Ml of diethylether. The collected organic layers were dried over magnesium sulfate and any solvent contained therein was evaporated. The residue was isolated and refined by silica gel column chromatography to produce 4.6 g (yield 65%) of Intermediate D. $^1$H NMR (CDCl$_3$, 400 MHz) δ (ppm) −8.49 (dd, 1H), 8.10-8.06 (dd, 3H), 7.85 (dd, 1H), 7.67-7.27 (m, 13H), 6.64-6.60 (m, 1H), 6.10 (d, 1H), 5.65 (dd, 2H).

(5) Synthesis of Intermediate E 189 mg (1 mmol) of SnCl$_2$ and a small amount of HCl were added to a solution prepared by dissolving 4.6 g (10 mmol) of Intermediate D in 20 Ml of acetic acid and 10 Ml of methanol and the mixture was stirred at 80° C. for 5 hours. After the reaction was completed, the reaction solution was cooled to room temperature and then extracted three times with distilled water and 50 Ml of diethylether. The collected organic layers were dried over magnesium sulfate and any solvent included therein was evaporated. The residue was isolated and refined by silica gel column chromatography to produce 3.88 g (yield 89%) of Intermediate E. $^1$H NMR (CDCl$_3$, 400 MHz) δ (ppm) −8.49 (dd, 1H), 8.04 (d, 1H), 7.85 (dd, 1H), 7.65-7.27 (m, 13H), 6.70-6.60 (m, 3H), 6.10 (dd, 1H), 5.65 (dd, 2H), 5.48 (s, 2H).

(6) Synthesis of Intermediate F 4.4 g (10 mmol) of Intermediate E, 1.05 Ml (10 mmol) of bromobenzene, 1.4 g (15 mmol) of t-BuONa, 0.18 g (0.2 mmol) of Pd$_2$(dba)$_3$ and 0.04 g (0.2 mmol) of P(t-Bu)$_3$ were dissolved in 40 Ml of toluene and then the mixture was stirred at 90° C. for three hours. After the reaction was completed, the reaction solution was cooled to room temperature, and then extracted three times with distilled water and 40 Ml of diethylether. The collected organic layers were dried over magnesium sulfate and any solvent included therein was evaporated. The residue was isolated and refined by silica gel column chromatography to produce 3.07 g (yield 60%) of Intermediate F. $^1$H NMR (CDCl$_3$, 400 MHz) δ (ppm) −8.49 (dd, 1H), 8.05 (d, 1H), 7.85 (dd, 1H), 7.63-7.25 (m, 15H), 7.12 (d, 2H), 6.90-6.60 (m, 4H), 6.10 (dd, 1H), 5.65 (d, 2H), 5.51 (s, NH).

(7) Synthesis of Compound 1

5.1 g (10 mmol) of Intermediate F. 3.0 g (11 mmol) of 2-bromo-9,9-dimethyl-fluorene, 1.4 g (15 mmol) of t-BuONa, 0.18 g (0.2 mmol) of Pd$_2$(dba)$_3$ and 0.04 g (0.2 mmol) of P(t-Bu)$_3$ were dissolved in 40 Ml of toluene and the mixture was stirred at 90° C. for 3 hours. After the reaction was completed, the reaction solution was cooled to room temperature, and then extracted three times with distilled water and 40 Ml of diethylether. The collected organic layers were dried over magnesium sulfate and any solvent included therein was evaporated. The residue was isolated and refined by silica gel column chromatography to produce 6.2 g (yield 88%) of Compound 1. $^1$H NMR (CDCl$_3$, 400 MHz) δ (ppm) −8.48 (dd, 1H), 8.20 (dd, 1H), 7.97 (dd, 1H), 7.84 (d, 1H), 7.68 (d, 1H), 7.65-7.15 (m, 18H), 6.95 (t, 1H), 6.62 (m, 2H), 6.43-6.39 (m, 2H), 6.33 (dd, 1H), 6.10 (d, 1H), 5.68-5.63 (m, 4H), 1.85 (s, 6H).

Synthesis Example 2

Production of Compound 8

Compound 8 was synthesized through the reaction pathway illustrated in Reaction Scheme 2:

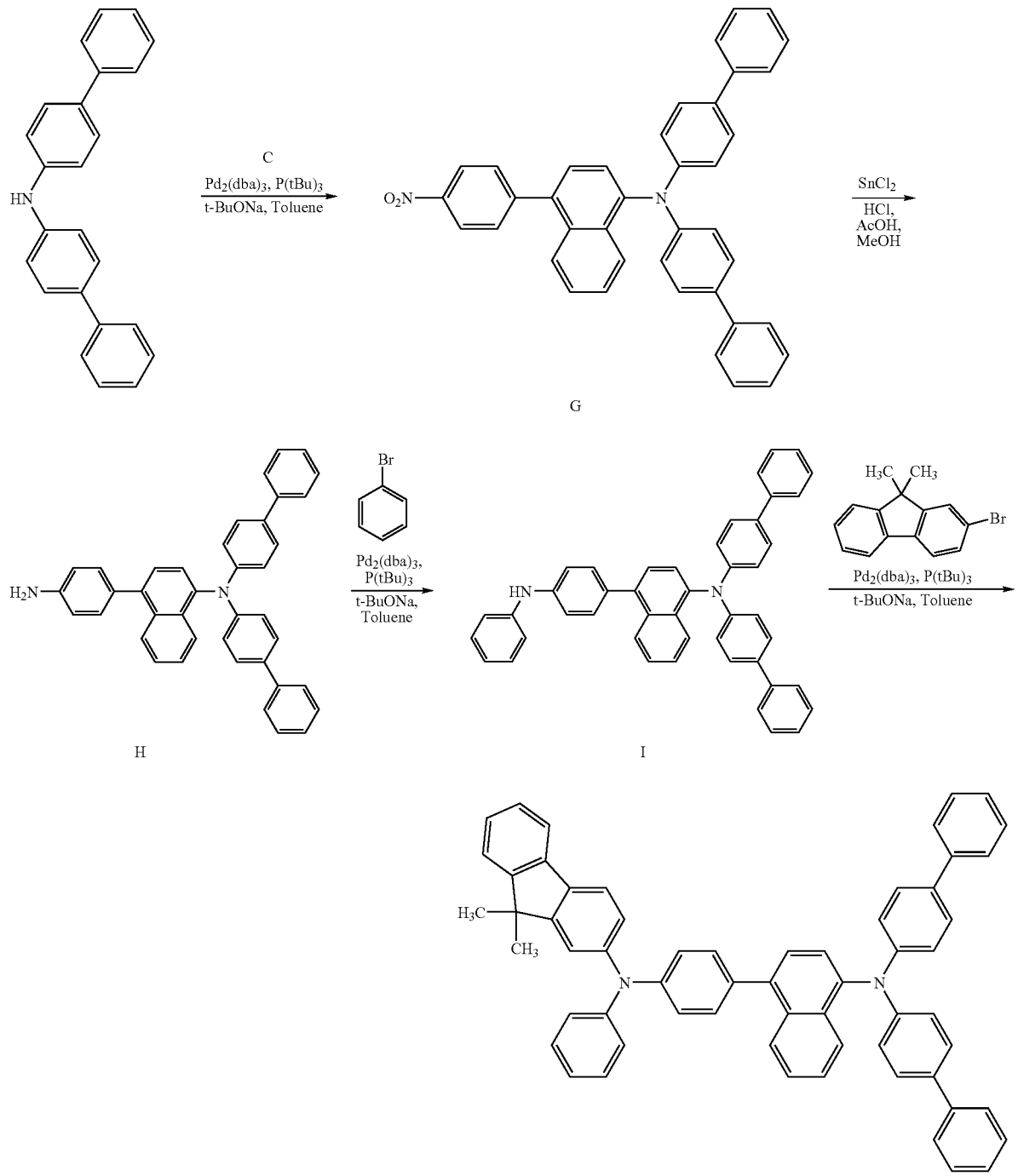

(8) Synthesis of Intermediate G

Intermediate G (yield: 62%) was synthesized in the same manner as Intermediate D was synthesized, except that bis-biphenyl-4-amine was used instead of naphthylphenylamine. ¹H NMR (CDCl₃, 400 MHz) δ (ppm) −8.10-8.06 (m, 3H), 7.76-7.73 (m, 4H), 7.68-7.60 (m, 8H), 7.54 (d, 1H), 7.43-7.29 (m, 8H), 6.45-6.41 (m, 4H).

(9) Synthesis of Intermediate H

Intermediate H (yield: 90%) was synthesized in the same manner as Intermediate E was synthesized, except that Intermediate G was used instead of Intermediate D. ¹H NMR (CDCl₃, 400 MHz) δ (ppm) −8.04 (d, 1H), 7.76-7.60 (m, 10H), 7.54 (dd, 1H), 7.41-7.29 (m, 10H), 6.70-6.66 (m, 2H), 6.45-6.41 (m, 4H), 5.48 (s, NH).

(10) Synthesis of Intermediate I

Intermediate I (yield: 63%) was synthesized in the same manner as Intermediate F was synthesized, except that Intermediate H was used instead of Intermediate E. ¹H NMR (CDCl₃, 400 MHz) δ (ppm) −8.05 (d, 1H), 7.76-7.10 (m, 25H), 6.88 (t, 1H), 6.79-6.75 (m, 2H), 6.45-6.41 (m, 4H), 5.51 (s, NH).

(11) Synthesis of Compound 8

Compound 8 (yield: 60%) was synthesized in the same manner as Compound 1 was synthesized, except that Intermediate I was used instead of Intermediate F. ¹H NMR (CDCl₃, 400 MHz) δ (ppm) −8.21 (d, 1H), 7.98 (d, 1H), 7.76-7.14 (m, 27H), 6.97-6.93 (m, 1H), 6.64-6.59 (m, 1H), 6.45-6.32 (m, 7H), 5.68-5.66 (m, 2H), 1.85 (s, 6H).

Synthesis Example 3

Production of Compound 17

Compound 17 was synthesized through the reaction pathway illustrated in Reaction Scheme 3:

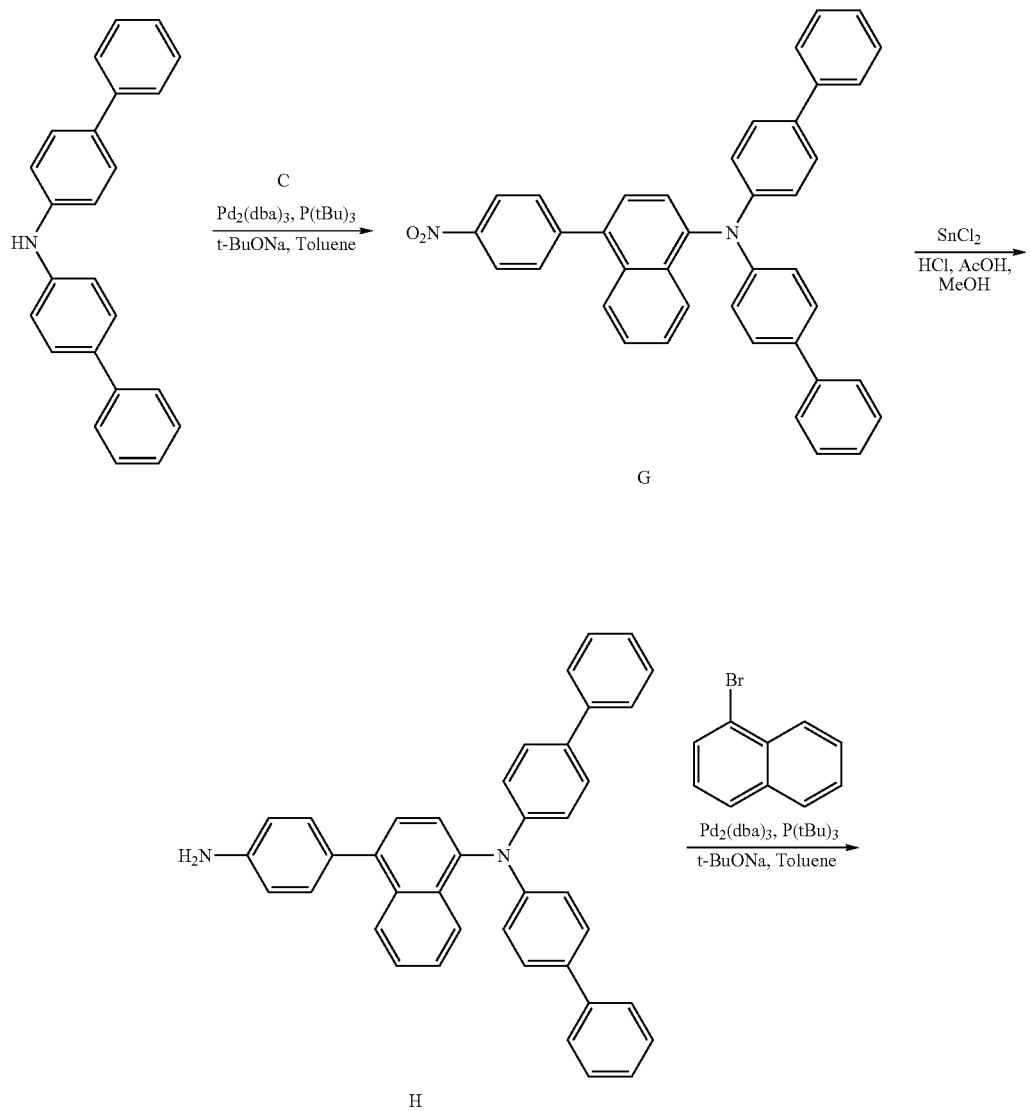

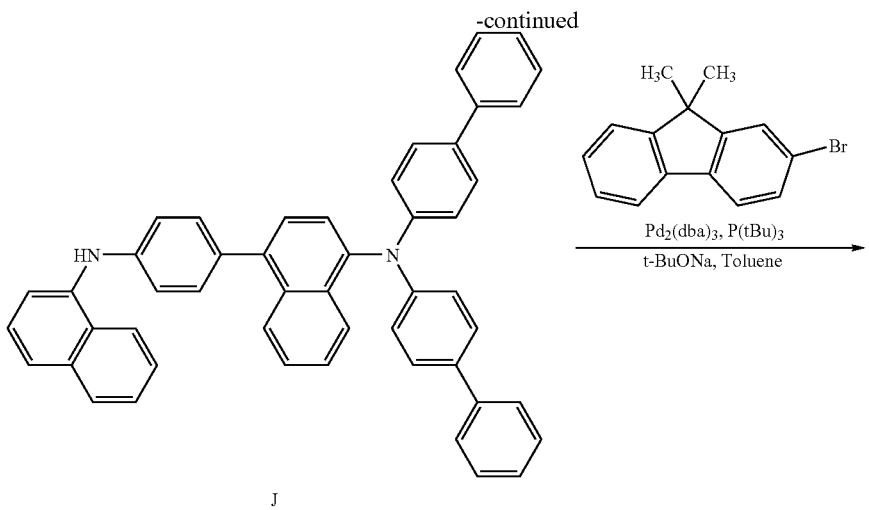

J

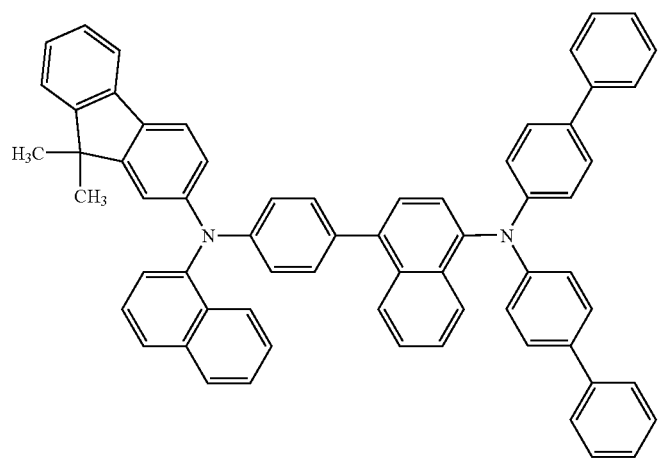

17

(12) Synthesis of Intermediate J

Intermediate J (yield: 58%) was synthesized in the same manner as Intermediate I was synthesized, except that 1-bromonaphthalene was used instead of bromobenzene. $^1$H NMR (CDCl$_3$, 400 MHz) δ (ppm) −8.41 (dd, 1H), 8.05 (d, 1H), 7.75-7.13 (m, 27H), 6.77-6.73 (m, 2H), 6.45-6.41 (m, 4H), 5.91 (s, NH).

(13) Synthesis of Compound 17

Compound 17 (yield: 53%) was synthesized in the same manner as Compound 8 was synthesized, except that Intermediate J was used instead of Intermediate I. $^1$H NMR (CDCl$_3$, 400 MHz) δ (ppm) −8.50 (dd, 1H), 8.21 (d, 1H), 7.98 (d, 1H), 7.84 (dd, 1H), 7.76-7.20 (m, 28H), 7.13 (d, 1H), 6.97-6.93 (m, 1H), 6.45-6.36 (m, 6H), 6.31 (dd, 1H), 6.10 (dd, 1H), 1.65 (s, 6H).

Synthesis Example 4

Production of Compound 35

Compound 35 was synthesized through the reaction pathway illustrated in Reaction Scheme 4:

<Reaction Scheme 4>

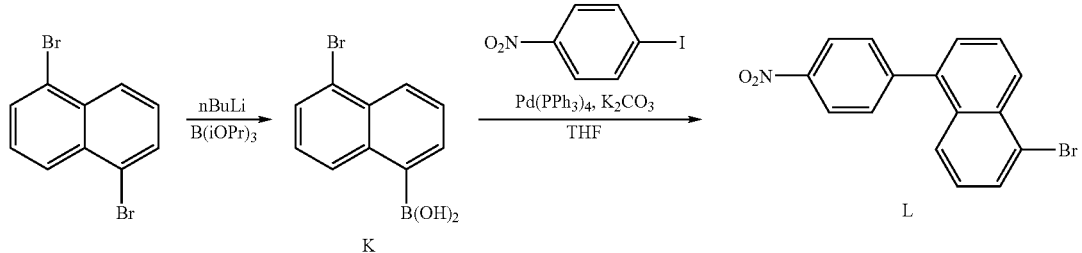

-continued
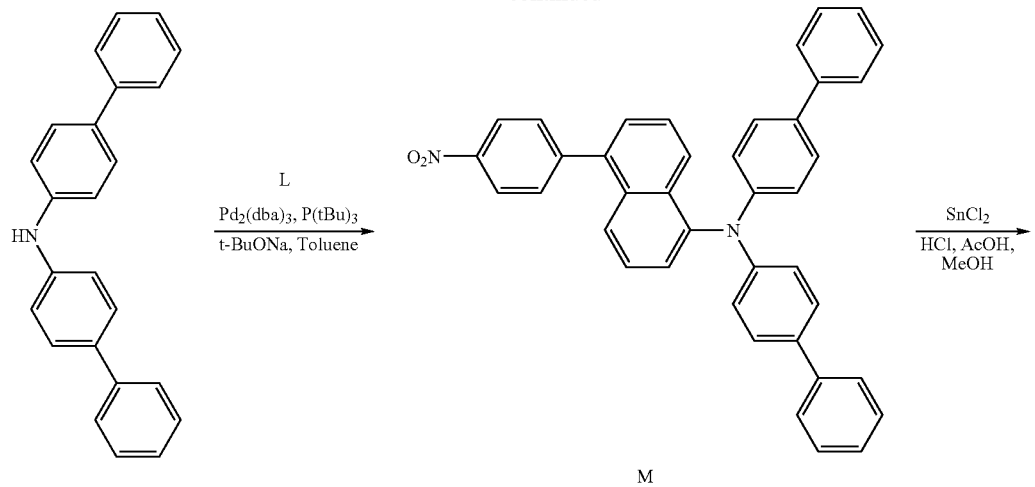
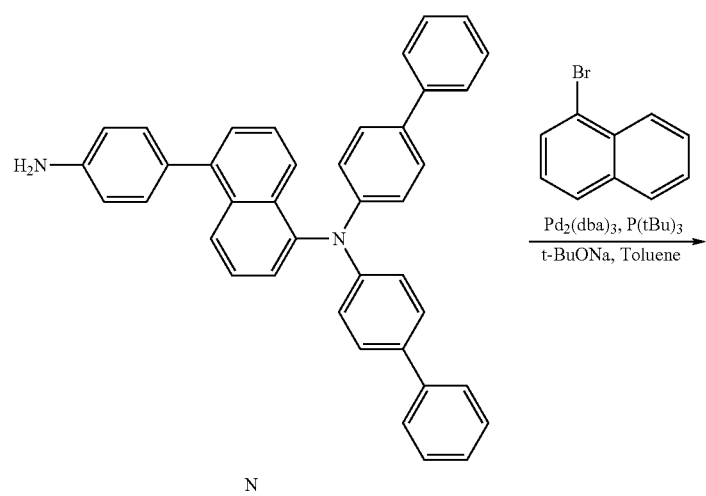
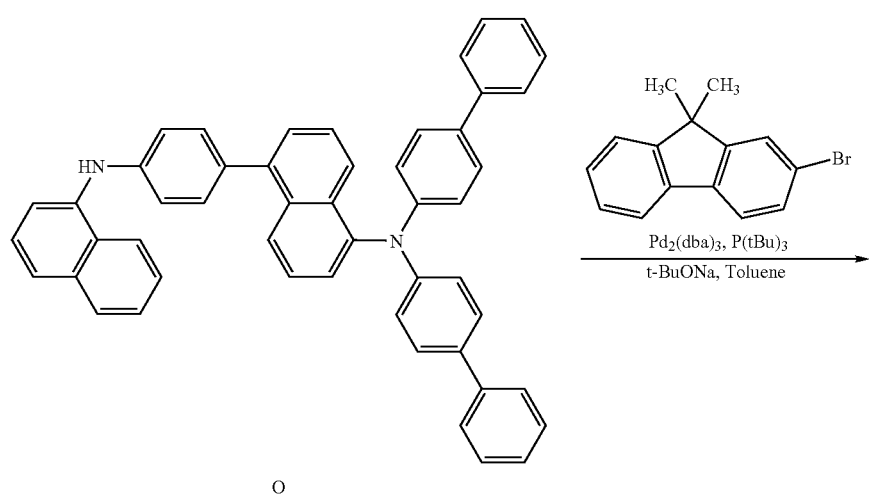

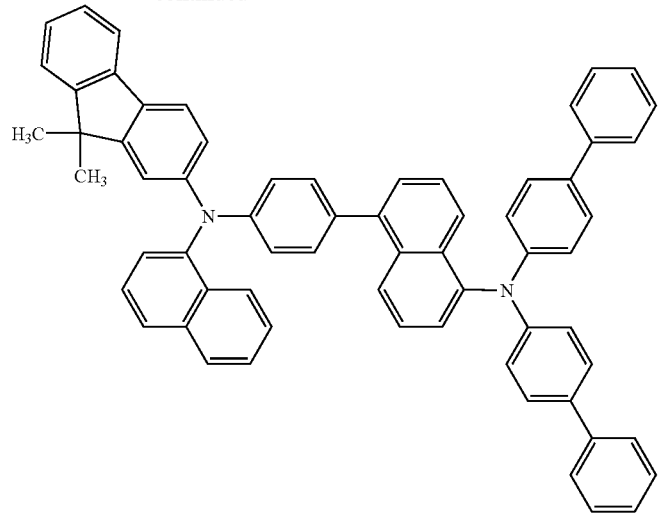

35

(14) Synthesis of Intermediate K 14.3 g (50 mmol) of 1,5-dibromonaphthalene were dissolved in 150 Ml of diethylether and then normal butyllithium (20 Ml, 2.5 M hexane solution) was added thereto at −78° C. The mixture was stirred for 30 minutes and then the temperature was slowly increased to room temperature. The resultant mixture solution was left to sit for 30 minutes. Then, while a solution prepared by dissolving 23 Ml (100 mmol) of triisopropylborate in 50 Ml of diethylether was maintained at a temperature of −78° C., the mixture solution was slowly added thereto. The resultant mixture was stirred at room temperature for 5 hours and then a 1N HCl solution was added thereto and the solution was washed three times with diethylether (200 Ml). The washed diethylether layer was dried over MgSO$_4$ and dried under reduced pressure to prepare a product. The product was re-crystallized to produce 9.15 g (yield 73%) of Intermediate K. Intermediate K was a white solid. $^1$H NMR (CDCl$_3$, 400 MHz) δ (ppm) −8.06-8.01 (m, 2H), 7.85 (dd, 1H), 7.65 (dd, 1H), 7.52-7.48 (t, 1H), 7.35 (s, 1H), 7.20 (t, 1H).

(15) Synthesis of Intermediate L 7.53 g (30 mmol) of Intermediate K, 15 g (60 mmol) of 4-iodonitrobenzene, 1.7 g (1.5 mmol) of Pd(PPh3)4 and 20 g (150 mmol) of K$_2$CO$_3$ were dissolved in 100 Ml of mixed solvent THF/H$_2$O(2:1) and then, the mixture was stirred at 80° C. for 5 hours. The reaction solution was extracted three times with 200 Ml of diethylether, and then the collected organic layers were dried over magnesium sulfate and any solvent included therein was evaporated. The residue was re-crystallized with dichloromethane and normal hexane to produce 7.09 g (yield 72%) of Intermediate L. 1H NMR (CDCl3, 400 MHz) δ (ppm) −8.14 (d, 1H), 8.10-8.06 (m, 2H), 7.94 (dd, 1H), 7.77 (dd, 1H), 7.66 (d, 1H), 7.58-7.54 (m, 2H), 7.45 (t, 1H), 7.22 (t, 1H)

(16) Synthesis of Intermediate M

Intermediate M (yield: 58%) was synthesized in the same manner as Intermediate G was synthesized, except that Intermediate L was used instead of Intermediate C. $^1$H NMR (CDCl$_3$, 400 MHz) δ (ppm) −8.52 (dd, 1H), 8.19 (d, 1H), 8.10-8.06 (m, 2H), 7.76-7.29 (m, 19H), 6.45-6.41 (m, 4H), 6.18 (dd, 1H).

(17) Synthesis of Intermediate N

Intermediate N (yield: 92%) was synthesized in the same manner as Intermediate H was synthesized, except that Intermediate M was used instead of Intermediate G. $^1$H NMR (CDCl$_3$, 400 MHz) δ (ppm) −8.52 (dd, 1H), 8.19 (d, 1H), 7.76-7.29 (m, 19H), 6.70-6.66 (m, 2H), 6.45-6.41 (m, 4H), 6.18 (dd, 1H), 5.48 (s, NH).

(18) Synthesis of Intermediate O

Intermediate O (yield: 60%) was synthesized in the same manner as Intermediate J was synthesized, except that Intermediate N was used instead of Intermediate H. $^1$H NMR (CDCl$_3$, 400 MHz) δ (ppm) −8.52 (dd, 1H), 8.41 (dd, 1H), 8.19 (d, 1H), 7.75-7.13 (m, 25H), 6.77-6.73 (m, 2H), 6.45-6.41 (m, 4H), 6.18 (dd, 1H), 5.91 (s, NH).

(19) Synthesis of Compound 35

Compound 35 (yield: 64%) was synthesized in the same manner as Compound 1 was synthesized, except that Intermediate O was used instead of Intermediate F. $^1$H NMR (CDCl$_3$, 400 MHz) δ (ppm) −8.53-8.48 (m, 2H), 8.19 (d, 1H), 7.98 (d, 1H), 7.86-7.12 (m, 28H), 6.97-6.93 (m, 1H), 6.45-6.36 (m, 6H), 6.31 (dd, 1H), 6.18 (dd, 1H), 6.11 (dd, 1H), 1.85 (s, 6H).

Synthesis Example 5

Production of Compound 53

Compound 53 was synthesized through the reaction pathway illustrated in Reaction Scheme 5:

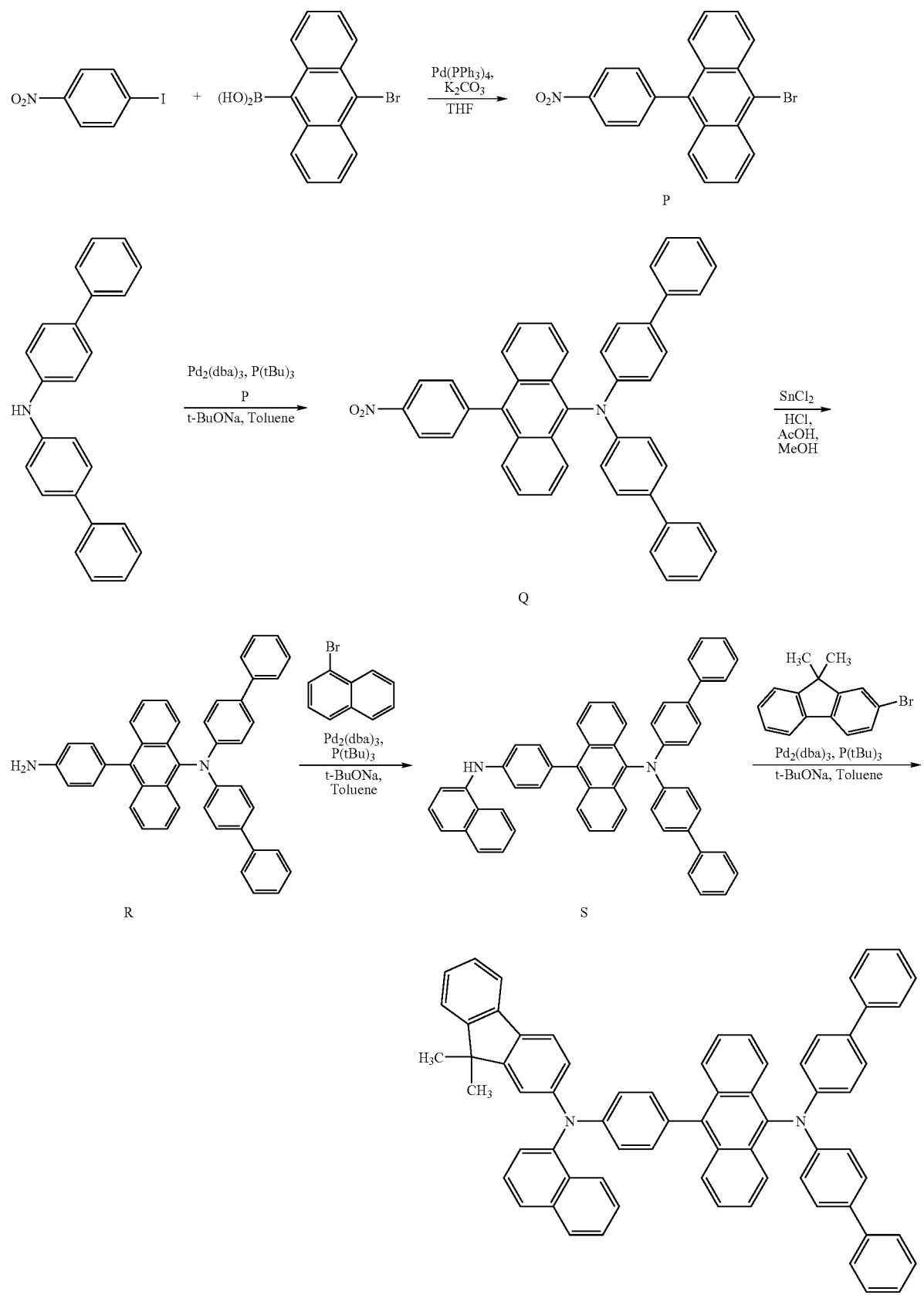
<Reaction Scheme 5>

(20) Synthesis of Intermediate P 9.03 g (30 mmol) of 10-bromoanthracene-9-boronic acid, 15 g (60 mmol) of 4-iodonitrobenzene, 1.7 g (1.5 mmol) of Pd(PPh$_3$)$_4$ and 20 g (150 mmol) of K$_2$CO$_3$ were dissolved in 100 Ml of mixed solvent THF/H$_2$O(2:1) and then the mixture was stirred at 80° C. for 5 hours. The reaction solution was extracted three times with 200 Ml of diethylether, and the collected organic layers were dried over magnesium sulfate and any solvent contained therein was evaporated. The residue was re-crystallized with dichloromethane and normal hexane to produce 7.15 g (yield 63%) of Intermediate P. 1H NMR (CDCl$_3$, 400 MHz) δ (ppm) –8.07-7.94 (m, 6H), 7.62-7.58 (m, 2H), 7.55-7.48 (m, 4H).

(21) Synthesis of Intermediate Q

Intermediate Q (yield: 60%) was synthesized in the same manner as Intermediate G was synthesized, except that Intermediate P was used instead of Intermediate C. $^1$H NMR (CDCl$_3$, 400 MHz) δ (ppm) –8.56-8.53 (m, 2H), 8.07-8.03 (m, 4H), 7.76-7.53 (m, 12H), 7.40-7.23 (m, 8H), 6.42-6.38 (m, 4H).

(22) Synthesis of Intermediate R

Intermediate R (yield: 90%) was synthesized in the same manner as Intermediate H was synthesized, except that Intermediate Q was used instead of Intermediate G. $^1$H NMR (CDCl$_3$, 400 MHz) δ (ppm) –8.56-8.53 (m, 2H), 8.04 (d, 2H), 7.76-7.23 (m, 20H), 6.68-6.64 (m, 2H), 6.42-6.38 (m, 4H), 5.48 (s, NH).

(23) Synthesis of Intermediate S

Intermediate S (yield: 55%) was synthesized in the same manner as Intermediate J was synthesized, except that Intermediate R was used instead of Intermediate H. $^1$H NMR (CDCl$_3$, 400 MHz) δ (ppm) –8.56-8.53 (m, 2H), 8.41 (dd, 1H), 8.05-8.03 (m, 2H), 7.76-7.13 (m, 26H), 6.74-6.70 (m, 2H), 6.42-6.38 (m, 4H), 5.91 (s, NH).

(24) Synthesis of Compound 53

Compound 53 (yield: 61%) was synthesized in the same manner as Compound 1 was synthesized, except that Intermediate S was used instead of Intermediate F. $^1$H NMR (CDCl$_3$, 400 MHz) δ (ppm) –8.56-8.53 (m, 2H), 8.50 (dd, 1H), 8.04 (d, 2H), 7.98 (d, 1H), 7.85 (dd, 1H), 7.76-7.12 (m, 28H), 6.97-6.93 (m, 1H), 6.42-6.29 (m, 7H), 6.11 (dd, 1H), 1.95 (s, 6H).

Synthesis Example 6

Production of Compound 125

Compound 125 was synthesized through the reaction pathway illustrated in Reaction Scheme 6:

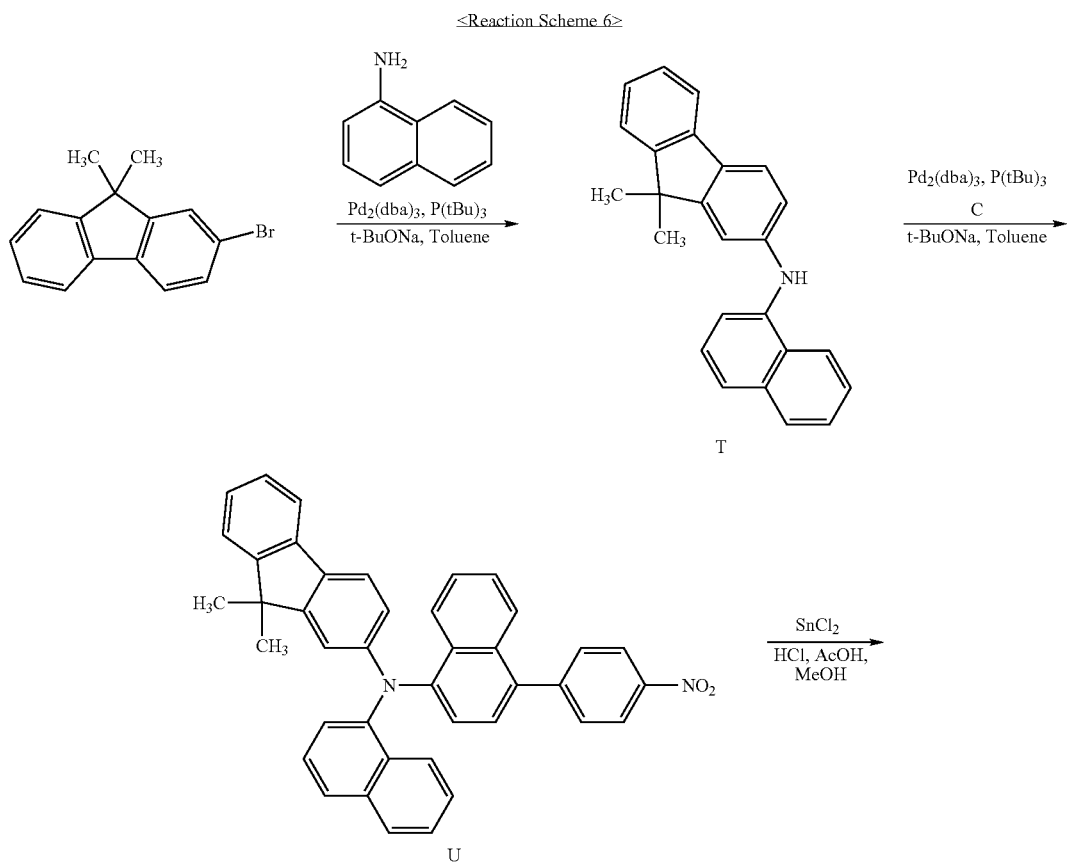

-continued

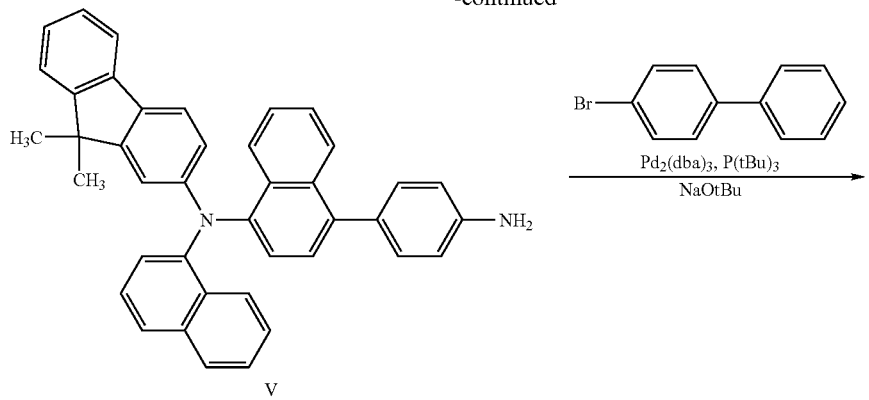

V

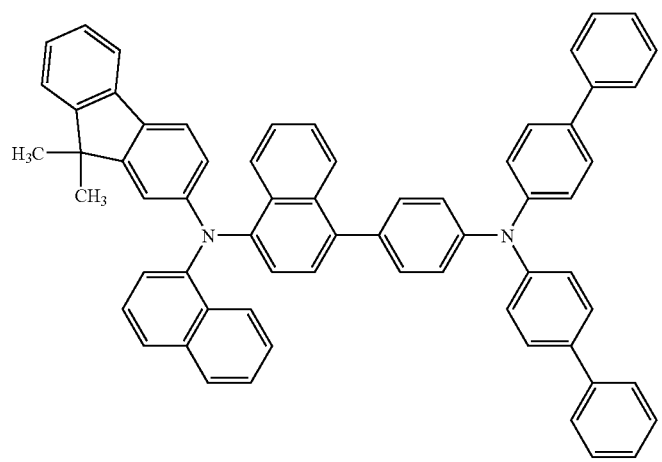

125

(25) Synthesis of Intermediate T 8.2 g (30 mmol) of 2-bromo-9,9-dimethylfluorene, 6.44 g (45 mmol) of 1-aminonaphthalene, 4.3 g (45 mmol) of t-BuONa, 0.55 g (0.6 mmol) of $Pd_2(dba)_3$, 0.12 g (0.6 mmol) of P(t-Bu)$_3$ were dissolved in 100 Ml of toluene and then, the mixture was stirred at 90° C. for 3 hours. After the reaction was completed, the reaction solution was cooled to room temperature and extracted three times with distilled water and 100 Ml of diethylether. The collected organic layers were dried over magnesium sulfate and a solvent contained therein was evaporated. The residue was isolated and refined by silica gel column chromatography to produce 8.55 g (yield 85%) of Intermediate T. $^1$H NMR (CDCl$_3$, 400 MHz) δ (ppm) –8.41 (dd, 1H), 7.82 (d, 1H), 7.72 (d, 1H), 7.59-7.36 (m, 5H), 7.24-7.09 (m, 4H), 6.97-6.93 (m, 1H), 6.55 (dd, 1H), 5.83 (s, NH), 1.85(s, 6H).

(26) Synthesis of Intermediate U

Intermediate U (yield: 63%) was synthesized by reacting Intermediate C and Intermediate T in a similar manner to the method of synthesizing Intermediate G. $^1$H NMR (CDCl$_3$, 400 MHz) δ (ppm) –8.49 (dd, 1H), 8.10-8.06 (m, 3H), 7.98 (dd, 1H), 7.85 (dd, 1H), 7.69-7.31 (m, 13H), 7.24-7.20 (m, 1H), 7.11 (dd, 1H), 6.97-6.93 (m, 1H), 6.29 (dd, 1H), 6.08 (dd, 1H), 1.05 (s, 6H).

(27) Synthesis of Intermediate V

Intermediate V (yield: 92%) was synthesized in the same manner as Intermediate H was synthesized, except that Intermediate U was used instead of Intermediate G. $^1$H NMR (CDCl$_3$, 400 MHz) δ (ppm) –8.49 (dd, 1H), 8.04 (d, 1H), 7.98 (d, 1H), 7.85 (dd, 1H), 7.69-7.31 (m, 13H), 7.24-7.20 (m, 1H), 7.11 (d, 1H), 6.97-6.93 (m, 1H), 6.70-6.66 (m, 2H), 6.29 (dd, 1H), 6.08 (dd, 1H), 5.48 (s, NH), 1.85 (s, 6H).

(28) Synthesis of Compound 125

6.04 g (10 mmol) of Intermediate V, 5.13 g (22 mmol) of 4-bromobiphenyl, 2.8 g (30 mmol) of t-BuONa, 0.36 g (0.4 mmol) of $Pd_2(dba)_3$ and 0.08 g (0.4 mmol) of P(t-Bu)$_3$ were dissolved in 50 Ml of toluene and then, the mixture was stirred at 90° C. for 3 hours. After the reaction was completed, the reaction solution was cooled to room temperature and extracted three times with distilled water and 100 Ml of diethylether. The collected organic layers were dried over magnesium sulfate and anysolvent contained therein was evaporated. The residue was isolated and refined by silica gel column chromatography to produce 5.57 g (yield 65%) of Compound 125. $^1$H NMR (CDCl$_3$, 400 MHz) δ (ppm) –8.49 (dd, 1H), 8.20 (d, 1H), 7.98 (d, 1H), 7.85 (dd, 1H), 7.76-7.29 (m, 27H), 7.24-7.20 (m, 1H), 7.11 (d, 1H), 6.97-6.93 (m, 1H), 6.47-6.41 (m, 6H), 6.29 (dd, 1H), 6.08 (dd, 1H), 1.85 (s, 6H).

Synthesis Example 7

Production of Compound 152

Compound 152 was synthesized through the reaction pathway illustrated in Reaction Scheme 7:

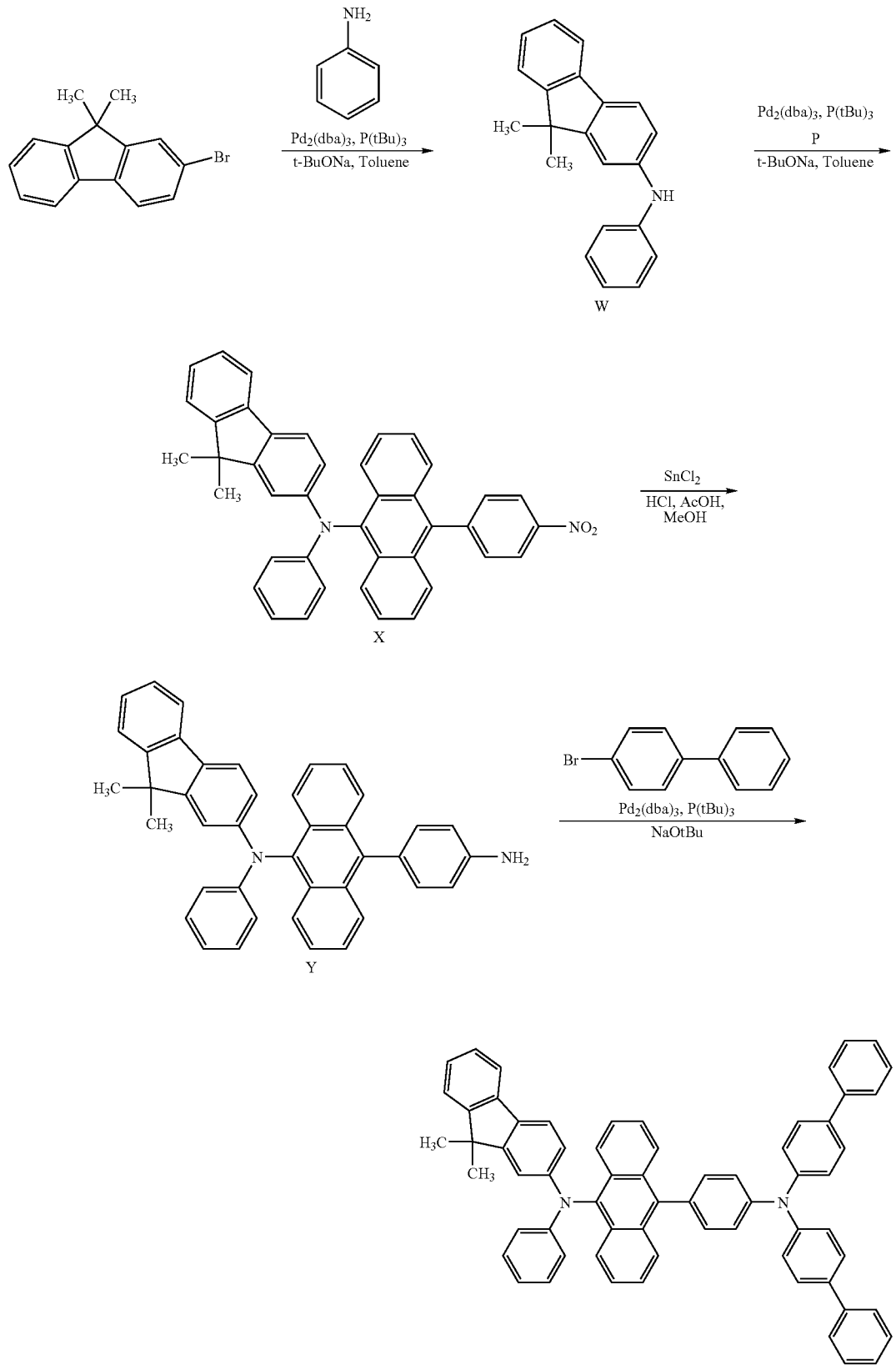
<Reaction Scheme 7>

(29) Synthesis of Intermediate W

Intermediate W (yield: 90%) was synthesized in the same manner as Intermediate T was synthesized, except that aniline was used instead of aminonaphthalene. $^1$H NMR (CDCl$_3$, 400 MHz) δ (ppm) −7.82 (d, 1H), 7.54-7.49 (m, 2H), 7.27-7.21 (m, 3H), 7.12-7.08 (m, 3H), 6.97-6.93 (m, 1H), 6.90-6.86 (m, 1H), 6.59-6.56 (m, 1H), 5.44(NH), 1.85(s, 6H).

(30) Synthesis of Intermediate X

Intermediate X (yield: 60%) was synthesized by reacting Intermediate P and Intermediate W in a similar manner to the method of synthesizing Intermediate U. $^1$H NMR (CDCl$_3$, 400 MHz) δ (ppm) −8.65-8.53 (m, 2H), 8.07-7.96 (m, 5H), 7.72-7.67 (m, 3H), 7.58-7.53 (m, 3H), 7.32-7.20 (m, 5H), 7.11 (d, 1H), 6.97-6.93 (m, 1H), 6.64-6.59 (m, 1H), 6.29 (dd, 1H), 5.63 (dd, 2H), 1.85 (s, 6H).

(31) Synthesis of Intermediate Y

Intermediate Y (yield: 87%) was synthesized in the same manner as Intermediate V was synthesized, except that Intermediate X was used instead of Intermediate U. $^1$H NMR (CDCl$_3$, 400 MHz) δ (ppm) −8.56-8.53 (m, 2H), 8.04 (d, 2H), 7.98 (d, 1H), 7.68 (d, 1H), 7.58-7.20 (m, 10H), 7.11 (d, 1H), 6.97-6.93 (m, 1H), 6.68-6.59 (m, 3H), 6.28 (dd, 1H), 5.63 (dd, 2H), 5.48 (s, NH), 1.85 (s, 6H).

(32) Synthesis of Compound 152

Compound 152 (yield: 55%) was synthesized in the same manner as Compound 125 was synthesized, except that Intermediate Y was used instead of Intermediate V. $^1$H NMR (CDCl$_3$, 400 MHz) δ (ppm) −8.56-8.53 (m, 2H), 8.04 (d, 2H), 7.98 (d, 1H), 7.76-7.20 (m, 25H), 7.11 (d, 1H), 6.97-6.93 (m, 1H), 6.64-6.59 (m, 1H), 6.47-6.38 (m, 6H), 6.29 (dd, 1H), 5.64-5.61 (m, 2H), 1.85 (s, 6H).

EXAMPLE 1

Manufacture of Organic Electroluminescent Device

As an anode, a 15 Ω/cm2 (1200 Å) ITO glass substrate (produced by Corning Co.) was cut to a size of 50 mm×50 mm×0.7 mm and then sonicated with isopropyl alcohol and pure water each for 5 minutes and washed by irradiation of ultraviolet rays for 30 minutes and exposure to ozone. Then, the resultant glass substrate was mounted in a vacuum deposition device. 2-TNATA which is known as a hole injecting material was vacuum-deposited on the glass substrate to form a hole injecting layer having a thickness of 600 Å, and then Compound 1 as a hole transporting compound was vacuum-deposited to form a hole transport layer having a thickness of 300 Å.

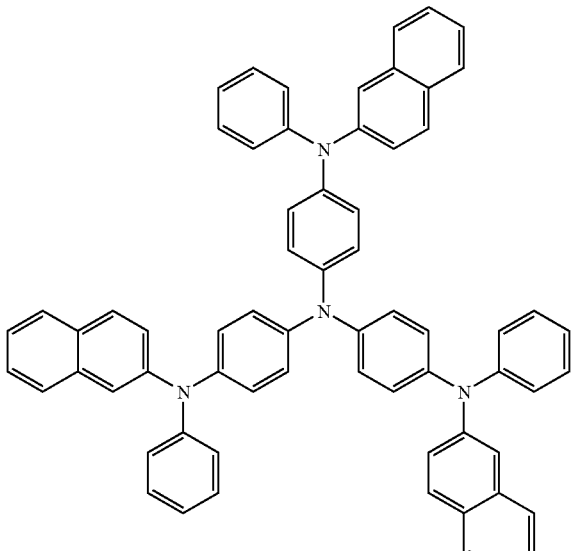

2-TNATA

Alq3, which is a known green fluorescent host, and C545T, which is a known green fluorescent dopant, were co-deposited in a weight ratio of 98:2 on the hole transport layer to form an emission layer having a thickness of 300 Å. Then, Alq3 was deposited on the emission layer to form an electron transport layer having a thickness of 300 Å, and then LiF, which is a halogenated alkali metal, was deposited on the electron transport layer to form an electron injection layer having a thickness of 10 Å and then Al was vacuum-deposited to form a cathode having a thickness 3000 Å, thereby forming an LiF/Al electrode. As a result, an organic electroluminescent device was completely manufactured. The organic electroluminescent device had a driving voltage of 6.52 V, high luminosity of 7,411 cd/m$^2$, a color coordinate of (0.310, 0.642), and a luminescent efficiency of 14.82 cd/A, at the current density of 50 mA/cm$^2$.

EXAMPLE 2

Manufacture of Organic Electroluminescent Device

An organic electroluminescent device was manufactured in the same manner as in Example 1, except that the hole transport layer was formed using Compound 8 instead of Compound 1. The organic electroluminescent device had a driving voltage of 6.67 V, high luminosity of 7,898 cd/m$^2$, a color coordinate of (0.309, 0.641), and a luminescent efficiency of 15.8 cd/A, at the current density of 50 mA/cm$^2$.

EXAMPLE 3

Manufacture of Organic Electroluminescent Device

An organic electroluminescent device was manufactured in the same manner as in Example 1, except that the hole transport layer was formed using Compound 17 instead of Compound 1. The organic electroluminescent device had a driving voltage of 6.75 V, high luminosity of 7,506 cd/m$^2$, a color coordinate of (0.309, 0.643), and a luminescent efficiency of 15.01 cd/A, at the current density of 50 mA/cm$^2$.

EXAMPLE 4

Manufacture of Organic Electroluminescent Device

An organic electroluminescent device was manufactured in the same manner as in Example 1, except that the hole transport layer was formed using Compound 35 instead of Compound 1. The organic electroluminescent device had a driving voltage of 6.45 V, high luminosity of 6,861 cd/m$^2$, a color coordinate of (0.311, 0.644), and a luminescent efficiency of 13.72 cd/A, at the current density of 50 mA/cm$^2$.

EXAMPLE 5

Manufacture of Organic Electroluminescent Device

An organic electroluminescent device was manufactured in the same manner as in Example 1, except that the hole transport layer was formed using Compound 53 instead of Compound 1. The organic electroluminescent device had a driving voltage of 6.72 V, high luminosity of 7,544 cd/m$^2$, a color coordinate of (0.310, 0.643), and a luminescent efficiency of 15.09 cd/A, at the current density of 50 mA/cm².

EXAMPLE 6

Manufacture of Organic Electroluminescent Device

An organic electroluminescent device was manufactured in the same manner as in Example 1, except that the hole transport layer was formed using Compound 125 instead of Compound 1. The organic electroluminescent device had a driving voltage of 6.43 V, high luminosity of 7,883 cd/m², a color coordinate of (0.309, 0.641), and a luminescent efficiency of 15.77 cd/A, at the current density of 50 mA/cm².

EXAMPLE 7

Manufacture of Organic Electroluminescent Device

An organic electroluminescent device was manufactured in the same manner as in Example 1, except that the hole transport layer was formed using Compound 152 instead of Compound 1. The organic electroluminescent device had a driving voltage of 6.92 V, high luminosity of 8,770 cd/m², a color coordinate of (0.310, 0.642), and a luminescent efficiency of 17.54 cd/A, at the current density of 100 mA/cm².

COMPARATIVE EXAMPLE 1

An organic electroluminescent device was manufactured in the same manner as in Example, 1, except that the hole transport layer was formed using N,N'-bis-(1-naphthalenyl)-N,N'-bis-(1,1'-biphenyl)-4,4'diamine (NPB) that is a known material instead of Example 1. The organic electroluminescent device had a driving voltage of 7.45 V, high luminosity of 6,102 cd/m² a color coordinate of (0.309, 0.642), and a luminescent efficiency of 12.2 cd/A, at the current density of 50 mA/cm².

Organic electroluminescent devices manufactured using compounds represented by Formula 1 or Formula 2 as a hole transporting material according to aspects of the present invention had at least 0.5 V lower driving voltage than an organic electroluminescent device manufactured using NPB that is a known material, and showed high efficiency and l-V-L characteristics. Therefore, an organic electroluminescent device having a low driving voltage, high efficiency, high luminosity, and a long lifetime can be manufactured based on excellent hole injecting and hole transporting characteristics.

The fluorene-containing compound represented by Formula 1 or Formula 2 has excellent electrical characteristics and an excellent charge transporting capability, and so can be used as a hole injecting material, hole transporting material, and/or emitting material that is suitable for all-color fluorescent and phosphorescent devices, such as red, green, blue, and white fluorescent and phosphorescent devices. Accordingly, an organic electroluminescent device employing the fluorene-containing compound represented by Formula 1 or Formula 2 has high efficiency, a low driving voltage, high brightness, and a long lifetime.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:
1. A fluorine-containing compound represented by Formula 1 or Formula 2:

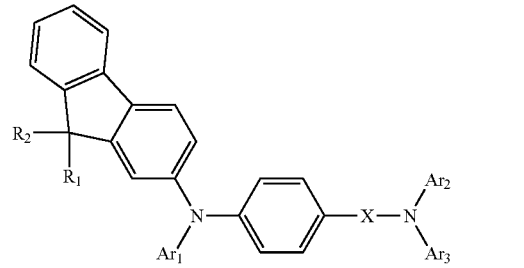

<Formula 1>

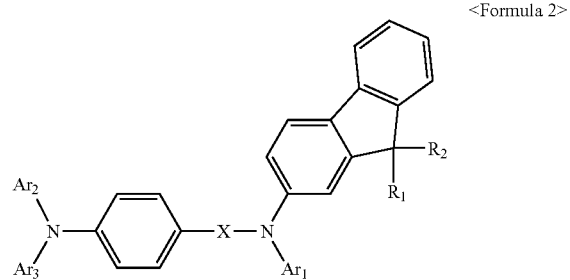

<Formula 2> wherein $Ar_1$, $Ar_2$ and $Ar_3$ are each, independently, an aryl group selected from the group consisting of an unsubstituted biphenyl group, a phenyl group, and a naphthyl group, wherein the phenyl group and naphthyl group may be unsubstituted or substituted with one, two or three substituents selected from the groups consisting of a C1-C4 alkyl group, a C1-C5 alkoxygroup, a cyano group, and amine group, a phenoxy group, a phenyl group and a halogen, X is one of the following structures:

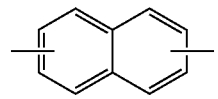

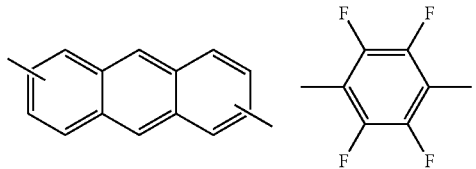

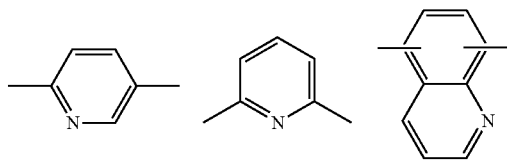

-continued

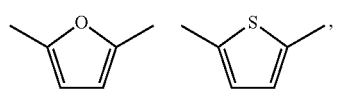

and

R$_1$, and R$_2$ are, each independently, a C1-C10 substituted or unsubstituted alkyl group, a C6-C20 aryl group, a C1-C10 substituted or unsubstituted alkoxy group, a fluorine group, a cyano group, or an amine group.

2. The fluorine-containing compound of claim 1, wherein each of Ar$_1$, Ar$_2$ and Ar$_3$ is selected from the group consisting of a phenyl group, a methylphenyl group, a naphthyl group and a biphenyl group.

3. The fluorine-containing compound of claim 1, wherein X is one of the following structures:

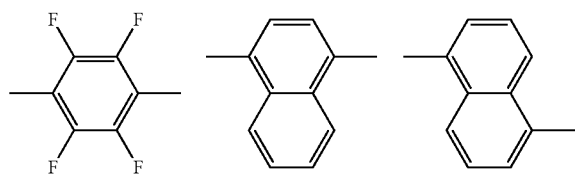

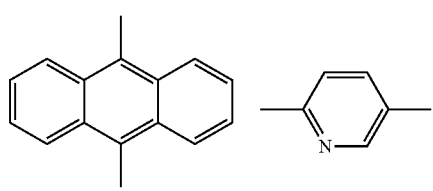

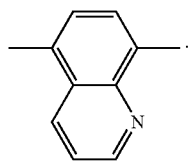

4. The fluorene-containing compound of claim 1, wherein R is selected from the substituents consisting of a C1-C10 alkyl group and a C6-C20 aryl group.

5. The fluorine-containing compound of claim 1, wherein the fluorine-containing compound is any one compound selected from compounds having the following structures:

1

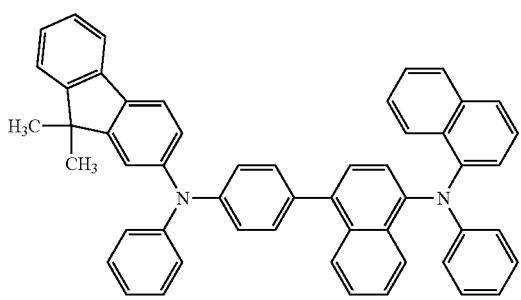

-continued

8

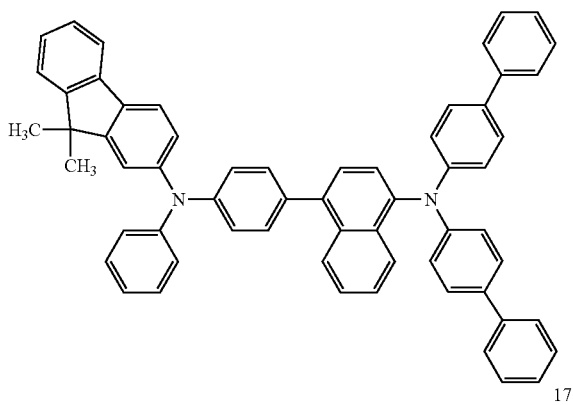

17

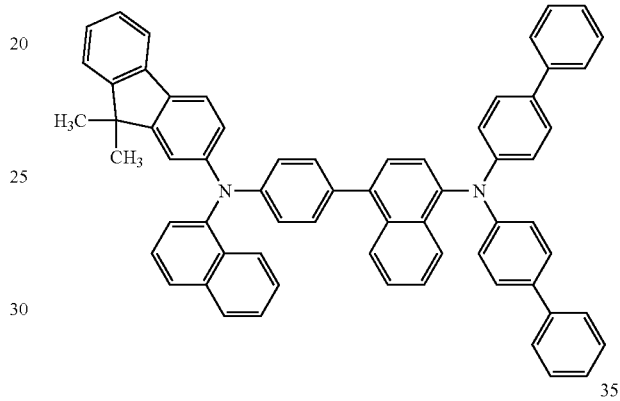

35

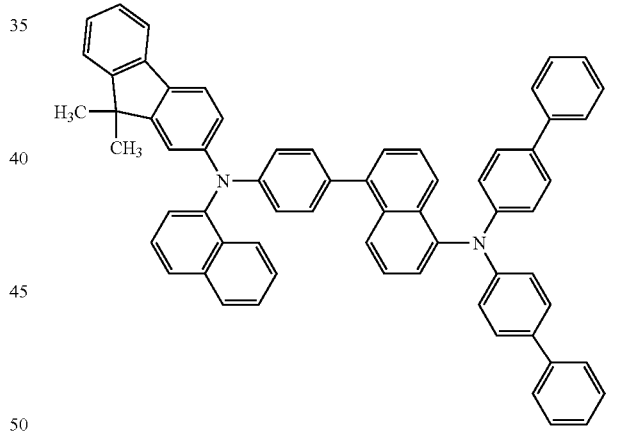

44

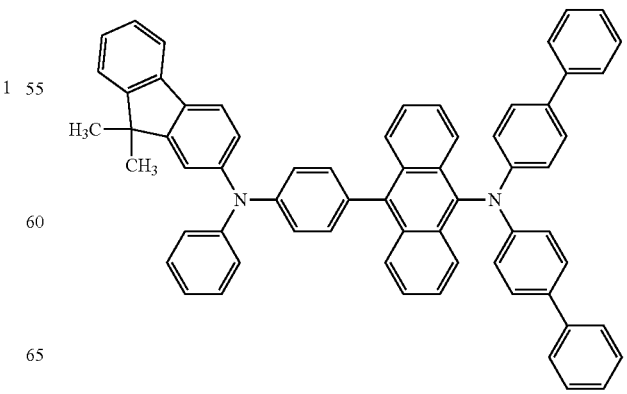

-continued

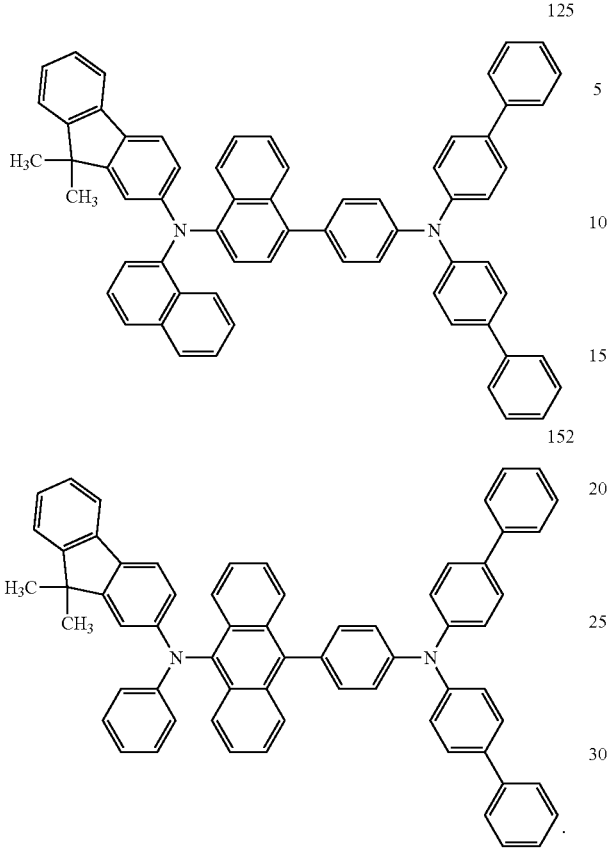

6. An organic electroluminescent device comprising:
a first electrode;
a second electrode;
an organic layer interposed between the first electrode and the second electrode; and
a fluorene-containing compound in the organic layer, which fluorene-containing compound is represented by Formula 1 or Formula 2:

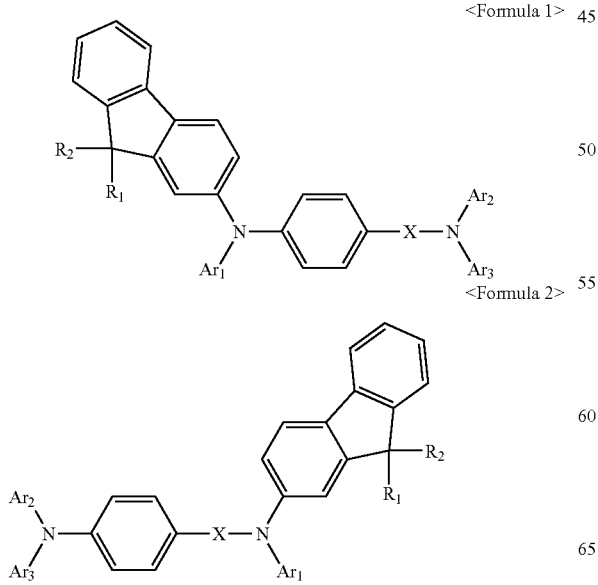

wherein $Ar_1$, $Ar_2$ and $Ar_3$ are each, independently, an aryl group selected from the group consisting of an unsubstituted biphenyl group, a phenyl group, and a naphthyl group, wherein the phenyl group and naphthyl group may be unsubstituted or substituted with one, two or three substituents selected from the groups consisting of a C1-C4 alkyl group, a C1-C5 alkoxygroup, a cyano group, and amine group, a phenoxy group, a phenyl group and a halogen, X is one of the following structures:

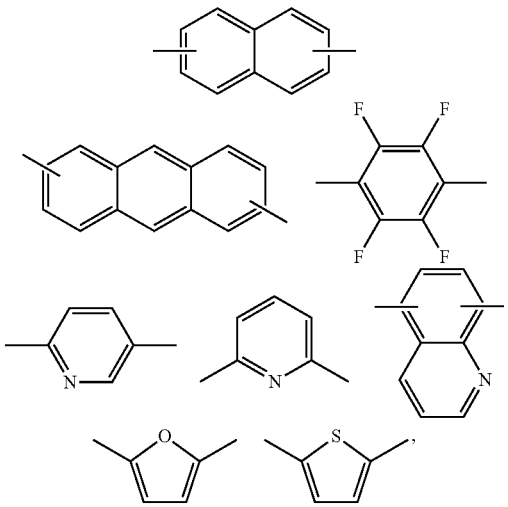

and $R_1$, and $R_2$ are, each independently, a C1-C10 substituted or unsubstituted alkyl group, a C6-C20 aryl group, a C1-C10 substituted or unsubstituted alkoxy group, a fluorine group, a cyano group, or an amine group.

7. The organic electroluminescent device of claim 6, wherein each of $Ar_1$, $Ar_2$ and $Ar_3$ is selected from the group consisting of a phenyl group, a methylphenyl group, a naphthyl group and a biphenyl group.

8. The organic electronluminescent device of claim 6, wherein X is one of the following structures:

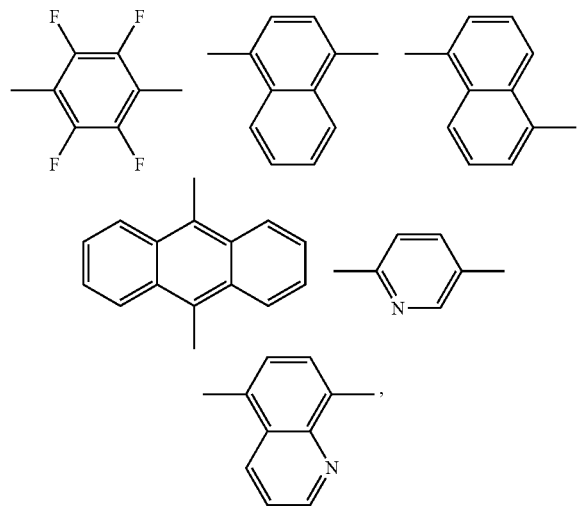

9. The organic electroluminescent device of claim 6, wherein R is selected from the substituents consisting of a C1-C10 alkyl group and a C6-C20 aryl group.

10. The organic electroluminescent device of claim 6, wherein the fluorine-containing compound is any one compound selected from compounds having the following structures:

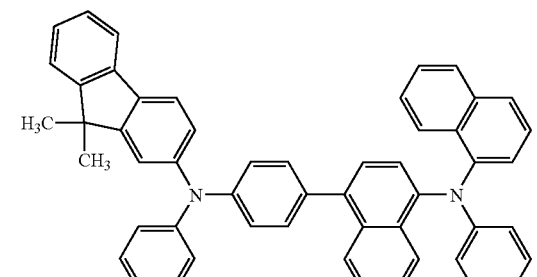

1

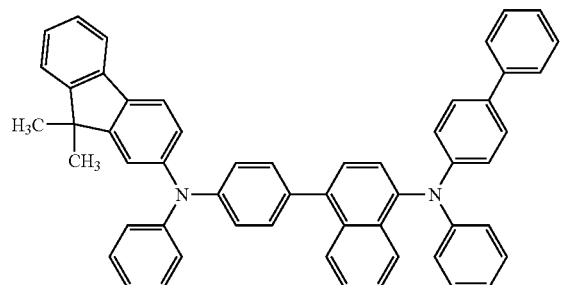

8

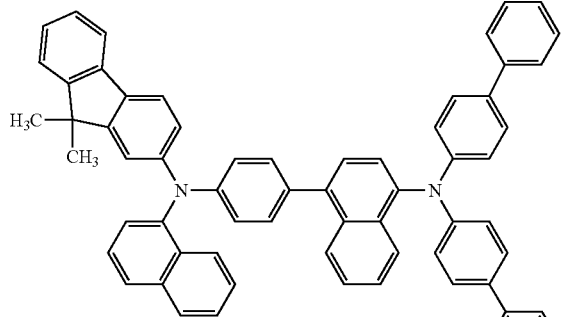

17

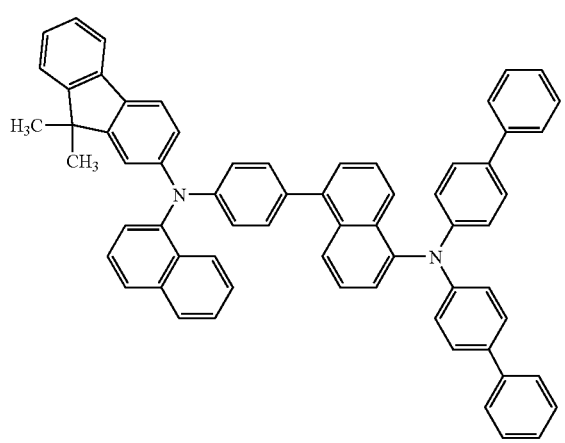

35

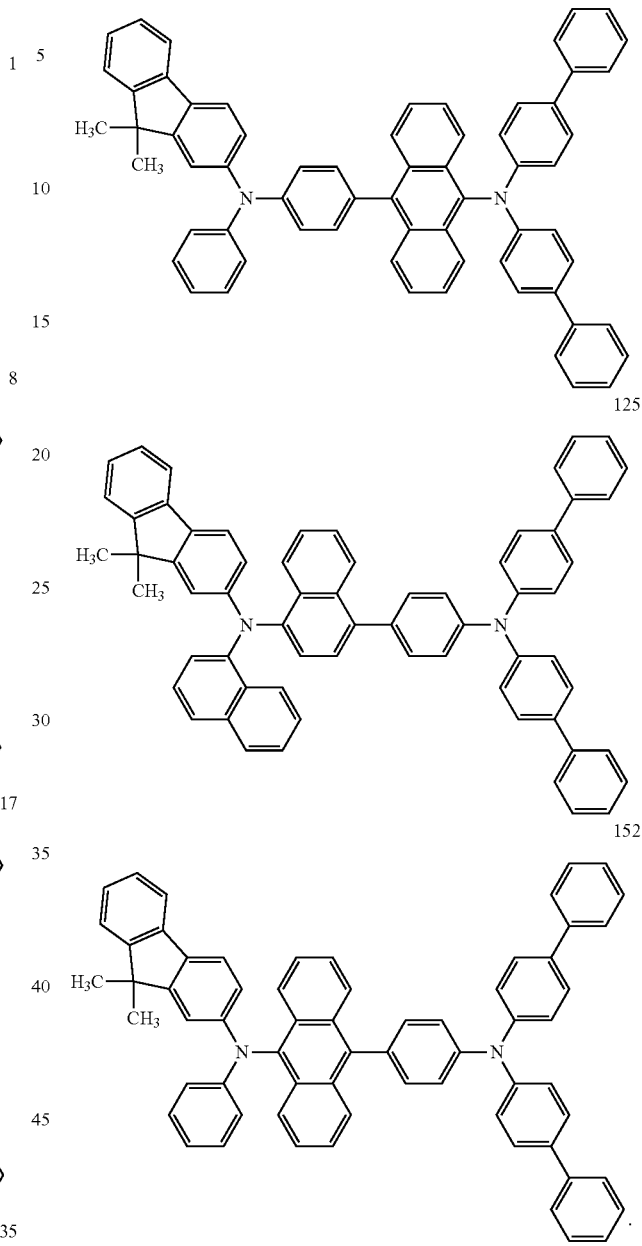

44

125

152

11. The organic electroluminescent device of claim 6, wherein the organic layer is selected from a hole injection layer and a hole transport layer.

12. The organic electroluminescent device of claim 6, wherein the organic layer is a single layer having a hole injecting capability and a hole transporting capability.

13. The organic electroluminescent device of claim 6, wherein the organic layer is the emission layer.

14. The organic electroluminescent device of claim 6, wherein the organic layer further comprises at least one layer selected from the group consisting of a hole injection layer, a hole transport layer, an electron blocking layer, an emission layer, a hole blocking layer, an electron transport layer, and an electron injection layer.

15. The organic electroluminescent device of claim 14, wherein the organic electroluminescent device comprises a structure selected from the group consisting of a structure of first electrode/hole injection layer/emission layer/second electrode, a structure of first electrode/hole injection layer/hole transport layer/emission layer/electron transport layer/second electrode, and a structure of first electrode/hole injection layer/hole transport layer/emission layer/electron transport layer/electron injection layer/second electrode.

16. A flat panel display device comprising:
a first electrode;
a second electrode;
an organic layer interposed between the first electrode and the second electrode; and
a fluorene-containing compound in the organic layer, which fluorene-containing compound is represented by Formula 1 or Formula 2:

<Formula 1>

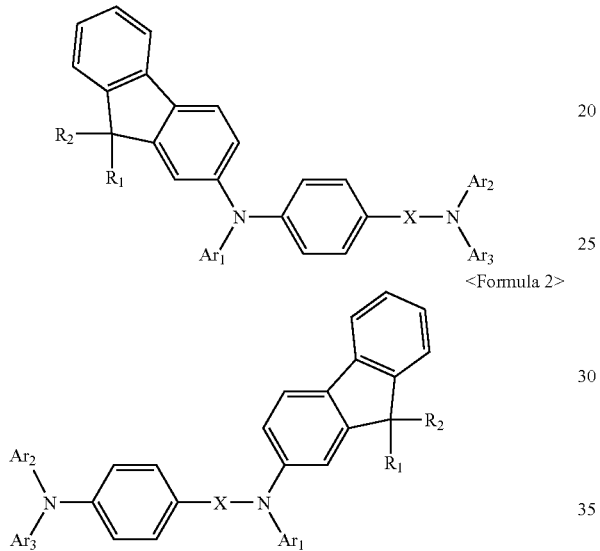

<Formula 2> wherein $Ar_1$, $Ar_2$ and $Ar_3$ are each, independently, a C6-C20 substituted or unsubstituted aryl group, a C6-C20 substituted or unsubstituted aryloxy group, a C4-C20 substituted or unsubstituted heteroring, or a C4-C20 substituted or unsubstituted condensed polycyclic group, X is one of the following structures:

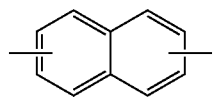

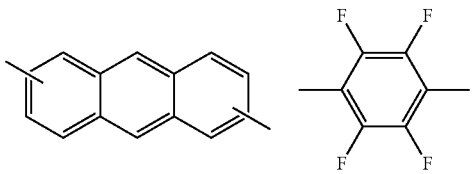

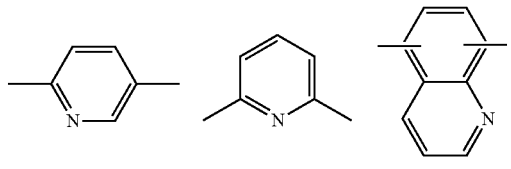

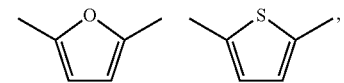

$R_1$, and $R_2$ are, each, independently, a C1-C10 substituted or unsubstituted alkyl group, a C6-C20 aryl group, a C1-C10 substituted or unsubstituted alkoxy group, a fluorine group, a cyano group, or an amine group, and the first electrode is electrically connected to a source electrode or drain electrode of a thin film transistor.

* * * * *